(12) United States Patent
Jaffe et al.

(10) Patent No.: US 8,161,971 B2
(45) Date of Patent: Apr. 24, 2012

(54) NASAL AND ORAL PATIENT INTERFACE

(75) Inventors: Michael B. Jaffe, Cheshire, CT (US);
Ivan Bustamante, Meriden, CT (US);
Kimberly A. Golden, Wallingford, CT
(US); Randall J. Terry, Wallingford, CT
(US); Patrick Tuxbury, Wallingford, CT
(US); John A. Triunfo, Jr., Fairfield, CT
(US); Anthony T. Pierry, Plantsville,
CT (US); Gregory Kenny, Wakefield,
MA (US); Anthony Pannozzo,
Needham, MA (US); John DePiano,
Burlington, MA (US); **Julia Rose
Anderson, Melrose, MA (US); Eric
Hyman**, South Grafton, MA (US);
Deirdre McKeown, Boston, MA (US)

(73) Assignee: Ric Investments, LLC, Wilmington, DE (US)

( * ) Notice: Subject to any disclaimer, the term of this patent is extended or adjusted under 35 U.S.C. 154(b) by 30 days.

(21) Appl. No.: 11/888,677

(22) Filed: Aug. 1, 2007

(65) Prior Publication Data
US 2008/0190436 A1  Aug. 14, 2008

Related U.S. Application Data

(60) Provisional application No. 60/835,735, filed on Aug. 4, 2006, provisional application No. 60/947,523, filed on Jul. 2, 2007.

(51) Int. Cl.
*A61M 15/08* (2006.01)
*A61M 15/00* (2006.01)
*A61M 16/00* (2006.01)

(52) U.S. Cl. ......... 128/206.11; 128/207.18; 128/203.22; 128/200.24

(58) Field of Classification Search .................. 128/857, 128/858, 863, 200.24, 200.26, 203.12, 203.13, 128/203.18, 203.22, 204.18, 206.11, 207.13, 128/207.18, DIG. 26; 604/93.01, 94.01, 604/174, 516, 164.04, 103.03; 600/484, 600/529, 532
See application file for complete search history.

(56) References Cited

U.S. PATENT DOCUMENTS

| | | | | |
|---|---|---|---|---|
| 2,185,997 A * | 1/1940 | Heidbrink | ............... | 128/204.29 |
| 2,245,969 A * | 6/1941 | Francisco et al. | ........ | 128/207.18 |
| 2,259,817 A * | 10/1941 | Hawkins | .................. | 128/207.18 |
| 3,747,597 A * | 7/1973 | Olivera | ................... | 128/206.11 |
| 3,915,173 A * | 10/1975 | Brekke | .................... | 128/207.18 |
| 4,054,133 A * | 10/1977 | Myers | ..................... | 128/204.26 |
| 4,708,446 A * | 11/1987 | Timmons et al. | ............. | 351/158 |
| 4,782,832 A * | 11/1988 | Trimble et al. | .......... | 128/207.18 |
| 4,808,160 A * | 2/1989 | Timmons et al. | .......... | 604/94.01 |
| 4,932,943 A * | 6/1990 | Nowak | .......... | 604/180 |
| 4,986,815 A * | 1/1991 | Schneider | ..................... | 604/180 |
| 5,042,478 A * | 8/1991 | Kopala et al. | ............ | 128/207.18 |
| 5,137,017 A | 8/1992 | Salter | | |
| 5,193,534 A * | 3/1993 | Peppler | ..................... | 128/207.18 |
| 5,335,656 A | 8/1994 | Bowe et al. | | |
| 5,335,659 A * | 8/1994 | Pologe | ......................... | 600/473 |
| 5,474,063 A * | 12/1995 | Riendeau | ................. | 128/207.18 |
| 5,477,852 A * | 12/1995 | Landis et al. | ............ | 128/207.18 |
| 5,533,506 A * | 7/1996 | Wood | ........................ | 128/207.18 |
| 5,687,715 A * | 11/1997 | Landis et al. | ............ | 128/207.18 |
| 5,752,511 A * | 5/1998 | Simmons et al. | ........ | 128/207.18 |
| 6,328,038 B1 * | 12/2001 | Kessler et al. | ........... | 128/207.18 |

(Continued)

*Primary Examiner* — Annette Dixon

(57) ABSTRACT

A patient interface for communicating fluids to and/or from a patient's nasal cavity and/or oral cavity is disclosed. In addition, a patient interface for fluid and physiological function monitoring proximate to the patient's nasal cavity and/or oral cavity is disclosed. An apnea monitor and a method for monitoring apnea are also disclosed.

20 Claims, 30 Drawing Sheets

U.S. PATENT DOCUMENTS

| | | | |
|---|---|---|---|
| 6,669,712 B1 * | 12/2003 | Cardoso | 606/199 |
| 6,763,832 B1 * | 7/2004 | Kirsch et al. | 128/207.18 |
| 6,793,629 B2 * | 9/2004 | Rapoport et al. | 600/533 |
| 6,938,619 B1 * | 9/2005 | Hickle | 128/207.18 |
| 6,986,353 B2 * | 1/2006 | Wright | 128/207.18 |
| 7,007,694 B2 * | 3/2006 | Aylsworth et al. | 128/206.11 |
| 7,156,097 B2 * | 1/2007 | Cardoso | 128/206.11 |
| 7,267,123 B2 * | 9/2007 | Aylsworth et al. | 128/207.18 |
| 7,445,602 B2 * | 11/2008 | Yamamori et al. | 600/532 |
| 7,455,644 B2 * | 11/2008 | Yamamori et al. | 600/532 |
| 7,814,911 B2 * | 10/2010 | Bordewick et al. | 128/207.13 |
| 2002/0143296 A1 * | 10/2002 | Russo | 604/180 |
| 2003/0094178 A1 * | 5/2003 | McAuley et al. | 128/207.18 |
| 2003/0111081 A1 | 6/2003 | Gupta | |
| 2004/0261797 A1 * | 12/2004 | White et al. | 128/206.11 |
| 2005/0257794 A1 * | 11/2005 | Aylsworth et al. | 128/207.18 |
| 2006/0000472 A1 * | 1/2006 | Fenton | 128/200.24 |
| 2008/0051674 A1 * | 2/2008 | Davenport et al. | 600/561 |

* cited by examiner

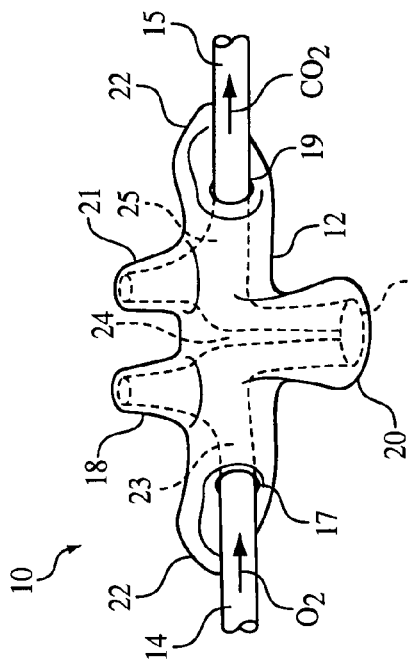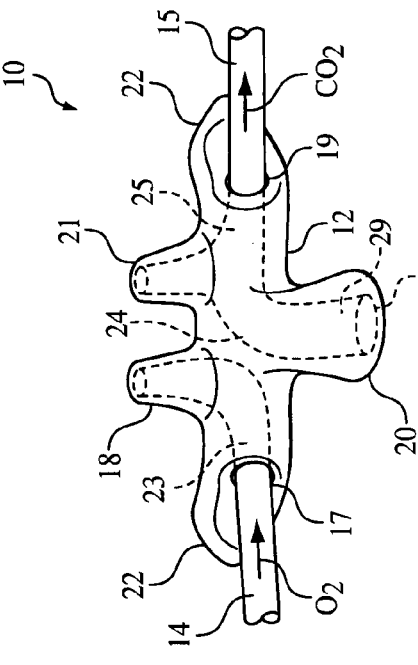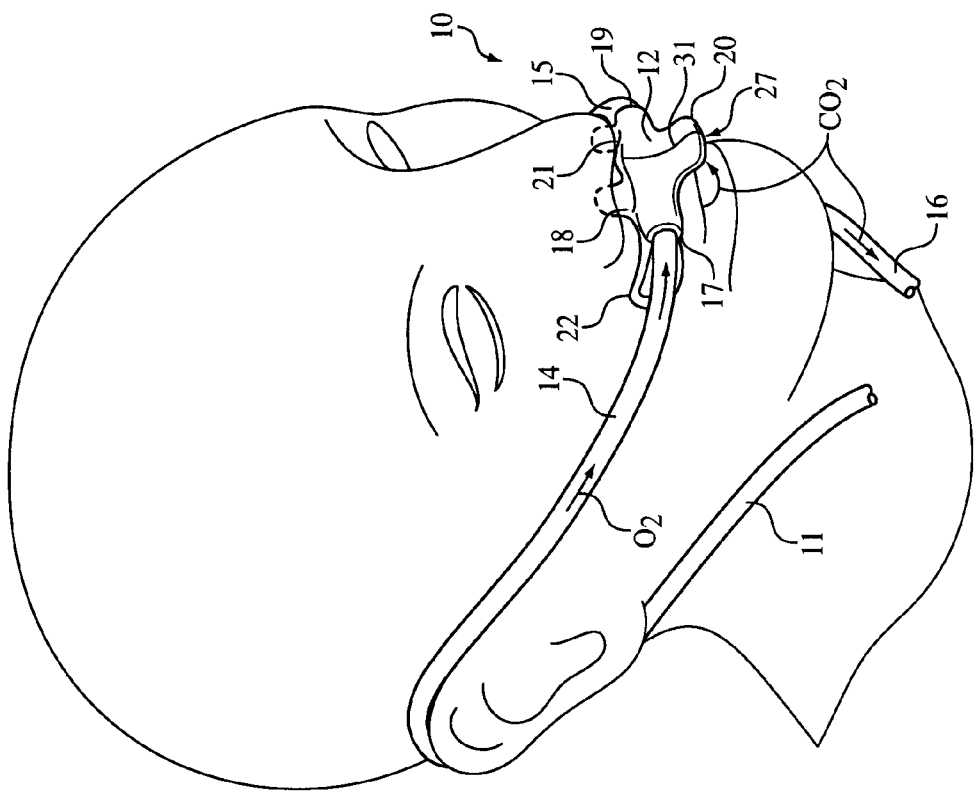

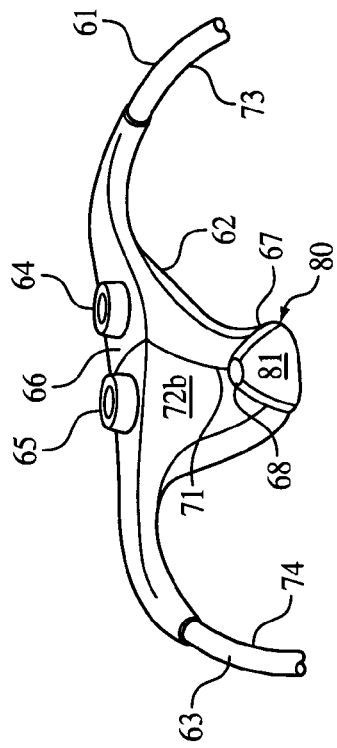
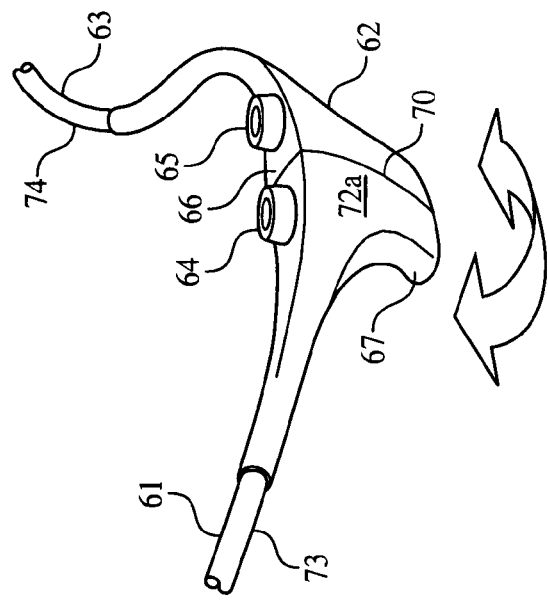
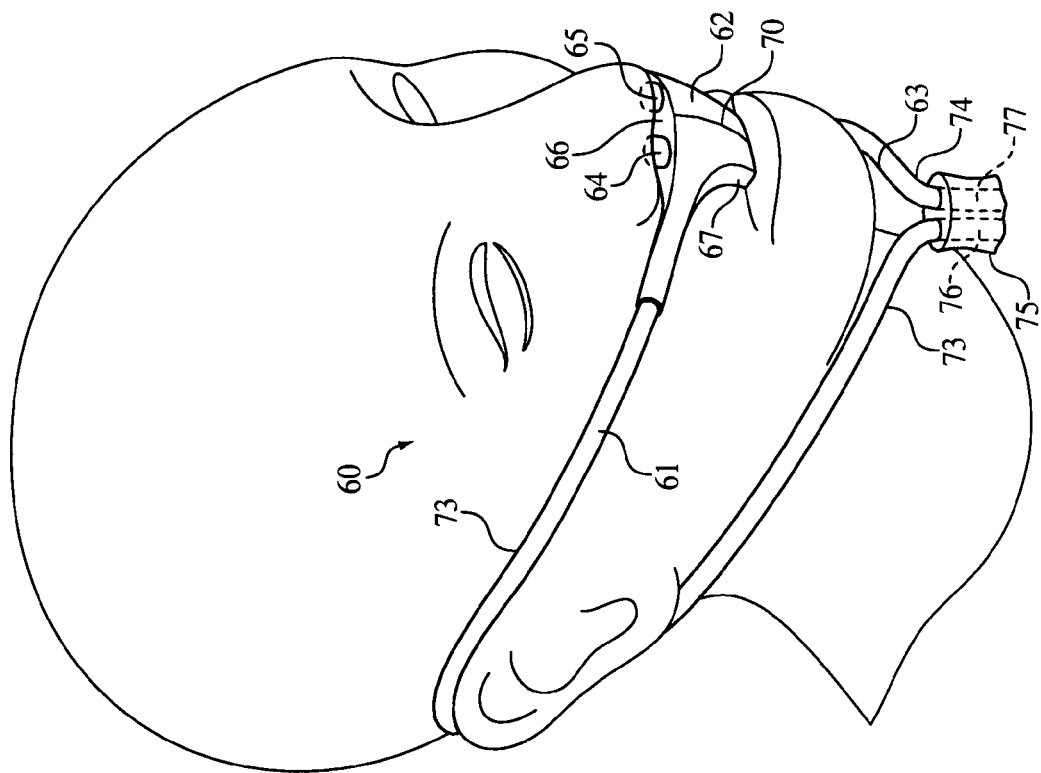

NASAL AND ORAL PATIENT INTERFACE

CROSS-REFERENCE TO RELATED APPLICATIONS

This application claims priority under 35 U.S.C.§119(e) from provisional U.S. patent application Nos. 60/835,735, filed Aug. 4, 2006, and 60/947,523, filed Jul. 2, 2007, the contents of both of which are incorporated herein by reference.

BACKGROUND OF THE INVENTION

1. Field of the Invention

The present invention relates to improved patient interfaces for carbon dioxide sampling, supplemental oxygen delivery, and combined carbon dioxide sampling and supplemental oxygen delivery. In addition, the present invention relates to nasal and oral patient interfaces for gas and physiological function monitoring, and for other monitoring modalities. The present invention is further related to the combination of a nasal carbon dioxide sampler and a nasal/alar central photoplethysmographic sensor that can be used as an apnea detector.

2. Description of the Related Art

A sidestream type of gas sampling system transports a flow of gas from the patient's airway through a sampling tube, to a sample cell, where the constituents of the gas are measured by a gas sensing system. Gases are continuously aspirated through the sampling tube, and into the sample cell, which is located typically within a gas measurement instrument. Gases are commonly sampled at flow rates ranging from about 50 ml/min to about 250 ml/min.

For purposes of description, the discussion herein is focused on patient interfaces and/or cannulas for use with human patients, it being understood that the present invention is not limited in scope only to use with human patients and can beneficially be used in various other contexts. For example, the present invention may also be used in the area of veterinary medicine where the "patients" are animals.

Different types of oral/nasal cannulas are used to deliver oxygen to patients who need assistance to breathe properly, to collect a gas sample from patients to monitor respiration, or to perform both functions. Such cannulas are used when direct ventilation is not provided. The term "oral/nasal" refers to the adaptable configuration of such cannulas, which can be in close proximity to the oral cavity (mouth) or inserted into the nasal cavity (nostril(s) or nares) of the patient. In either arrangement, a sidestream of the patient's exhaled breath flows through the cannula to a gas analyzer to be analyzed. The results of this non-invasive analysis provide an indication of the patient's condition, such as the state of the patient's pulmonary perfusion, respiratory system, and/or metabolism.

Some nasal interfaces for carbon dioxide sampling are perceived failing to remain in position during monitoring and uncomfortable. Also, differences between patients, in particular, in the spacing between the patient's nostrils, and the spacing between the patient's nose and mouth, as well as differences in airflow from the nostrils should be considered.

In addition, the nasal resistance between subjects can vary significantly. As such, the nasal airflow can often be quite asymmetric between the two nostrils. This can affect the efficiency of oxygen delivery, as the delivery will depend upon the nature of an obstruction in one or both nostrils, and how the oxygen is delivered. Existing nasal carbon dioxide sampling and oxygen delivery cannulas either deliver to a single nostril, deliver equally to both nostrils, or produce a "cloud" of oxygen, which is inhaled by the subject. A simple means to preferentially direct oxygen to the less obstructed nostril is desired.

In addition to sidestream sampling techniques, the present invention also relates to various monitoring techniques. It is known that if oxygen levels in the blood become very low at peripheral sites, a variety of clinical problems may occur. In addition, diseases, acute injuries, and other conditions can adversely affect blood flow to and in the limbs, and poor blood flow reduces the amount of oxygen that is carried in the blood stream to cells.

In general, blood oxygen levels are currently measured by pulse oximetry, which can be categorized into transmittance and reflectance types. Transmittance, or transillumination oximetry, involves the process in which a sensor measures light extinction as light passes through a portion of blood-perfused tissue. Light is transmitted from one side of a portion of blood-perfused tissue, and is recorded by a detector situated on the opposite side of the same portion of tissue. Reflectance oximetry, on the other hand, has both the light source and the detector on one side of the tissue, and measures reflectance back from the tissue.

For both types of oximetry, multiple signals from the light sensor, or detector, may be used to estimate the oxygen saturation in the blood and/or pulse rate from changes in absorption of the light detected throughout blood pulse cycles. The technology is based on the differential absorbance of different wavelengths of light by different species of hemoglobin, as known in the art.

Conventional pulse oximetry measurement in certain classes of patients, for instance severely burned patients, can be a significant challenge, yet this monitoring data is vital in operating room and intensive care settings. Most current pulse oximetric approaches depend upon available peripheral sites permitting transillumination oximetry, which is sufficient for most surgical conditions and procedures. However, in some instances, such as patients with severe burns, only a few sites may be suitable for the effective placement of the transmitting pulse oximeter sensor. These patients often have severely comprised circulatory function, thereby rendering the current peripheral pulse oximeters less effective. Therefore, it is desirable to measure to measure oxygen saturation from a central measure.

With respect monitoring, a robust and inexpensive apnea monitor, for example, particularly for adults, has yet to appear on the market. In the United States, an apnea monitor is defined by the Code of Federal Regulations as "a complete system intended to alarm primarily upon the cessation of breathing timed from the last detected breath. The apnea monitor also includes indirect methods of apnea detection, such as monitoring of heart rate and other physiological parameters linked to the presence or absence of adequate respiration." 21 C.F.R.§868.2377. An easy to apply device with robust and redundant detection methods of apneas is desired.

The present invention is further concerned with providing a simple way of performing ambulatory sleep diagnostic studies. An easy to apply single-site device that provides the ability to sense directly or surrogates of effort, $SpO_2$, or flow is desired.

SUMMARY OF THE INVENTION

Accordingly, one aspect of the present invention provides a patient interface with improved stability and comfort to the patient. This object is achieved by providing a patient interface that includes a body portion configured to communicate with at least one fluid path. At least one nostril interface extends from the body portion and is configured to be inserted into a nostril of a patient and to be in communication with the at least one fluid path. A pair flexible stabilizers extend from the body portion on opposite sides of the body portion and are configured to substantially conform to the patient when the interface is mounted to the patient.

In another embodiment, this object is achieved by providing a patient interface that includes a body portion configured to communicate with first and second fluid paths. First and second nostril interfaces project from a first side of the body portion. The first nostril interface communicates with the first fluid path, the second nostril interface communicating with the second fluid path, the first and second nostril interfaces being configured to be inserted into left and right nostrils of a patient, respectively, when the body portion is in a first orientation, so as to communicate the first fluid path with the left nostril and the second fluid path to the right nostril. Third and fourth nostril interfaces projecting from a second side of the body portion, the third nostril interface communicate with the first fluid path. The fourth nostril interface communicates with the second fluid path. The third and fourth nostril interfaces are configured to be inserted into the right and left nostrils of the patient, respectively, when the body portion is in a second orientation, so as to communicate the first fluid path with the right nostril and the second fluid path to the left nostril.

In another embodiment, this object is achieved by providing a patient interface that includes a body portion configured to communicate with two fluid paths. A pair of nostril interfaces project from the body portion. An oral sampler portion is operatively joined to the body portion and has an orifice configured to communicate with at least one of the fluid paths. The oral sampler portion comprises an adjustable structure that enables an orientation of the orifice of the oral sampler portion to be changed and retained in different positions.

In another embodiment, this object is achieved by providing a patient interface that includes a body portion configured to communicate with at least one fluid path. An adjustable nostril interface is operatively connected to the body portion. The nostril interface is configured to be received by a nostril of the patient's nose and in communication with the fluid path. The nostril interface comprises an adjustable structure to enable a length and/or orientation of the nostril interface to be adjustable relative to the body portion.

In another embodiment, this object is achieved by providing a patient interface that includes a body portion configured to communicate with at least one fluid path. A nostril interface is operatively connected with the body portion to communicate the fluid path with a nostril. An attachment device is constructed and arranged to attach the body portion to the nose of a patient. The attachment device includes a nose engaging portion connected with the device for engaging an external surface of the patient's nose.

In another embodiment, this object is achieved by providing a patient interface that includes a tubing defining a fluid path, the tubing having an orifice at one end of the fluid path and through which a fluid is communicated from or to a patient. A body portion comprises a tubing holder portion that is constructed and arranged to secure a portion of the tubing that is spaced from the orifice for positioning the orifice to communicate the fluid path with the patient. A mounting structure is provided for mounting the body portion to the head of the patient.

In another embodiment, this object is achieved by providing a patient interface that includes a body portion configured to communicate with a fluid path. At least a section of the body portion is inflatable by a fluid. A nostril interface extends from the body portion and is constructed and arranged to communicate a nostril of a patient with the fluid path.

In another embodiment, this object is achieved by providing a patient interface that includes a body portion configured to communicate with a fluid path. A nostril interface and at least one attachment portion extends from the body portion. An adhesive is provided on the attachment portion to removably attach the attachment portion to a patient's face.

In another embodiment, this object is achieved by providing a patient interface that includes a first nostril interface configured to be inserted into a first nostril of a patient and comprising a first conduit for communicating with the first nostril of the patient. A second nostril interface is configured to be inserted into a second nostril of the patient and comprising a second conduit for communicating with the second nostril of the patient. The first nostril interface is capable of relative sliding movement with respect to the second nostril interface to enable an adjustment of spacing therebetween.

In another embodiment, this object is achieved by providing a patient interface that includes an integrally formed structure including (1) a tubing portion defining first and second fluid paths, and (2) an appliance portion that includes a first nostril interface that communicates with the first fluid path, and a second nostril interface that communicates with the second fluid path.

In another embodiment, this object is achieved by providing a patient interface that includes a body portion configured to communicate with a fluid path. A nostril interface in communication with the fluid path extends from the body portion. A securement portion also extends from the body portion. The securement portion is disposed proximate the nostril interface and engages an exterior surface of the patient's nose. The nostril interface and the securement portion are cooperable to clamp a portion of the patient's nose therebetween.

In another embodiment, this object is achieved by providing a patient interface that includes a body portion configured to communicate with a fluid path. A nostril interface extends from the body portion and is in communication with the fluid path. A securement portion extends from the body portion. The securement portion is disposed proximate the nostril interface and comprises two clamping portions for clamping a portion of the patient's nose therebetween.

In another embodiment, this object is achieved by providing a patient interface that includes a head mount configured to be secured on the head of a patient. The head mount includes a docking portion constructed and arranged to be disposed proximate to the nose of the patient. An appliance is provided to be removably attached to the docking portion. The appliance portion includes a nostril interface for communicating a fluid path to the nostril of the patient.

In another embodiment, this object is achieved by providing a patient interface that includes a body portion having a first passage configured to communicate with a first fluid path that withdraws a first fluid from a patient. A second passage is configured to communicate with a second fluid path that supplies a second fluid to the patient. A nostril interface extends from the body portion and is configured to be received by a nostril of the patient's nose. The nostril interface has a first orifice that communicates with the first passage of the body portion to receive the first fluid from the patient. A second orifice communicates with the second passage of the body portion to output the second fluid to the patient.

In another embodiment, this object is achieved by providing a nostril interface configured to be inserted into a nostril of a patient. The nostril interface includes an inner conduit extending through the nostril interface. The inner conduit is configured to receive a first fluid from the nostril of the patient. An outer conduit surrounds at least a portion of the inner conduit. The outer conduit is configured to supply a second fluid to the nostril of the patient. A moisture exchanger is configured to receive moisture from the first fluid and to supply the moisture to the second fluid.

In another embodiment, this object is achieved by providing a patient interface that includes a fluid delivery conduit configured to deliver a first fluid to at least one nostril of a patient. A nasal interface comprising a pair of nostril interfaces is configured to be inserted into the nostrils of the patient for receiving a second fluid from the patient. The fluid delivery conduit is movable relative to the nostril interface, wherein delivery of the first fluid to the at least one nostril of the patient is controlled by the position of the fluid delivery conduit relative to the nasal interface such that 1) when the fluid delivery conduit is in a first position relative to the nasal interface, the fluid delivery conduit is configured to deliver the first fluid to both nostrils of the patient; and 2) when the fluid delivery conduit is in a second position relative to the nasal interface, the fluid delivery conduit is configured to deliver the first fluid to one of the nostrils of the patient.

In another embodiment, this object is achieved by providing a patient interface that includes a fluid delivery conduit having output openings configured to deliver a first fluid to the nose of a patient. A pair of nostril interfaces is configured to be inserted into the nostrils of the patient for receiving a second fluid from the patient. The fluid delivery conduit is capable of relative movement with respect to the nostril interfaces that adjusts the output openings to generally control a relative amount of the first fluid being directed to the first nostril of the patient in comparison with amount of the first fluid directed to the second nostril of the patient.

In another embodiment, this object is achieved by providing a patient interface that includes an appliance portion including a nostril interface configured to be received by a patient's nostril and to provide fluid communication between the nostril and a fluid path. A physiological function sensor is connected with the appliance portion for engagement with the skin of the nose of the patient and generating a signal based upon a physiological function measurement.

Another aspect of the present invention provides patient interfaces, such as gas sampling cannulas, with selective nostril oxygen delivery, so that the oxygen can be preferentially directed to either or both nostrils.

Another aspect of the present invention provides a patient interface that provides primary and secondary detection of the respiratory condition of the patient.

A further aspect of the present invention provides an apnea monitor in which the primary and secondary detection signals or collected at a single site on the patient.

A further aspect of the present invention provides a single site ambulatory sleep diagnostic sensor that provides measures of effort (such as respiratory effort), $SpO_2$, and flow.

These and other aspect, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 1 is a perspective view of an embodiment of a patient interface for gas sampling, supplemental gas delivery, or combined gas sampling and supplemental gas delivery;

FIG. 2 is a more detailed view of an embodiment of the interface of FIG. 1;

FIG. 3 is a more detailed view of another embodiment of the interface of FIG. 1;

FIG. 9 is a perspective view of another embodiment of a patient interface for gas sampling, supplemental gas delivery, or combined gas sampling and supplemental gas delivery;

FIG. 10 is a more detailed view of one side of the interface of FIG. 9;

FIG. 11 is a more detailed view of the interface of the interface of FIG. 9;

DETAILED DESCRIPTION OF THE EXEMPLARY EMBODIMENTS

Figure 5:
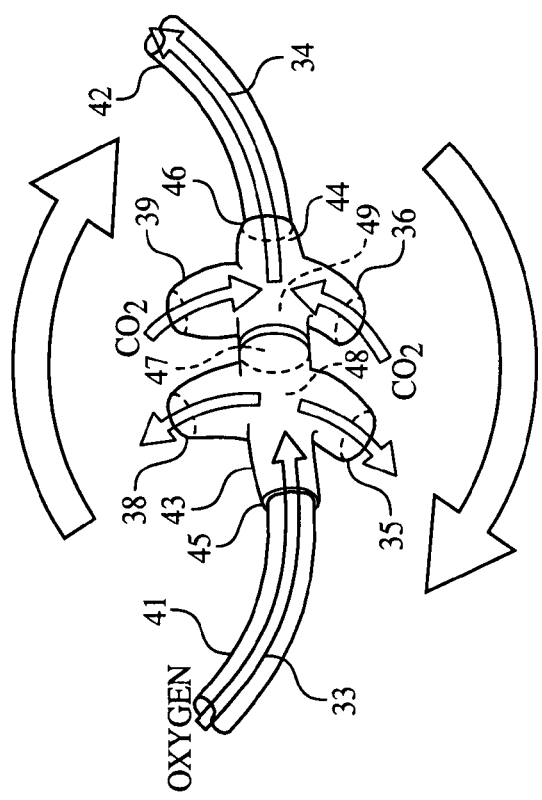
FIG. 5 is a more detailed view of an embodiment of the interface of FIG. 4.

FIG. 1 illustrates a patient interface 10 according to an embodiment of the present invention. Patient interface 10 may be used as a combination oral and nasal gas sampling cannula or "appliance," and/or may also be used as supplemental gas delivery cannula or "appliance." Typically, the sample gas is carbon dioxide ($CO_2$) and/or oxygen ($O_2$) and the supplemental gas is oxygen ($O_2$). However, the present invention contemplates that the sampled gas can be any gas or combination of gas capable of being measured using any existing techniques. The present invention also contemplates that the supplemental gas can be any gas or combination of gas, such as helium, nitrogen, a helium-oxygen mixture (heliox), or a nitrogen-oxygen mixture.

As used herein, the term "patient interface" is intended to refer broadly to any device or structure that interfaces or cooperates with a patient, or has a portion thereof that interfaces or cooperates with a patient. The term "appliance" broadly refers to any device or structure that outputs a fluid to and/or intakes a fluid from a patient. The term "cannula" as used herein refers one type of "appliance" and refers, more specifically, to a structure that has at least a portion thereof that protrudes at least partially into at least one nostril of a patient.

As shown, patient interface 10 includes a body portion 12 configured to communicate with at least one fluid path. In the illustrated embodiment, a first fluid path 14 and a second fluid path 15 are provided by tubing 11 and 16, respectively. The term "tubing" as used herein is intended to refer to a flexible, rigid, or semi-rigid tube. Of course any suitable structure for transporting fluids may be configured to define the fluid paths.

The present invention contemplates that at least one fluid path communicates the sample gas to a suitable device for measurement, such as a gas analyzer, pressure sensor, flow sensor, temperature sensor, humidity sensor, etc. In the case of gas analyzer, the sample gas is transported to the measurement site. In the case of a pressure or flow measurement, the fluid path communicates the gas a suitable pressure or flow sensing device. Other sensors measuring other properties or components of the fluid, such as temperature, humidity, and gas composition, fluid or optical communication with the fluid path are contemplated as well.

In the illustrated embodiment, body portion 12 has a pair of tubing connecting portions 17 and 19 for interfacing and/or connecting with fluid paths 14 and 15, respectively. In one embodiment, connecting portions 17 and 19 comprise respective orifices in body portion 12, which orifices each have an inner diameter configured to form a friction fit with the outer diameter of an associated tubing 11, 16, respectively.

Other mechanisms for forming connections between body portion 12 and the tubing or fluid paths are possible. For example, the connecting portions on body portion 12 may be in the form of projections, each containing a passage therein and having an outer surface with an outer diameter configured to form a friction fit with the inner diameter of an associated one of the tubes, etc. In other embodiments, the connection may be achieved by an adhesive or other joining structure. In another embodiment, the tubing and the body portion may be integrally formed. The disclosed embodiments are not intended to be limiting in any way.

As shown in the embodiment of FIG. 1, tubing 11 and 16 of patient interface 10 are configured to extend from body portion 12 and at least partially around each ear of the patient to hold body portion 12 in a generally stable position relative to the nose of the patient. The routing of tubing 11, 16 around each ear of the patient is only one example of how the body portion may be held in a generally stable position relative to the nose of the patient. For example, in another embodiment, tubing 11, 16 may be routed from body portion 12 over the head of the patient, and secured in a variety of ways known in the art, including but not limited to clips, adhesives, etc. The illustrated embodiment is not intended to be limiting in any way.

Patient interface 10 also includes at least one generally tubular nostril interface 18 that projects from the body portion 12. In the illustrated embodiment, two nostril interfaces 18 and 21 are shown. Although it is contemplated that in some embodiments, only one nostril interface 18 may be provided. Nostril interfaces 18 and 21 are configured to be inserted into an associated nostril of a patient and have respective internal orifices in communication with associated fluid paths 14 and 15, respectively.

As shown in FIG. 2, communication between nostril interface 18 and the orifice of connecting portion 17 is provided by an internal conduit 23 within body portion 12. Similarly, an internal conduit 25 communicates nostril interface 21 with connecting portion 19, as known in the art. This allows fluid paths 14 and 15 to be in fluid communication with the nostrils, so that fluids may either be received from the patient and/or supplied to the patient. In one embodiment, nostril interface 18, connecting portion 17, and fluid path 14 may be configured to supply a fluid that includes oxygen ($O_2$) to the patient from a suitable fluid supply, and nostril interface 21, connecting portion 19, and fluid path 15 may be configured to receive a fluid that includes carbon dioxide ($CO_2$) expired from the patient. In such an embodiment, fluid path 15 communicates the carbon dioxide to a suitable device, such as a gas analyzer, so that the concentration of the carbon dioxide in the expired fluid and/or rate of flow of the expired fluid may be monitored over time. In such an embodiment, an internal wall structure 24 seals internal conduit 23 communicating with nostril interface 18 from internal conduit 25 communicating with nostril interface 21. In one embodiment, this internal wall structure is formed in accordance with the teachings of U.S. Pat. No. 5,335,656, which is hereby incorporated by reference in its entirety.

It should also be appreciated that while fluid path 14, connecting portion 17, and nostril interface 18 are mentioned above in one embodiment as being used for oxygen delivery, while fluid path 15, connecting portion 19, and nostril interface 21 are mentioned as being used for carbon dioxide sampling, these may be reversed depending on which nostril (left or right) is preferred for carbon dioxide sampling versus oxygen delivery.

In another embodiment, nostril interfaces 18, 21 and associated fluid paths 14, 15 all receive a fluid that includes carbon dioxide from the patient. In another embodiment, nostril interfaces 19, 21 and associated fluid paths 14, 15 all deliver oxygen to the patient.

Nostril interface 18 and/or 21 may be in the form of a projection or truncated prong that is constructed and arranged to extend into the nostril. The length of the prong may vary and may depend on the size of the nostrils of the patient. For example, the prong may be shorter for a child patient and longer for an adult patient. In addition, nostril interface 18 and/or 21 may be shaped or angled relative to body portion 12 so as to substantially conform with the nostril, which may make interface 10 more comfortable for the patient to wear.

As shown in FIG. 1, patient interface 10 in one embodiment may also include an oral sampler 20 that is on a side of body portion 12 opposite the nostril interfaces 18, 21 and projects from the body 12 in a direction opposite the nostril interfaces 18, 21. Oral sampler 20 is configured to receive a fluid from the mouth of the patient. Oral sampler 20 has an opening 27, or sampling inlet, that can be positioned near the patient's mouth so that when the patient exhales, oral sampler 20 may communicate a portion of the fluid containing carbon dioxide being exhaled from the patient to the appropriate sampling fluid path leading to the suitable testing device, such as a gas analyzer. Oral sampler 20 may include a collector (not shown) that is configured to direct the expired gases from the patient's mouth to opening 27. Such a collector is shown in FIG. 10 and described in further detail below.

In one embodiment shown in FIG. 3, oral sampler 20 includes an internal passageway or conduit 29 that connects opening 27 in oral sampler 20 with internal conduit 25 leading to connecting portion 19 so that fluid being exhaled by one nostril and the mouth may enter fluid path 15 and be transmitted to the gas analyzer. As illustrated in the embodiment of FIG. 3, internal conduit 23 only communicates fluid path 14 with one of nostril interfaces 18. Internal conduits 23, 25, and 29 should have smooth surfaces and should be sized and shaped so as to minimize gas mixing and maintain the fidelity of the gas waveform.

In an embodiment, oral sampler 20 is configured to be adjustable relative to body portion 12 so that opening 27 in oral sampler 20 may be optimally positioned relative to the patient's mouth to account for differences in anatomy as well as flow direction from the patient's oral cavity, i.e. mouth. The adjustability may be provided to oral sampler 20 with suitable materials and/or structures. For example, in one embodiment, oral sampler 20 may be made from a flexible material, such as a polymer or elastomeric material, that has an internal malleable material, such as a metal wire 31, so that opening 27 may be moved to and retained at the desired position relative to the patient's mouth. The wire may be embedded in the flexible material, or the wire may be attached to the flexible material on an outside surface thereof, as described in greater detail in another embodiment below, which is hereby incorporated by reference.

Adjustability may also be provided by a bellows or accordion-like structure in oral sampler 20, as described in greater detail in another embodiment below, which is hereby incorporated by reference. In one embodiment, oral sampler 20 may be adjusted so that it is inoperative, i.e., unable to communicate the fluid being exhaled from patient through the mouth. This may be done by either positioning opening 27 to a location that will not receive the fluid being exhaled by the patient, or in another embodiment, it may be done by crimping oral sampler 20 so that passageway 29 is pinched off. In yet another embodiment, a separate or tethered plug or seal structure may be inserted into or covered over opening 27 to prevent exhaled fluid from entering opening 27.

In the embodiment of FIGS. 1-3, patient interface 10 also includes a pair flexible stabilizers 22 or wings that extend laterally outwardly from body portion 12 on opposite sides of body portion 12, as shown in FIG. 1. Specifically, each stabilizer 22 extends laterally outwardly from an associated one of connecting portions 17, 19. As shown, each stabilizer 22 has a concave-convex cross-section forming a portion of a tubular configuration, and transitions into a complete tubular configuration that forms the connecting portions 17, 19. Stabilizers 22 are made from a sufficiently low durometer material to substantially conform to the patient's adjacent facial surface when interface 10 is mounted to the patient. Stabilizers 22 extend away from body portion 12 and provide an ergonomic configuration to enhance patient comfort. In addition, stabilizers 22 are sized to work in tandem with fluid paths 14, 15 to hold the nostril interfaces 18, 21 in a substantially stable position. Fluid paths 14, 15 may be positioned across stabilizers 22 and apply supportive force to the stabilizers when interface 10 is mounted to the user.

In an exemplary embodiment, interface 10 is manufactured from a soft (low durometer) material for a more comfortable fit for the patient. For example, the material of the interface may have a Shore A hardness of about 10 to about 40, and may be manufactured, for example, from a polyurethane or a silicone. In one embodiment, body portion 12, stabilizers 22, nostril interfaces 18, 21, and oral sampler 20 are molded from the same material. In another embodiment, body portion 12 and stabilizers 22 are molded from the same material, while nostril interfaces 18, 21 and oral sampler 20 are molded from a different material.

As indicated above, interface 10 illustrated in FIG. 1 may be used as a combination oral and nasal carbon dioxide sampling device, and/or may also be used as an oxygen delivery device. Depending on how fluid paths 14, 15 and internal conduits 23, 25 are configured, interface 10 may be configured to provide carbon dioxide sampling from one nostril interface and oxygen delivery to the other nostril interface, or both nostril interfaces may be used for carbon dioxide sampling. In an embodiment, the nostril interfaces may be configured to provide carbon dioxide sampling from as well as oxygen delivery to both nostrils.

It should be appreciated that the features of interface 10 discussed above may also be used in the embodiments of the patient interfaces discussed below. Thus, the features and attributes discussed above are hereby incorporated by reference into each of the other embodiments discussed below.

Figure 4:
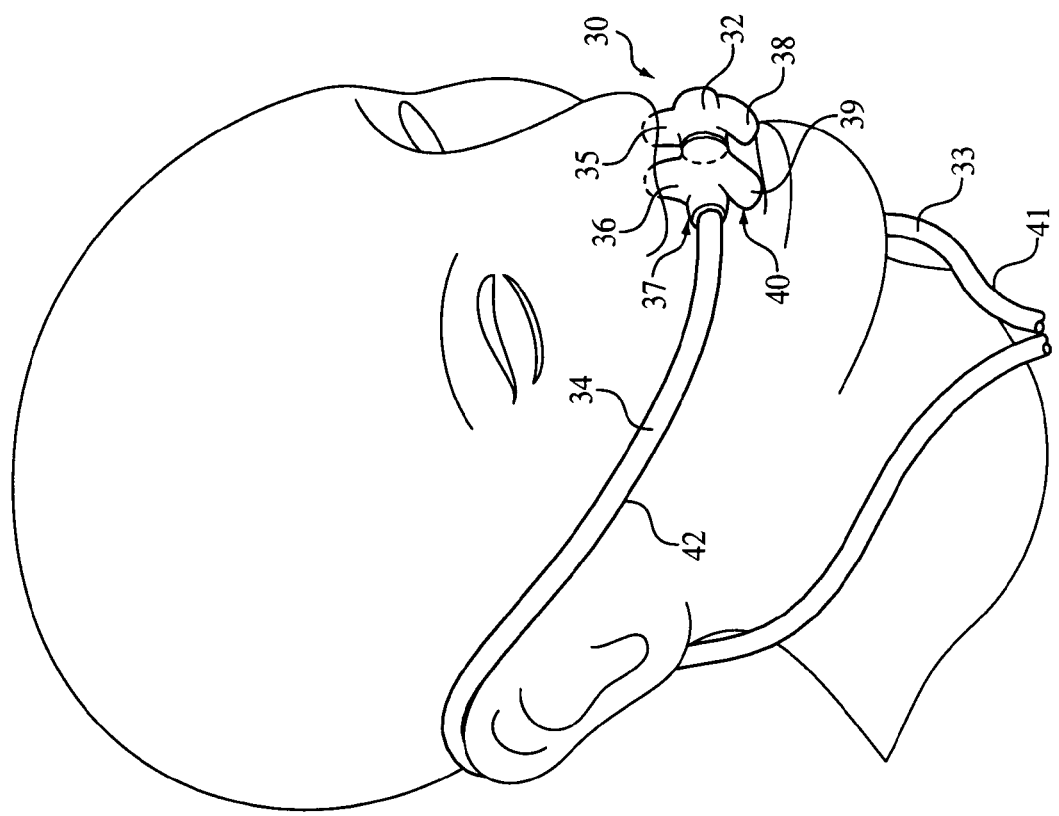
FIG. 4 is a perspective view of another embodiment a patient interface for gas sampling, supplemental gas delivery, or combined gas sampling and supplemental gas delivery.

FIG. 4 illustrates a patient interface 30 according to a further embodiment of the invention. Interface 30 includes a body portion 32 that is configured to communicate with a first fluid path 33 and a second fluid path 34. A first nostril interface 35 and a second nostril interface 36 extend from a first side 37 of body portion 32 and are configured to be inserted into the nostrils of the patient when the body portion is in a first orientation (shown in FIG. 4). First nostril interface 35 communicates with the first fluid path 33 and the second nostril interface communicates with second fluid path 34. Interface 30 also includes a third nostril interface 38 and a fourth nostril interface 39 that extend from a second side 40 of body portion 32. The third nostril interface also communicates with first fluid path 33, and fourth nostril interface 39 communicates with second fluid path 34. Third nostril interface 38 and fourth nostril interface 39 are configured to be inserted into the nostrils of the patient when body portion 32 is in a second orientation, which is an orientation that is 180° from the first orientation of FIG. 4, and shown in FIG. 5.

Specifically, when interface 30 is in the first orientation, first nostril interface 35 is configured to be inserted into the left nostril of the patient, and second nostril interface 36 is configured to be inserted into the right nostril of the patient, so as to communicate first fluid path 33 with the left nostril and second fluid path 34 with the right nostril. Conversely, when interface 30 is in the second orientation, shown in FIG. 5, third nostril interface 38 is configured to be inserted into the right nostril, and fourth nostril interface 39 is configured to be inserted into the left nostril, so as to communicate first fluid path 33 with the right nostril, and second fluid path 34 with the left nostril.

As shown, interface 30 is symmetrically configured so that it may be used when body portion 32 is either in the first or second orientation. When body portion 32 is in the first orientation, third nostril interface 38 and fourth nostril interface 39 are configured to be positioned near the patient's mouth so as to communicate first fluid path 33 and second fluid path 34 with the patient's oral cavity. Conversely, when body portion 32 is in the second orientation, first nostril interface 35 and second nostril interface 36 are configured to be positioned near the patient's mouth so as to communicate second fluid path 34 and first fluid path 33 with the patient's oral cavity.

In an exemplary embodiment, as shown in FIG. 5, all of the nostril interfaces 35, 36, 38, 39 may be angled relative to body portion 32 so as to allow nostril interfaces 35, 36, 38, 39 to conform to the nostrils for a more comfortable fit on the patient, as well as be directed towards the patient's mouth when in the respective orientation. In addition, body portion 32 may be provided with a slightly concave surface on a side thereof as it extends laterally for engaging the surface area of skin beneath the patient's nose. This concave surface engages the surface area of skin beneath the patient's nose irrespective of whether body portion 32 is in the first or second orientation, and provides a comfortable engagement with the patient.

As shown in FIG. 5, first fluid path 33 and second fluid path 34 are defined by tubing 41, 42, respectively, each of which are received by body portion 32 on opposite ends of the body portion at a first connecting portion 43 and a second connecting portion 44, respectively. As shown, first connecting portion 43 includes an orifice 45 that is configured to receive tubing 41. The diameter of orifice 45 may be equal to or slightly less than the outer diameter of tubing 41 so that a seal may be formed between body portion 32 and tubing 41. Likewise, second connecting portion 44 includes an orifice 46 that is configured to receive tubing 42 in a similar manner. Like the embodiment illustrated in FIG. 1, tubing 41, 42 may be flexible enough to extend from body portion 32 and at least partially around each ear of the patient to hold body portion 32 in a fixed position relative to the patient's nose. The fixed position may be the first orientation, in which first nostril interface 35 and second nostril interface 36 are positioned in the nostrils, or the fixed position may be the second orientation, in which third nostril interface 38 and fourth nostril interface 39 are positioned in the nostrils.

As illustrated in FIG. 5, and as can be appreciated from the discussion relating to the embodiment of FIG. 1, body portion 32 may include a separator or seal 47 that separates a first conduit 48, or passageway, from a second conduit 49, or passageway within the body portion 32. First conduit 48 is configured to communicate a fluid between first nostril interface 35, third nostril interface 38, and first connecting portion 43, and second conduit 49 is configured to communicate a fluid between second nostril interface 36, fourth nostril interface 39, and second connecting portion 44.

In one exemplary embodiment, first fluid path 33 and second fluid path 34 are both configured to communicate a fluid containing carbon dioxide that is being exhaled by the patient to a suitable testing device, such as a gas analyzer. That is, all four nostril interfaces 35, 35, 38, 39 may be configured to communicate carbon dioxide from the patient (via the mouth and the nose) to first and second fluid paths 33 and 34. In another embodiment, first fluid path 33 and nostril interfaces 35, 38 are configured to communicate the fluid being exhaled by the patient to the gas analyzer, while second fluid path 34 and nostril interfaces 36, 39 are configured to supply oxygen to the patient for inhalation. Because the flow from the patient's nostrils is usually not equal and often dramatically different (sometimes greater than an order of magnitude difference), a symmetrical design would allow the interface 30 to be "flipped," thereby permitting carbon dioxide sampling from either of the patient's nostrils and oxygen delivery to other nostril.

In yet another embodiment, first fluid path 33 and second fluid path 34, and all four nostril interfaces 35, 36, 38, 39 are configured to communicate oxygen to the patient for inhalation.

Figure 6:
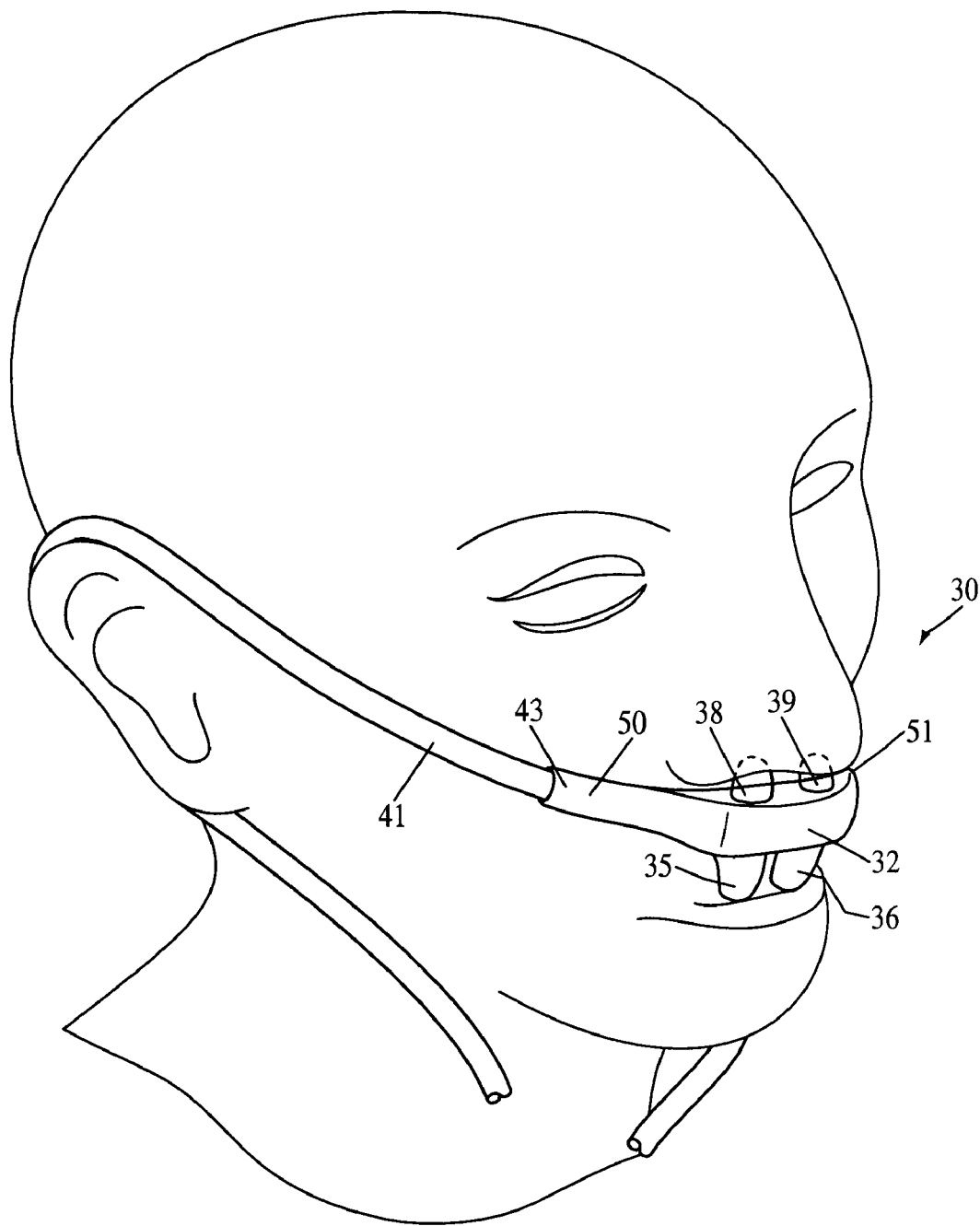
FIG. 6 is a perspective view of another embodiment of the interface of FIG. 4

In an embodiment, as shown in FIG. 6, which is a modified version of patient interface 30 of FIG. 5, patient interface 30 also includes a first flexible stabilizer 50 and a second flexible stabilizer 51 that take the form of tubular portions extending from body portion 32 on opposite sides of the body portion. Although not fully shown, second stabilizer 51 is of the same design as first stabilizer 50. Like the stabilizers shown and discussed above with respect to the embodiment illustrated in FIG. 1, stabilizers 50, 51 may be configured to substantially conform to the patient's face when the interface 30 is mounted to the patient.

In the illustrated exemplary embodiment, stabilizers 50, 51 have a substantially closed tubular cross-sectional configuration. In addition, first connecting portion 43 is part of first stabilizer 50 and is located at a distal end of the first stabilizer, and second connecting portion 44 is part of second stabilizer 51 and is located at a distal end of the stabilizer. Tubing 41, 42 is configured to connect to the respective connecting portion 43, 44, and extend from each of stabilizers 50, 51 and at least partially around each ear of the patient to hold body portion 32 in a fixed position relative to the nose.

Figure 7:
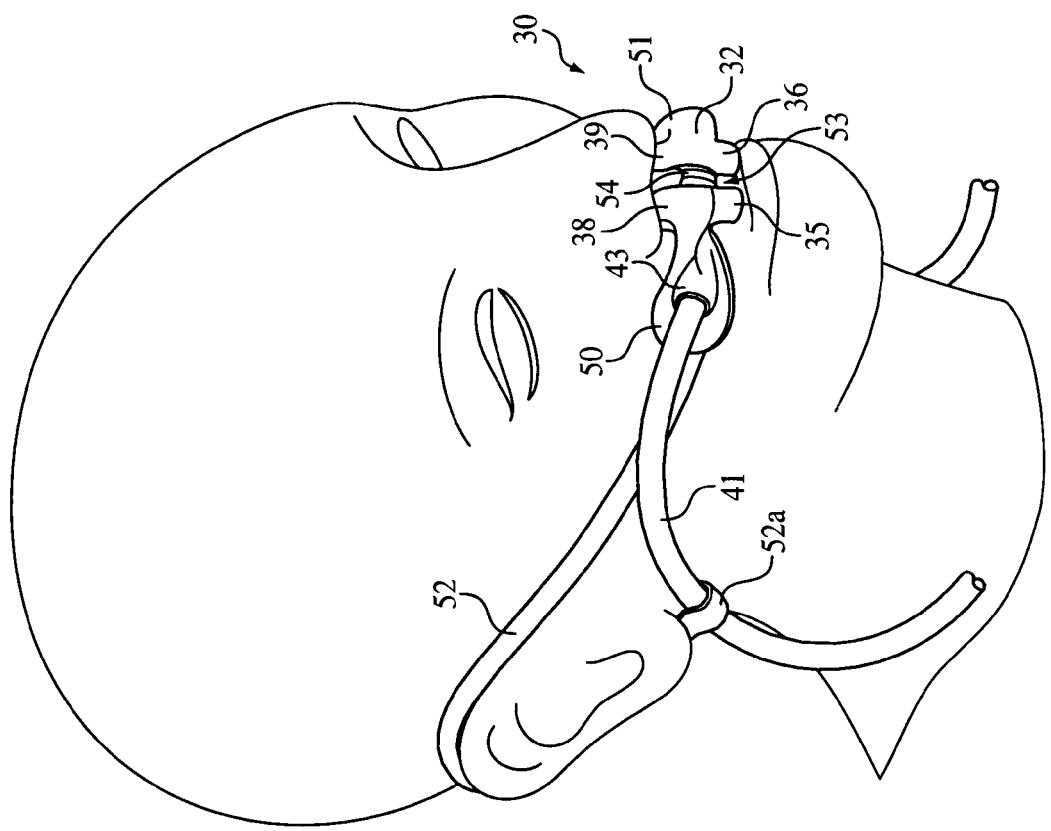
FIG. 7 is a perspective view of another embodiment of the interface of FIG. 4.

FIG. 7 illustrates another embodiment of patient interface 30 of FIG. 6. As shown, connecting stabilizers 50, 51 (51 being of the same design as 50) have a similar function and purpose as stabilizers 22 shown in FIGS. 1-3. As shown, stabilizers 50, 51 each have a flattened configuration that widens into a rounded distal end portion so as to form a generally teardrop shape. First connecting portion 43 is located at an intermediate section of first stabilizer 50, as illustrated in FIG. 7, and second connecting portion 44 is located at an intermediate section of second stabilizer 51 (not shown).

Patient interface 30 also includes a modified structure for mounting the patient interface to the head of the patient. Specifically, in this embodiment, patient interface 30 incorporates a head mount or headgear that includes a first strap 52 connected to first stabilizer 50 at the distal end of first stabilizer, and a second strap (not shown) connected to second stabilizer 51 at the distal end thereof. For illustrative purposes, only first strap 52 will be discussed, although it should be appreciated that the same would apply to the second strap as well.

Strap 52 is configured to extend from first stabilizer 50 and at least partially around the ear of the patient to hold body portion 32 in a stable or fixed position relative to the patient's nose. As shown in FIG. 7, in this embodiment, strap 52 has a closed loop 52a at a distal end thereof. Closed loop 52a is dimensioned to have an inner diameter of substantially the same dimension as the outer diameter of the tubing 41. Tubing 41 extends from first stabilizer 50, and strap 52 is configured to receive tubing 41 so as to guide the tubing from stabilizer 50 and away from the patient. While in the illustrated embodiment tubing 41 is received by strap 52 at a distal end thereof, such a configuration is not intended to be limiting in any way. For example, tubing 41 may be received by strap 52 at an intermediate portion thereof.

In an embodiment, body portion 32 may also include an adjustor 53 located between first nostril interface 35 and second nostril interface 36, as well as between third nostril interface 38 and fourth nostril interface 39, as shown in FIG. 7. Adjustor 53 is configured to adjust a position of first nostril interface 35 relative to second nostril interface 36 and a position of third nostril interface 38 relative to fourth nostril interface 39. In an embodiment, adjustor 53 is a flexible section of the body portion 32. In one embodiment, the flexible section may comprise bellows 54, or any other accordion-like structure that allows body section 32 to lengthen, shorten, or bend, and retain the lengthened, shortened, or bent configuration. Such accordion or bellows structures are known, for example, from commonly available plastic drinking straws. Adjustor 53 allows for patient interface 30 to be adjusted for the anatomic variations seen between different aged and sized subjects, thereby providing a more comfortable fit for a larger population of patients.

Figure 8:
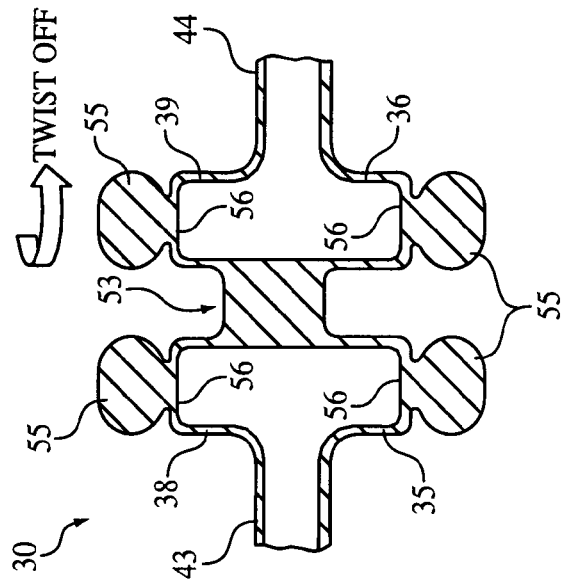
FIG. 8 is a detailed view of another embodiment of the interface of FIG. 7.

As shown in FIG. 8, patient interface 30 may also include at least one seal or plug structure 55 configured to block fluid communication with (i.e., to and from) at least one of nostril interfaces 35, 36, 38, 39. Seal structure 55 may be a plug that is received by an orifice 56 of any one of nostril interfaces 35, 36, 38, 39, or seal structure 55 may be a cap that frictionally engages an outside surface of any one of the nostril interfaces, or vice-versa. It is also contemplated that the cap may be of a twist-off design that has threads on an inner surface thereof that match threads on the outside surface of the nostril interface. In the illustrated embodiment, one seal structure 55 is connected to each nostril interface 35, 36, 38, 39 so as to block fluid communication with all of the nostril interfaces. In one embodiment, the four seal structures 55 blocking each nostril interface 35, 36, 38, 39 may be integrally molded with the associated nostril interface and may be selectively broken, cut, or snapped off by the clinician, as desired. Of course, the clinician may block fluid communication with different combinations of nostril interfaces 35, 36, 38, 39, or none at all. It is contemplated that any other suitable seal structure for sealing off a nostril interface may be used. The illustrated embodiment is not intended to be limiting in any way.

In one embodiment, for example, where nostril interface 35 delivers oxygen to one nostril and nostril interface 36 receives carbon dioxide from the other nostril, nostril interface 39 may remain open to function as an oral sampling port, while nostril interface 38 may be sealed by seal structure 55. This may be done to increase the amount of oxygen delivered to the nostril through nostril interface 35 in comparison with a configuration in which nostril interface 38 is left unsealed.

FIG. 9 illustrates a patient interface 60 that includes an oral and nasal cannula or appliance that is configured to sample gas, such as carbon dioxide, and/or supply gas, such as oxygen, to the patient. As shown, patient interface 60 includes a body portion 62 that is configured to receive a first fluid path 61 and a second fluid path 63. A first nostril interface 64 and a second nostril interface 65 project from a top surface 66 of the body portion 62. Nostril interfaces 64, 65 are configured to be aligned with the patient's nostrils when patient interface 60 is mounted on the patient. Nostril interfaces 64, 65 provide fluid communication between the nostrils and associated fluid paths 61, 63.

Top surface 66 of body portion 62 is configured to have a slightly concave surface so as to provide a gap between the top surface 66 and the lower skin between the nostrils so that the patient's nostrils are not sealed by body portion 62, but rather allows fluid communication between the nostrils and the atmosphere outside of the patient interface 60 with minimum restriction of the flow in and out of the nostrils.

Although nostril interfaces 64, 65 are illustrated as "stubs," it is also contemplated that in other embodiments, the nostril interfaces may be longer and shaped to follow the natural curvature of the interior of the nostril, as shown and described in other embodiments herein. The illustrated embodiment is not intended to be limiting in any way.

As illustrated, patient interface 60 also includes an oral sampler portion 67 that is operatively joined to the body portion 62 and extends from body portion 62 in a direction away from nostril interfaces 64, 65. Oral sampler portion 67 has an orifice 68 that is configured to communicate with at least one of fluid paths 61, 63. Orifice 68 is configured to receive a fluid being exhaled from the oral cavity through the mouth of the patient or, in a different embodiment, to deliver a fluid, such as oxygen, for the patient to inhale.

As illustrated in FIG. 10, oral sampler portion 67 includes a collector 80 on a distal end thereof that is configured to direct the expired gases from the patient's mouth to orifice 68. Collector 80 may be shaped as a scoop or any other shape that would direct the flow in a smooth manner, while minimally disturbing and mixing the flow. In the illustrated embodiment, collector 80 includes a concave surface 81 that is shaped so as to generally direct the flow of expired gases that engage surface 81 towards opening 68. The illustrated embodiment is not intended to be limiting in any way.

Oral sampler portion 67 is formed from a malleable structure that enables an orientation of orifice 68 of oral sampler portion 67 to be changed and retained in different positions. In other words, oral sampler portion 67 may be configured to be adjustable relative to the mouth of the patient. In an embodiment, oral sampler portion 67 includes at least one malleable wire 70 that is configured to provide adjustability to the shape of the oral sampler portion. By bending wire 70, orifice 68 in the oral sampler portion 67 may be moved relative to body portion 62, retain the adjusted position, to position the oral sampler portion as desired relative to the mouth of the patient when patient interface 60 is mounted to the patient. In an exemplary embodiment, wire 70 generally retains the shape to which it is bent, and may be embedded in oral sampler portion 67. In another embodiment, two malleable wires 70 and 71 may be disposed on opposing outside surfaces 72a, 72b of oral sampler portion 67, respectively, as shown in FIGS. 10 and 11.

In a further exemplary embodiment, body portion 62, nostril interfaces 64, 65, and oral sampler portion 67 are molded from a single piece of material. The material may be any suitable material that fully complies with the applicable regulations for such interface devices. For example, patient interface 60 may be molded from soft biocompatible materials, such as polyurethanes and silicones.

Fluid paths 61, 63 may be defined by suitable tubing 73, 74, respectively, that extends from body portion 62 and at least partially around each ear of the patient to hold the body portion in a fixed position relative to the nose of the patient. "Suitable" tubing is defined as tubing that complies with the applicable regulations for interface devices. Tubing 73, 74 should be sized such that kinks that would impede flow of the fluids in fluid paths 61, 63 are difficult to form. Tubing 73, 74 may be connected to the body portion 62 in any manner as described above.

Also shown in FIG. 9 is an adjustor 75 for adjusting or controlling the tension provided to tubing 73, 74 and body portion 62 so body portion 62 will stay in a fixed position relative to the patient's nose. As illustrated, adjustor 75 is in the form of an adjustable slide and is configured to slidingly receive tubing 73, 74 coming from each ear at a position below the chin of the patient. Adjustor 75 includes two passages 76, 77 that are configured to provide a frictional interface with the tubing 73, 74, respectively, so as to provide frictional resistance when the adjustor is slid relative to tubing 73, 74. Of course, other configurations of adjustors may be used. The illustrated embodiment is not intended to be limiting in any way.

Figure 12:
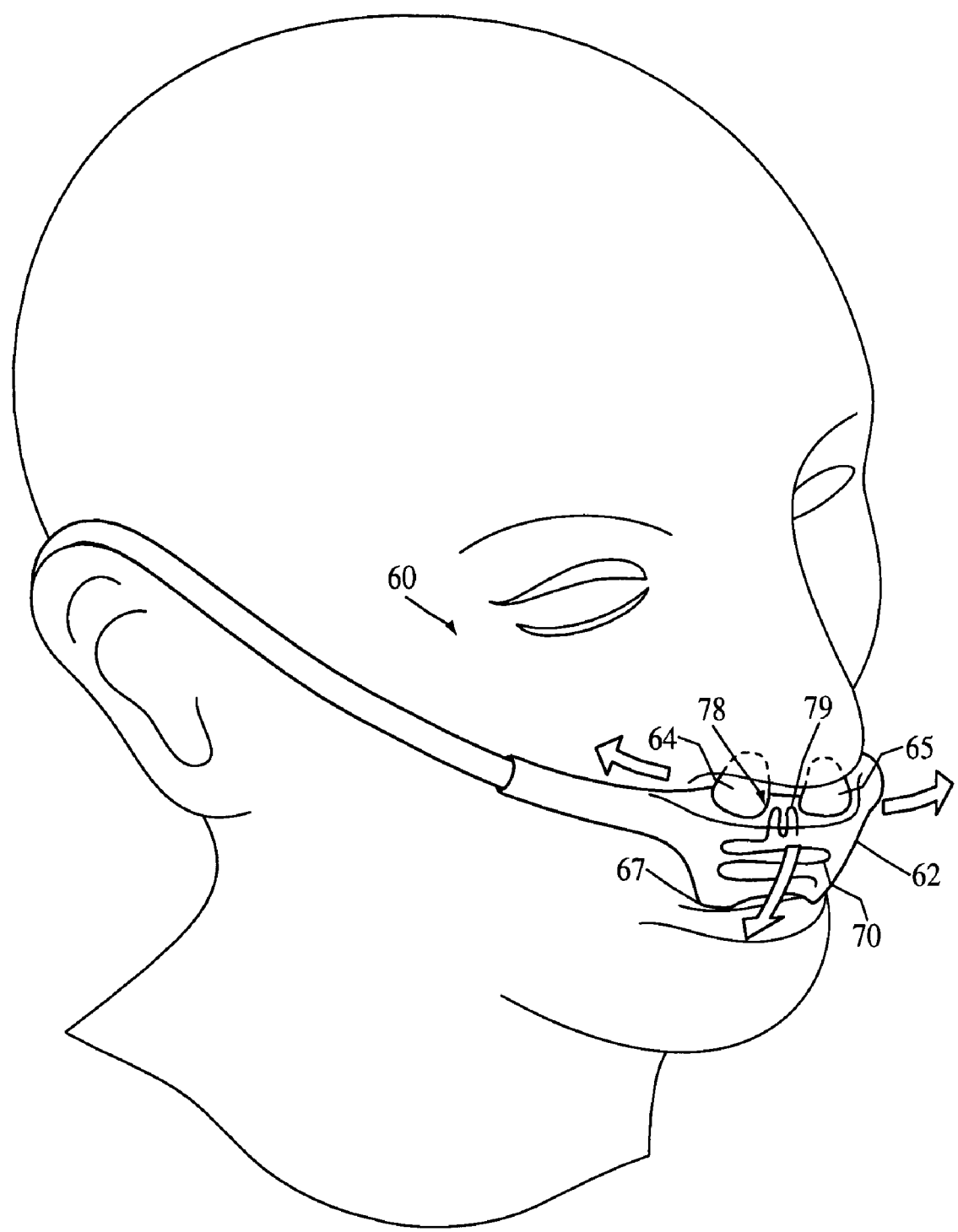
FIG. 12 is a perspective view of another embodiment of the interface of FIG. 9.

As shown in FIG. 12, body portion 62 may also include a malleable structure 78 that interconnects nostril interfaces 64, 65 to enable a distance between the nostril interfaces to be adjustable. In an embodiment, malleable structure 78 includes a malleable wire 79. Wire 79 may be constructed and arranged in a bellows-like structure, wherein the wire is bent in a serpentine-like pattern, as illustrated in FIG. 12. In an embodiment, wire 79 may be an extension of wire 70 that is part of the sampler portion 68, as shown in FIG. 12. Wire 79 may be embedded in body portion 62, or may be connected to body portion 62 on an outside surface of the body portion. Of course any suitable malleable structure may be used to provide the adjustability to the distance between the nostril interfaces 64, 65. By providing malleable structure 78 to the body portion 62, patient interface 60 may be adjusted for the anatomic variations seen between different aged and sized subjects, thereby providing a more comfortable fit for a large population of patients. The illustrated embodiment is not intended to be limiting in any way.

Figure 14:
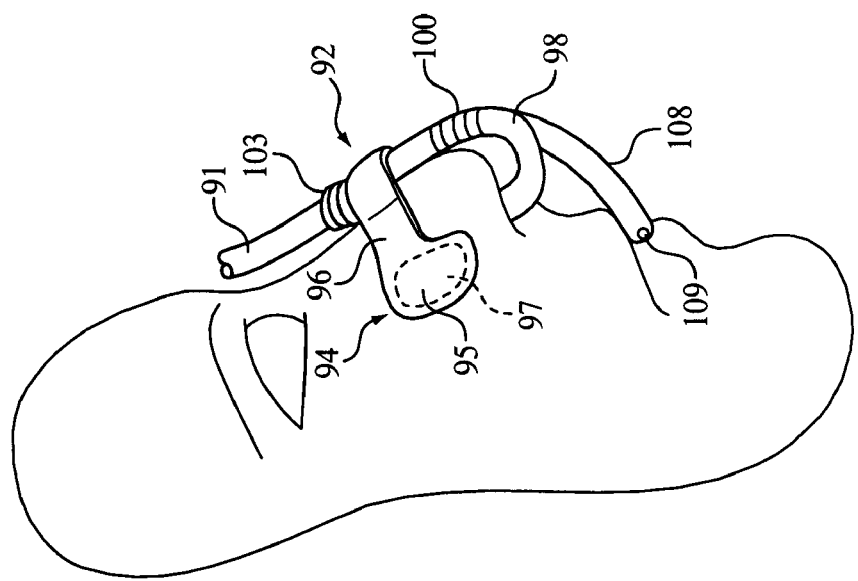
FIG. 14 is a side view of the interface of FIG. 13.
Figure 13:
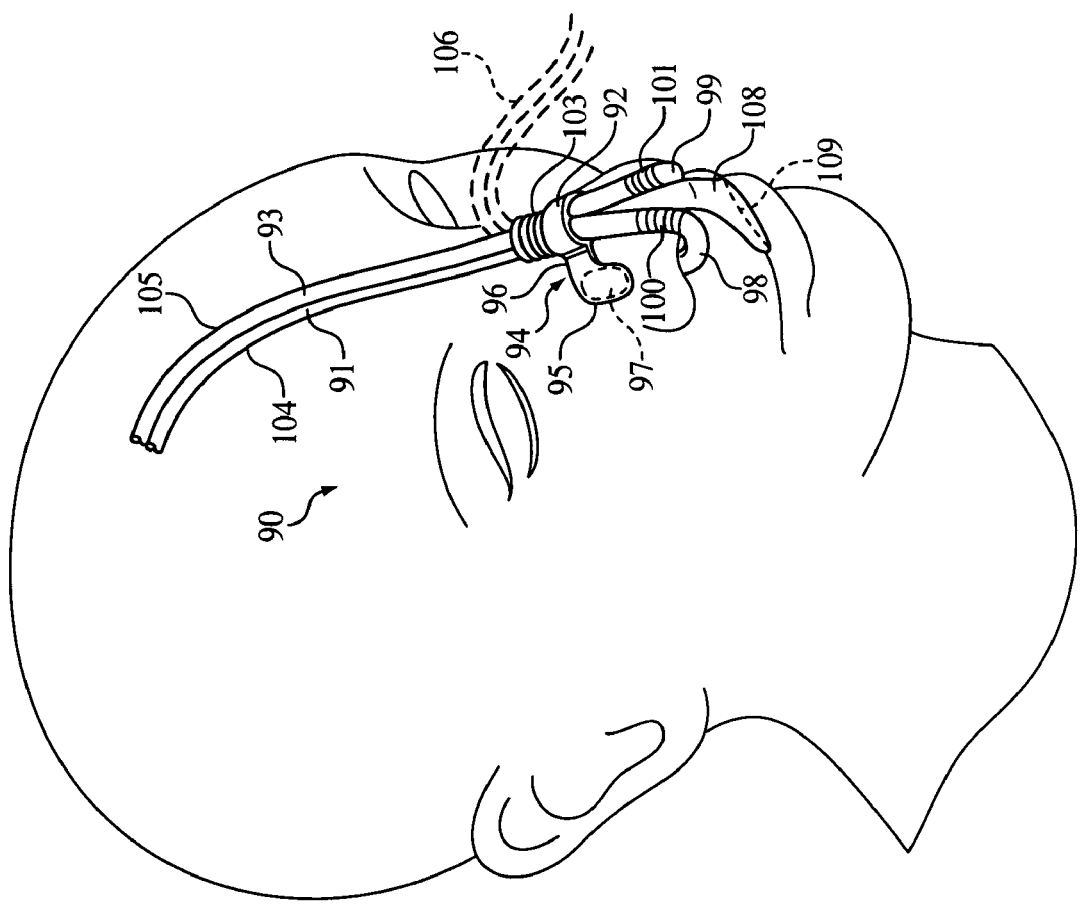
FIG. 13 is a perspective view of another embodiment of a patient interface for gas sampling, supplemental gas delivery, or combined gas sampling and supplemental gas delivery.

FIGS. 13 and 14 illustrate another embodiment of a patient interface 90 according to the principles of the present invention. Interface 90 may be an oral and nasal gas sampling and/or gas delivery cannula or appliance. It is contemplated that this embodiment of patient interface 90 may be particularly applicable for emergency medicine, as well as applications that include procedural sedation. Patient interface 90 includes a body portion 92 configured to communicate with at least one fluid path. In the embodiment shown, body portion 92 communicates with two fluid paths 91, 93, and an attachment device 94 is constructed and arranged to attach body portion 92 to the nose of the patient. Attachment device 94 includes a nose engaging portion 95 connected with body portion 92 for engaging an external surface of the nose, as shown in FIG. 13.

Nose engaging portion 95 may include a spring clip 96 that is constructed and arranged to engage opposite sides of the patient's nose. More specifically, the spring clip 96 may have a U-shaped configuration that is configured to engage the bridge of the patient's nose, as shown in FIG. 13. The legs of the U-shaped configuration can be separated to receive the bridge of the nose and be gently biased toward one another to grasp the nose therebetween. Attachment device 94 may additionally, or alternatively, include an adhesive 97 that is configured to be removably attached to the patient's nose to assist in securing patient interface 90 to the patient. Adhesive 97 may be any suitable adhesive that will firmly hold attachment device 94 in place on the patient's nose, yet be easily removed upon application of suitable pressure. In an embodiment, adhesive 97 is located on spring clip 96 at portions of the spring clip that engage the patient's nose.

As shown in FIG. 13, two adjustable nostril interfaces 98, 99 are operatively connected to body portion 92. Each nostril interface 98, 99 is configured to be received by a nostril of the patient's nose and to be in communication with fluid paths 91, 93. Nostril interfaces 98, 99 each incorporate a malleable structure 100, 101, respectively, that enables the length and/or orientation of nostril interfaces 98, 99 to be adjustable relative to body portion 92. In the illustrated embodiment, which should not be considered to be limiting in any way, malleable structures 100, 101 include a bellows-like structure, similar to a flexible drinking straw, as mentioned previously. In another embodiment, the nostril interfaces may be a malleable tube or tubing that may be held in place once the nostril interface is inserted in the one of the patient's nostrils.

Body portion 92 is configured to be in communication with at least one of the fluid paths 91, 93 via a junction 103. Junction 103 may be a malleable portion of body portion 92 or may be a malleable structure that is connected to body portion 92 at one end thereof. Fluid paths 91, 93 are defined by tubing 104, 105, respectively. One end of each tubing 104, 105 is received by junction 103, and the other end of each tubing 104, 105 may be connected to a fluid supplier or a fluid receiver. For example, one of fluid paths 91, 93 may communicate oxygen to one of the nostrils via the respective tubing 104, 105 and nostril interface 98, 99, and other one of the fluid paths 91, 93 may communicate a fluid from one of the nostrils via the respective tubing 104, 105 and nostril interface 98, 99. As may be appreciated in view of the description of other embodiments, patient interface 90 may be configured to be a sampling only, or a delivery only, or a combination sampling and delivery patient interface.

Junction 103 is configured to provide an adjustment of the position of tubing 104, 105 relative to body portion 92 for improved tubing management. For example, EMT's in an ambulance may want to route the tubing upwards and over the head, as illustrated. In other situations, the clinician may want to route the tubing to the side of the patient's head, as shown by dashed lines 106 in FIG. 13.

In an embodiment, patient interface 90 also may include an oral sampler 108 that is operatively connected to body portion 92 and is configured to communicate with at least one of fluid paths 91, 93. Oral sampler 108 includes an orifice 109 configured to sample a fluid exhaled from the patient's mouth and/or supply oxygen to the patient mouth so that the patient may inhale the oxygen. In an embodiment, oral sampler 108 may include a malleable structure that allows for adjustment of the position of orifice 109 relative to the mouth of the patient. The malleable structure may include any of the structures discussed herein, such as malleable wires, bellows, etc., may be incorporated into oral sampler 108 to provide the adjustability.

Figure 15:
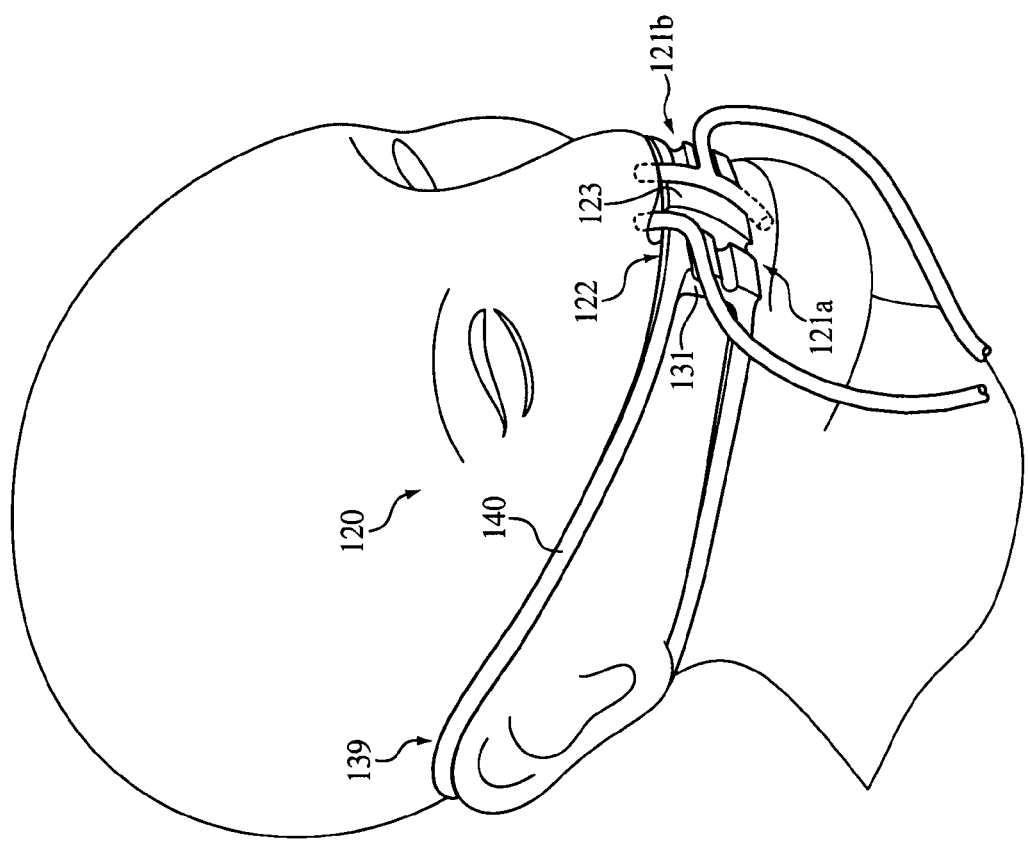
FIG. 15 is a perspective view of another embodiment of a patient interface for gas sampling, supplemental gas delivery, or combined gas sampling and supplemental gas delivery.

FIG. 15 shows an embodiment of a patient interface 120 that may be used as an oral and nasal gas sampling and/or gas delivery cannula or appliance. As illustrated, patient interface 120 includes a body portion 122 that includes a tubing holder portion 123. In one embodiment, tubing holder portion 123 includes two networks of grooves 121a, 121b that each includes a plurality of branches, although in an embodiment, only one groove that includes a plurality of branches may be provided. Grooves 121a, 121b are configured to receive tubing sections 124, 125, respectively, as shown in greater detail in FIG. 16. Each tubing section 124, 125 defines a fluid path 126, 127, respectively, and each fluid path 126, 127 is configured to communicate a fluid either being exhaled by the patient or inhaled by the patient, depending on the specific application, as can be appreciated from the previous discussion.

Tubing 124 has an orifice 128 at one end thereof, which coincides with one end of fluid path 126. Tubing holder portion 123 is constructed and arranged to secure a portion 129 of tubing 124 that is spaced from orifice 128 for positioning the orifice to communicate fluid path 126 with the patient, as shown in FIG. 15. Tubing 124 may be either permanently affixed to tubing holder portion 123, or may be removably received by the tubing holder portion so that they it may be removed from the tubing holder portion without damaging body portion 122. Groove 121a may be shaped and sized to complement the size of tubing 124. For example, groove 121a may have a surface that is defined be a radius that is substantially the same as or slightly less that the outer radius of tubing 124, so that tubing 124 may be frictionally fit with groove 121a without crimping the tubing.

Figure 16:
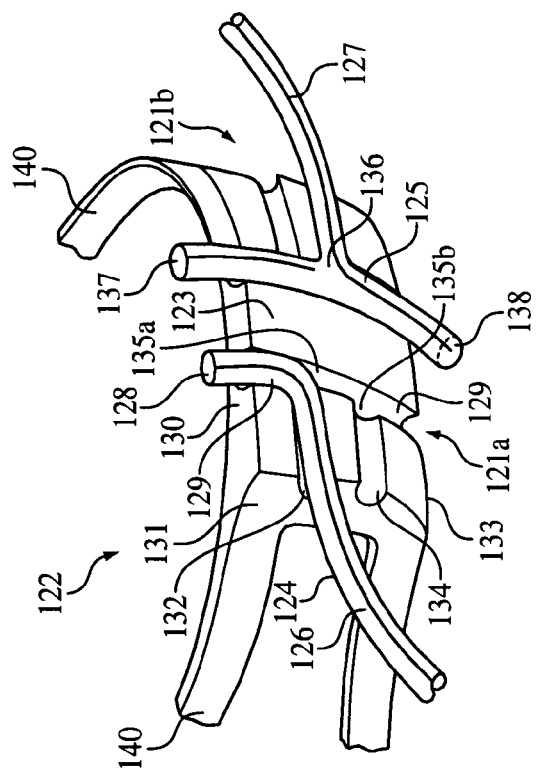
FIG. 16 is a more detailed view of the interface of FIG. 15.

As shown in FIG. 16, a vertical branch 129 of groove 121a extends from a top surface 130 to a bottom surface 133 of tubing holder portion 123. Top surface 130 of tubing holder portion 123 is located near the patient's nose, and bottom surface 133 is located near the patient's mouth when patient interface 120 is mounted to the patient. A first horizontal branch 132 of groove 121a intersects vertical branch 129 at a junction 135a and extends to a lateral side surface 131 of tubing holder portion 123. A second horizontal branch 134 of groove 121a intersects vertical branch 129 at a second junction 135b and also extends to the lateral side surface 131 of the tubing holder portion 123. In the illustrated embodiment, fluid path 126 may be routed from top surface 130 to side surface 121a of tubing holder portion 123 and away from the patient by inserting tubing 124 into a top portion of vertical branch 129, junction 135a, and first horizontal branch 132. Of course, other configurations are possible. For example, in one embodiment, tubing 124 may be inserted into top and middle portions of vertical branch 129, junction 135b, and second horizontal branch 134, which would allow for an adjustment of the distance between top surface 120 and orifice 128 of tubing 124, i.e., how far tubing 134 is inserted into the patient's nostril.

The illustrated embodiment provides a symmetrical design relative to a central, substantially horizontal axis when body portion 122 is mounted to the patient and the patient's head is in a normal, upright position relative to horizontal. Of course, groove 121a may have other configurations. In the illustrated embodiment, groove 121b has a symmetrical configuration relative to a central, substantially vertical axis when body portion 122 is mounted to the patient and the patient's head is in a normal, upright position relative to horizontal. Therefore, details of the branches and the junctions of groove 121b will not be discussed in greater detail herein, and common reference characters are used with the common features of groove 121a. The illustrated embodiment is not intended to be limiting in any way.

Tubing 125 may include a T-shaped junction 136 that is configured to be received by one of grooves 121a, 121b. As illustrated, groove 121b is constructed and arranged to secure T-shaped junction 136, as well as portions of tubing 125 that extend from the T-shaped junction 136. T-shaped junction 136 in tubing 125 allows one orifice 137 of the tubing to be positioned to communicate fluid path 127 with the patient's nostril, and another orifice 138 of tubing 125 to be positioned to communicate fluid path 127 with the patient's mouth, as shown in FIG. 15. Tubing 125 may typically be used for carbon dioxide sampling, but may also be used for oxygen delivery purposes.

It should be appreciated that the embodiment illustrated in FIGS. 15 and 16 allows for patient interface 120 to be configured for the specific needs of the patient. For example, if the patient' left nostril is partially obstructed, thereby making the right nostril more suitable for receiving oxygen, tubing 124 may be inserted into groove 121b and oxygen may be supplied through tubing 124 and orifice 128 to the left nostril via fluid path 126. In addition, tubing 125 may be inserted in groove 121a so that carbon dioxide may be sampled from the patient's partially obstructed right nostril as well as the mouth. Also, one tubing may be inserted into either groove 121a, 121b and the other groove may be left empty. It is also contemplated that multi-lumen tubing may be inserted in either groove 121*a*, 121*b* so that oxygen may be delivered and carbon dioxide may be sampled from the same nostril.

Patient interface 120 also includes a mounting structure 139 for mounting body portion 122 to the head of the patient. As illustrated, mounting structure 139 includes a pair of straps 140 that extend from the body portion on opposite sides thereof and are configured to be received by the ears of the patient. Although only one of the straps is fully illustrated, the other strap may have the same configuration. As shown, strap 140 is connected at one end from side surface 131 of tubing holder portion 123, extends around the patient's ear, and is attached to side surface 131 at the other end. The length of strap 140 is sized so that body portion 122 is properly positioned between to the patient's nose and mouth, yet is still comfortable to the patient. As such, different sized patient interfaces 120 are envisioned so that a more custom fit may be provided to the patient. In another embodiment, straps 140 may be adjustable in length so that a "one size fits all" patient interface 120 may be provided.

Figure 17:
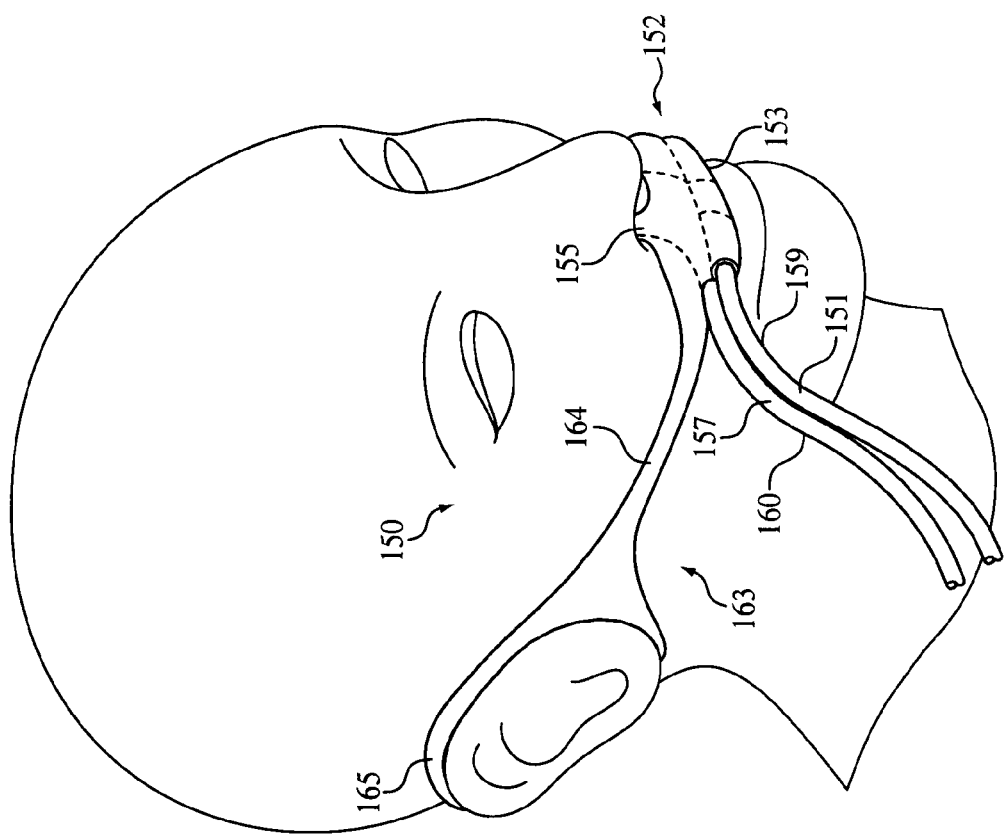
FIG. 17 is a perspective view of another embodiment of a patient interface for gas sampling, supplemental oxygen gas, or combined gas sampling and supplemental gas delivery.

FIG. 17 illustrates yet another embodiment of a patient interface 150 that includes a body portion 152 configured to communicate with at least one fluid path, such as fluid path 151, as shown. Patient interface 150 may be an oral and nasal gas sampling and/or gas delivery cannula or appliance. Body portion 152 includes a section 153 that is inflatable by a fluid so as to provide a pillow-like structure, which may increase patient comfort when the patient interface is mounted to the patient. Two nostril interfaces 154, 155 extend from the body portion 152 and are constructed and arranged to communicate at least one nostril of the patient with fluid path 151.

Inflatable section 153 of body portion 152 may be configured to be in communication with fluid path 151 such that the inflatable section is inflatable with fluid from the fluid path. In an exemplary embodiment, the fluid in fluid path 151 is oxygen. By supplying the fluid to inflatable section 153 with a sufficient back pressure to keep the inflatable section inflated, a "pillow" that is able to substantially conform to the patient's facial anatomy is created.

Inflatable section 153 may be manufactured from an elastomeric material, such as polyurethane, which allows the inflatable section to be flexible, so that it is relatively easy to inflate and conform to the patient's face, while also providing a substantially soft feel to the patient. In an embodiment, the entire body portion 152 is manufactured from the elastomeric material. It is also contemplated that in another embodiment, inflatable section 153 may be not be configured to be in communication with fluid path 151 but instead is constructed and arranged to be inflated manually with a pump or syringe and then sealed, either prior to or after patent interface 150 is mounted to the patient.

Figure 18:
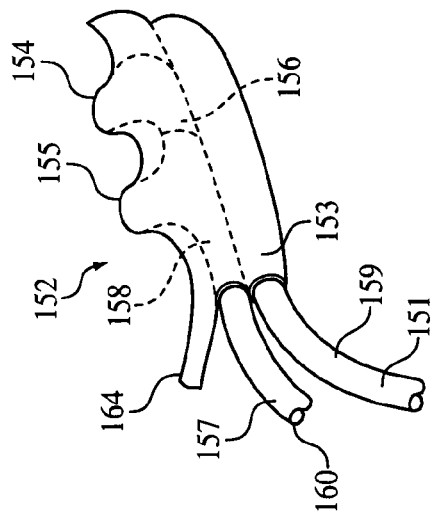
FIG. 18 is a more detailed view of the interface of FIG. 17.

As shown in FIG. 17 and in greater detail in FIG. 18, in an embodiment, one of nostril interfaces 154 is in fluid communication with the fluid path 151 via a conduit 156 within body portion 152, and other nostril interface 155 is in fluid communication with a second fluid path 157 with another conduit 158. Fluid paths 151 and 157 may be provided by suitable tubing 159 and 160, respectively, that are configured to be connected to body portion 152 by methods previously discussed. In the embodiment illustrated in FIGS. 17 and 18, the patient interface is arranged to provide oxygen to one of the patient's nostrils and to sample the fluid being exhaled by the patient from the other nostril.

Figure 19:
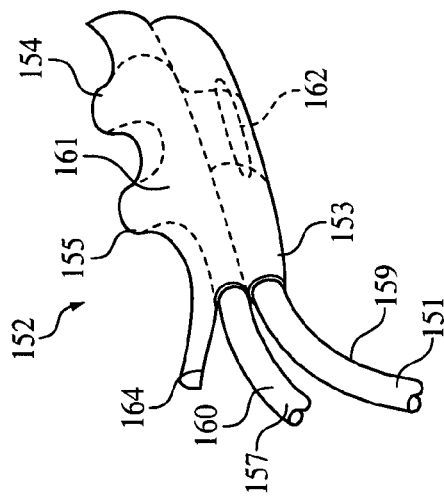
FIG. 19 is a detailed view of another embodiment of the interface of FIG. 17.

As shown in FIG. 19, in one exemplary embodiment, both nostril interfaces 154 and 155 are configured to communicate with fluid path 157 via a conduit 161. In this embodiment, the received fluid path 151 may also be communicated to each of the nostril interfaces 154, 155 via another conduit (not shown) located next to but separate from the conduit 161. In addition, an orifice 162 may be provided in or communicated to inflatable section 153 so that fluid path 151 communicates with the patient's mouth. It should be appreciated that different configurations are possible by providing suitable conduits within the body portion that communicate with fluid paths 141, 157 and nostril interfaces 154, 155. Also, tubing 160 defining fluid path 157 may be contained within inflatable section 153 or may be connected to the inflatable section. The illustrated embodiments are not intended to be limiting in any way.

As shown in FIG. 17, patient interface 150 also includes a mounting structure 163 that includes a pair of straps 164 that are configured to extend from body portion 152 on opposite sides thereof to the ears of the patient to hold the body portion in a fixed position relative to the nostrils of the patient. Although only one strap 164 is fully illustrated, the other strap may have the same configuration. As shown, each strap 164 includes a ring 165 at one end that is configured to surround the ear around a circumference thereof. The straps are preferably made from an elastic material, such as rubber, so that they may be stretched away from body portion 152 and mounted to the patient's ears with sufficient tension so as to hold the body portion in a fixed position relative to the nose of the patient. Straps 164 should be sized such that sufficient tension, but not too much tension, is provided, as too much tension may affect the sustainable pressure in inflatable section 153.

Figure 20:
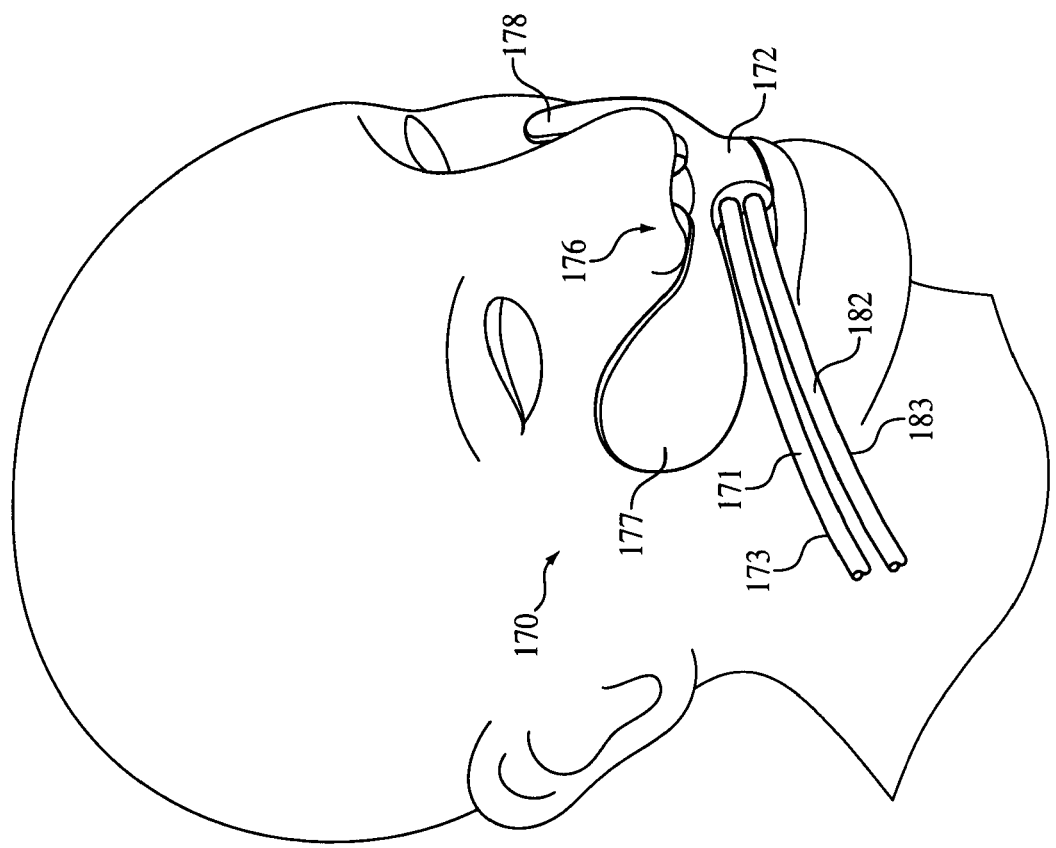
FIG. 20 is a perspective view of another embodiment of a patient interface for gas sampling, supplemental gas delivery, or combined gas sampling and supplemental gas delivery.

FIG. 20 illustrates an embodiment of a patient interface 170 that can be used an oral and nasal gas sampling and/or gas delivery cannula or appliance. Patient interface 170 includes a body portion 172 configured to communicate with a fluid path 171. Fluid path 171 may be defined by tubing 173, as shown in FIG. 20. The fluid path may be configured to receive a fluid being exhaled by the patient through the nasal cavity and/or the oral cavity, or fluid path 171 may be configured to supply a fluid containing oxygen to be inhaled by the patient through the nasal cavity and/or oral cavity.

Figure 21:
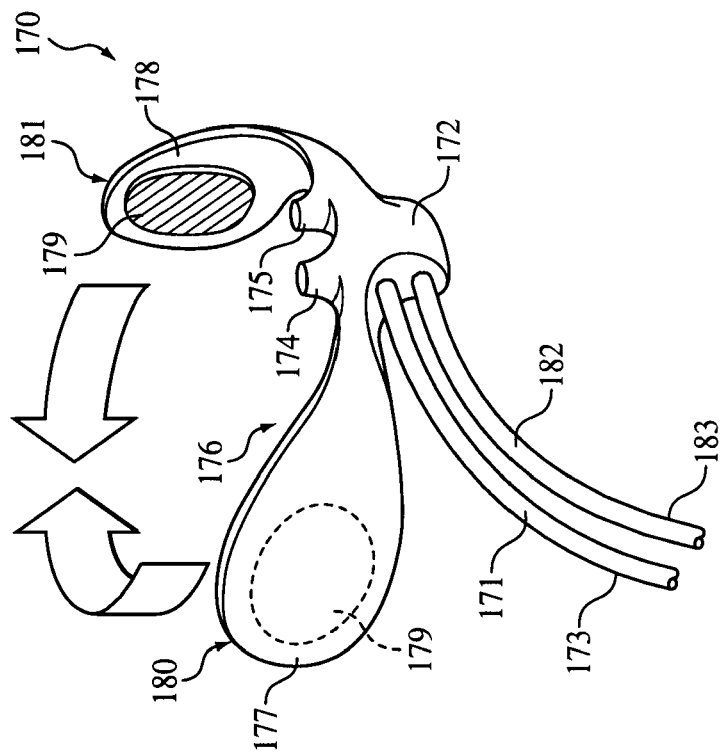
FIG. 21 is a more detailed view of the interface of FIG. 20.

Patient interface 170 also includes two nostril interfaces 174, 175 that extend from body portion 172, as shown in greater detail in FIG. 21. Each nostril interface 174, 175 is configured to be received by a patient's nostril, and either one or both are in communication with fluid path 171. As discussed above, body portion 172 may include internal conduits or passageways that communicate nostril interfaces 174, 175 with fluid path 171. In addition, tubing 173 may be connected to body portion 172 by using similar method and structures discussed above.

Patient interface 170 also includes an attachment portion 176 that includes two extensions 177, 178 that extend from opposite sides of the body portion 172. Extensions 177, 178 may each include of a wing-like malleable structure that is conformable to the patient's face. The extensions, at least in part, provide stability to the patient interface 170, when the interface is mounted to the patient. An adhesive 179 is provided on distal ends 180, 181 of extensions 177, 178. Adhesive 179 is configured to removably attach attachment portion 176, via extensions 177, 178, to the patient's face so as to hold body portion 172 in a fixed position relative to the nose of the patient, so that nostril interfaces 174, 175 are held in a fixed position. Adhesive 179 should be a material that is strong enough to temporarily bond attachment portion 176 to the patient's face, yet be easily removed.

Body portion 172 may also be configured to receive a second fluid path 182, defined by tubing 183. If fluid path 171 is configured to receive the fluid being exhaled by the patient, second fluid path 182 may be configured to supply a fluid containing oxygen to the patient for inhalation.

In the illustrated embodiment, both fluid paths 171, 182 may be received by body portion 172 on a same side of the body portion. In another embodiment, fluid paths 171, 182 may be received on opposite sides of body portion 171 such that tubing 173, 183 extend from body portion 162 in substantially opposite directions. It is also contemplated that an oral sampler may be added to the embodiments shown in FIGS. 20 and 21. The oral sampler may be a separate adjustable structure that is secured to body portion 172, or the body portion may be formed so as to allow the collection of gases being expired from the mouth. The illustrated embodiment is not intended to be limiting in any way.

Figure 22:
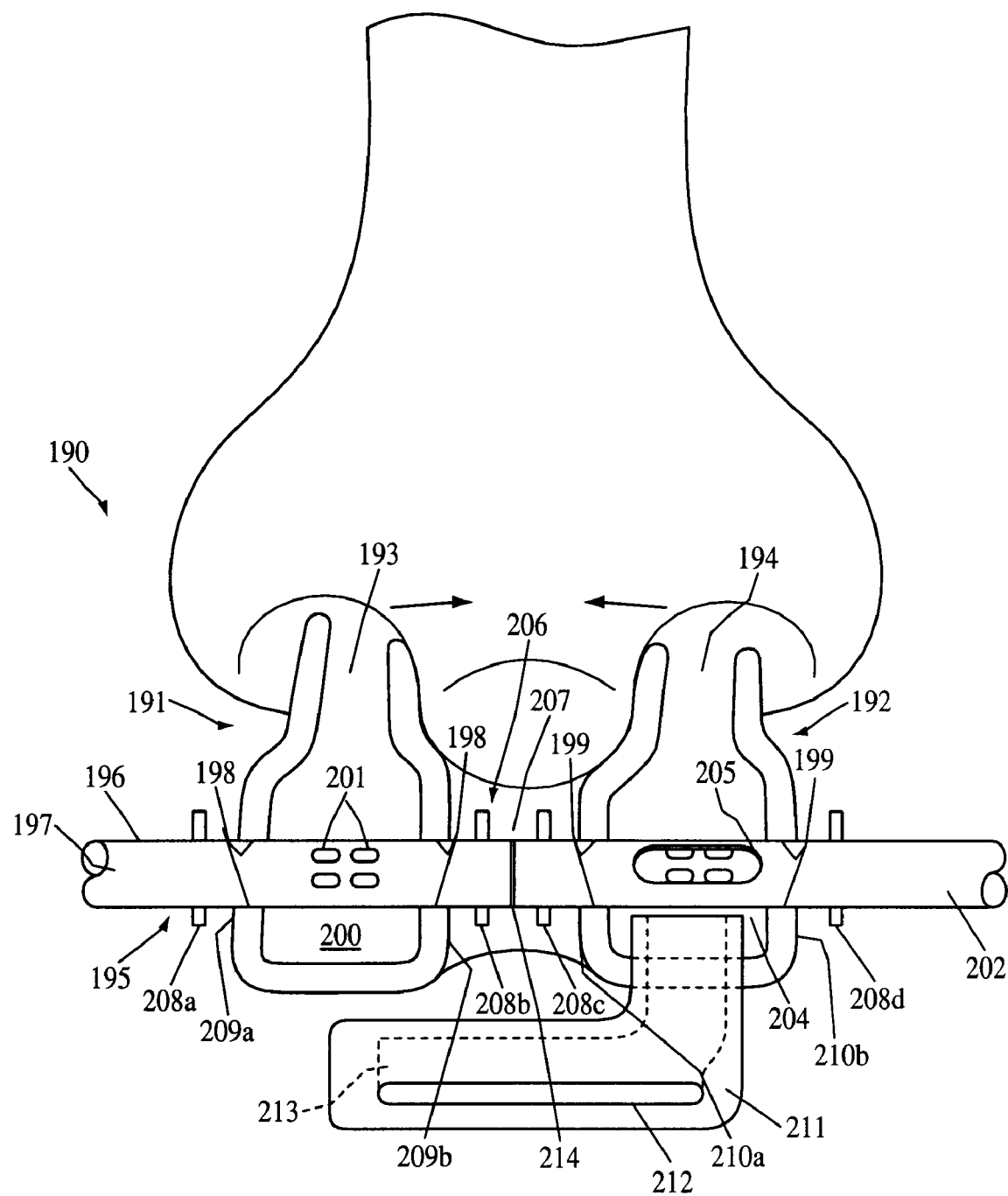
FIG. 22 is a cross-sectional view of another embodiment of a patient interface for carbon dioxide sampling, supplemental oxygen delivery, or combined carbon dioxide sampling and supplemental oxygen delivery.

FIG. 22 illustrates a patient interface 190 that includes a first nostril interface 191 that is configured to be inserted into a first nostril of the patient, and a second nostril interface 192 that is configured to be inserted into a second nostril of the patient. First nostril interface 191 includes a conduit 193 for communicating with the first nostril of the patient. Similarly, second nostril interface 192 includes a conduit 194 for communicating with the second nostril of the patient. As discussed in further detail below, first nostril interface 191 is capable of relative sliding movement with respect to second nostril interface 192 to enable an adjustment of the spacing between the nostril interface 191 and second nostril interface 192.

As illustrated, patient interface 190 includes an interconnecting structure 195. First nostril interface 191 and second nostril interface 192 both frictionally engage interconnecting structure 195 such that sliding frictional movement of the first nostril interface and/or of the second nostril interface along the interconnecting structure enables the adjustment of the spacing between the first and the second nostril interfaces. In an alternative embodiment, one of the nostril interfaces, such as first nostril interface 191, may be joined with interconnecting structure 195 by suitable methods, such as bonding, so that the first nostril interface does not slide relative to interconnecting structure 195 and only the second nostril interface is capable of sliding adjustment.

As shown in the embodiment of FIG. 22, interconnecting structure 195 takes the form of tubing 196 that communicates a fluid path 197 to the first nostril interface 191 via conduit 193. First nostril interface 191 includes engagement surfaces 198 that are configured to slidably sealingly engage tubing 196 such that a lower enlarged cavity 200 defining a space within the first nostril interface is sealed from the surrounding environment. This sealing engagement substantially prevents the fluid being communicated between fluid path 197 and first nostril interface 191 from leaking between the first nostril interface at the points of contact with tubing 196 forming the interconnecting structure 195. Tubing 196 includes at least one orifice 201 at a portion of the tubing that is inside cavity 200, so that the fluid may be communicated between fluid path 197 and first nostril interface 191. Cavity 200 may be part of conduit 193 or may communicate with conduit 193. Orifice 201 may be a single larger orifice or may include a plurality of smaller orifices, as shown in FIG. 22.

Tubing 196 may also be configured to communicate a second fluid path 202 to second nostril interface 192. Specifically, second nostril interface 192 may be configured to slidingly, frictionally engage tubing 196 such that the tubing communicates second path 202 to second nostril interface 192 via conduit 194. The second nostril interface includes engagement surfaces 199 that are configured to sealingly engage tubing 196 such that an enlarged cavity 204 defining a lower space within second nostril interface 192 may be sealed from the surrounding environment. This prevents the fluid being communicated between second fluid path 202 and second nostril interface 192 from leaking between the second nostril interface at the points of contact with tubing 196 forming interconnecting structure 195. Tubing 196 includes an orifice 205 at a portion of the tubing that is inside cavity 204, so that the fluid may be communicated between second fluid path 202 and second nostril interface 192. Cavity 204 may be part of the conduit 194 or may communicate with the conduit 194. The orifice 205 may be a single larger orifice, as shown in FIG. 22, or may include a plurality of orifices.

Patient interface 190 may also include a movement limiting structure 206 that limits movement between first nostril interface 191 and tubing 196, so that the position of orifice 201 is retained within cavity 200. The movement limiting structure 206 may also be configured to limit movement between second nostril interface 192 and tubing 196, so that the position of orifice 205 is retained within cavity 204. In one embodiment, movement limiting structure 206 may include a web of material 207 that interconnects first nostril interface 191 with second nostril interface 192. Web of material 207 may be a cloth or may be a flexible plastic, for example.

In another embodiment, movement limiting structure 206 includes a stop structure that is formed on tubing 196. The stop structure may include portions 208a and 208b that are configured to abut against outside surfaces 209a and 209b of first nostril interface 191 such that portions 280a and 208b may not pass into cavity 200. Similarly, the stop structure may also include portions 208c and 208d that are configured to abut against outer surfaces 210a and 210b of second nostril interface 192 such that portions 208c and 208d may not pass into cavity 204.

As shown in FIG. 22, patient interface 190 may also include an oral sampler 211 that may be received by one of nostril interfaces 191, 192. Oral sampler 211 has an orifice 212 located proximate to the patient's mouth when patient interface 190 is mounted to the patient. Oral sampler 211 includes a conduit 213 for communicating a fluid between the patient's mouth and the second fluid path 202. In the illustrated embodiment, oral sampler 211 is received by second nostril interface 192 in a frictional engagement. It is also contemplated that oral sampler 211 may be permanently connected to nostril interface 192 with a suitable adhesive or plastic weld.

In another embodiment, interconnecting structure 195 may be a structure other than the tubing. For example, the interconnecting structure may comprise a direct link between nostril interfaces 191, 192. More specifically, nostril interface 191 may have a projection received in a tightly toleranced receptacle formed on the outer surface of nostril interface 192, to permit a sliding friction fit therebetween. In this arrangement of a connecting structure, nostril interfaces 191, 192 may be directly welded or otherwise bonded to respective tubing ends of the associated fluid paths, so that no movement of nostril interfaces 191, 192 occurs with respect to the associated tubing in fluid communication therewith.

The illustrated embodiment is not intended to be limiting in any way. In an embodiment, nostril interface 191, 192 and web of material 207 may be assembled first, and oral sampler 211 may be added at the end of the manufacturing process, or may not be added at all. Instead, a sealing structure (not shown) may be used to seal nostril interface 192 if the patient interface is not intended to be used for oral sampling or delivery. Because oral sampler 211 can be added at the end of manufacture, the oral sampler can be selected from a plurality of prefabricated sampler sizes and shapes, based on the size of the patient and spacing between the nose and mouth, as well as the shape of the mouth and expiratory flow pattern (e.g. pulsed breathing versus normal breathing).

For embodiments in which patient interface 190 is to be used as a sampling and delivery cannula, two fluid paths 197, 202 may be separated with a separator 214 within the tubing 196. For embodiments in which patient interface 190 is to be used as a sampling-only cannula, fluid paths 197, 202 may be communicated within tubing 196, or alternatively, the tubing may form a single fluid path that receives expired fluid from both nostril interfaces 191, 192.

To mount patient interface 190 to the patient, tubing 196 may be configured to extend from first nostril interface 191 and second nostril interface 192 and at least partially around each of the patient's ears in a similar manner that is illustrated in the embodiment shown in FIG. 1, for example. Of course, any suitable structure may be used to mount patient interface 190, or any of the patient interfaces disclosed herein, to the patient.

Figure 23:
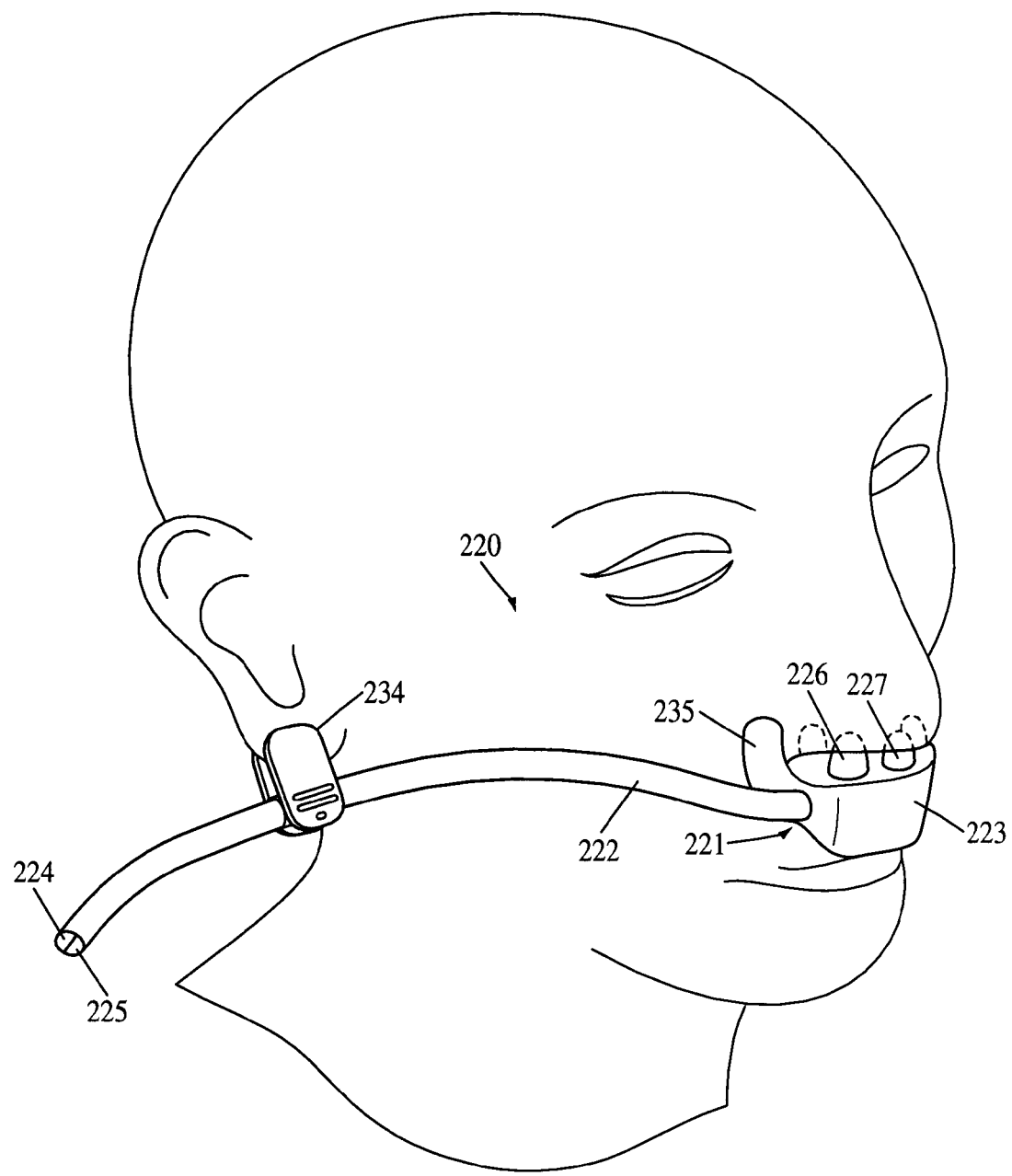
FIG. 23 is a perspective view of another embodiment of a patient interface for gas sampling, supplemental gas delivery, or combined gas sampling and supplemental gas delivery.

FIG. 23 illustrates an embodiment of a patient interface 220 that includes an integrally formed structure 221. Integrally formed structure 221 includes a tubing portion 222 and an appliance portion 223. Integrally formed (e.g. extruded) plastic tubing portion 222 defines a first fluid path 224, and a second fluid path 225. The appliance portion 223 includes a first nostril interface 226, which communicates with first fluid path 224, and a second nostril interface 227, which communicates with second fluid path 225.

Figure 24:
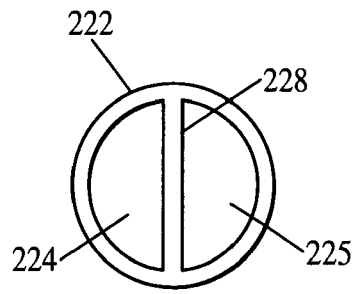
FIG. 24 is a cross-sectional view of a tubing portion of the interface of FIG. 23.

As shown in FIG. 24, tubing portion 222 includes a separator 228 (e.g. wall) for separating first fluid path 224 from second fluid path 225. This allows tubing portion 222 to be configured to receive a fluid being exhaled from the patient as well as supply a fluid, such as oxygen, to be inhaled by the patient. Fluid paths 224, 225 may be of an equal cross-section, or one of the cross-sectional areas may be larger than the other. For example, in an embodiment, the cross-sectional area of fluid path 225 that supplies oxygen to the patient is larger than the cross-sectional area of fluid path 224 that receives fluid from the patient to minimize the pressure drop of tubing portion 222. The illustrated embodiment is not intended to be limiting in any way.

Figure 25:
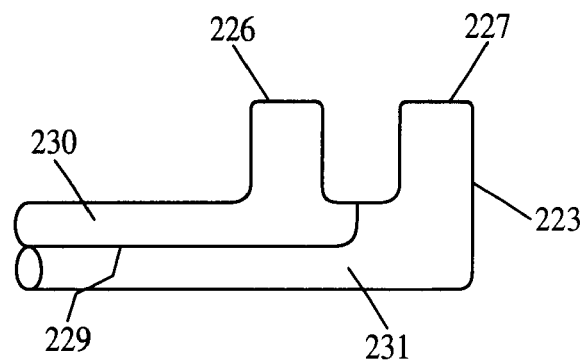
FIG. 25 is a schematic cross-sectional view of an appliance portion of the interface of FIG. 23.

As shown in FIG. 25, appliance portion 223 also includes a separator 229 that defines a first conduit 230 that extends between first nostril interface 226 and first fluid path 224 and a second conduit 231 that extends between second nostril interface 227 and second fluid path 225. As such, separator 229 separates fluid communication between first nostril interface 226 and second nostril interface 227.

Tubing portion 222 and appliance portion 223 are connected, for example, in an ultrasonic welding or heat fusion process, such that separator 228 in the tubing portion and separator 229 in the appliance portion are connected, thereby separating fluid communication between first fluid path 224 and second fluid path 225 throughout integrally formed structure 221. First fluid path 224 may communicate fluid from the nasal cavity of the patient that is exhaled through one of the patient's nostrils, and second fluid path 225 may communicate another fluid, such as oxygen, to the nasal cavity of the patient through the other nostril. Appliance portion 223 may also include an oral sampler. The illustrated embodiment is not intended to be limiting in any way.

Figure 26:
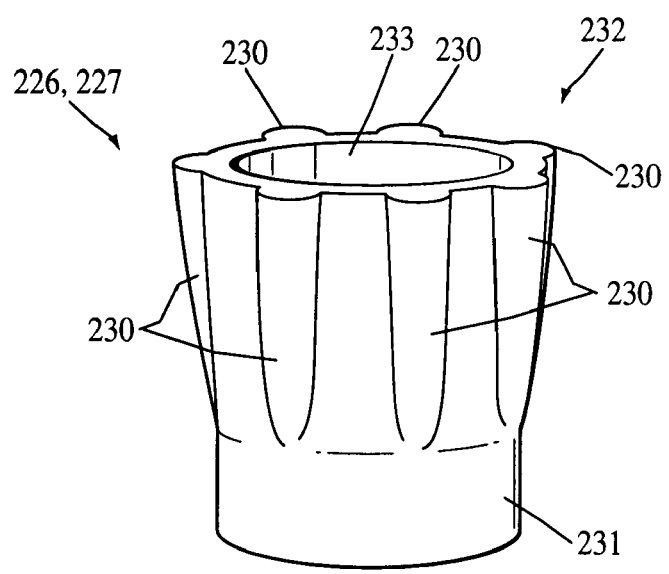
FIG. 26 is a more detailed view of a distal end of a nostril interface of the patient interface of FIG. 23.

As shown in FIG. 26, each of nostril interfaces 226, 227 may include a plurality of ribs 230 that extend from an outer surface 231 of the nostril interface 226, 227 at a distal end 232 thereof. Ribs 230 are configured to position each nostril interface 226, 227 so that an orifice 233 at distal end 232 of each nostril interface 226, 227 may be located away from the inside surface of the respective nostril. In addition, ribs 230 may help reduce the intake of liquids and solids from the nasal cavity. This may allow for a less obstructed flow of fluid being supplied to or received from the nasal cavity. This ribbed structure may be used with any nasal cannula disclosed herein.

To assist with holding tubing portion 221 in place relative to the patient, patient interface 220 may also include a spring clip 234 that is configured to removably attach tubing portion 221 to the patient's ear or an article of clothing. In one embodiment, the spring clip may be of a clothespin type construction, with an aperture therethrough adjacent the pivot axis, which aperture is dimensioned to slidably, frictionally receive the tubing portion 221 therethrough.

As shown in FIG. 23, appliance portion 222 may also have a securement portion 235 that is disposed proximate to one of nostril interfaces 226 and is constructed and arranged to engage an exterior surface of the patient's nose such that the securement portion and the nostril interface are cooperable, such that the resiliency of the plastic material thereof enable clamping of an alar sidewall portion of the patient's nose therebetween. In an embodiment, a second securement portion may be disposed proximate to other nostril interface 227 and may be configured to engage an exterior surface of the patient's nose such that the second securement portion and the nostril interface are cooperable to clamp the other alar sidewall portion of the patient's nose. The illustrated embodiment is not intended to be limiting in any way.

Figure 27:
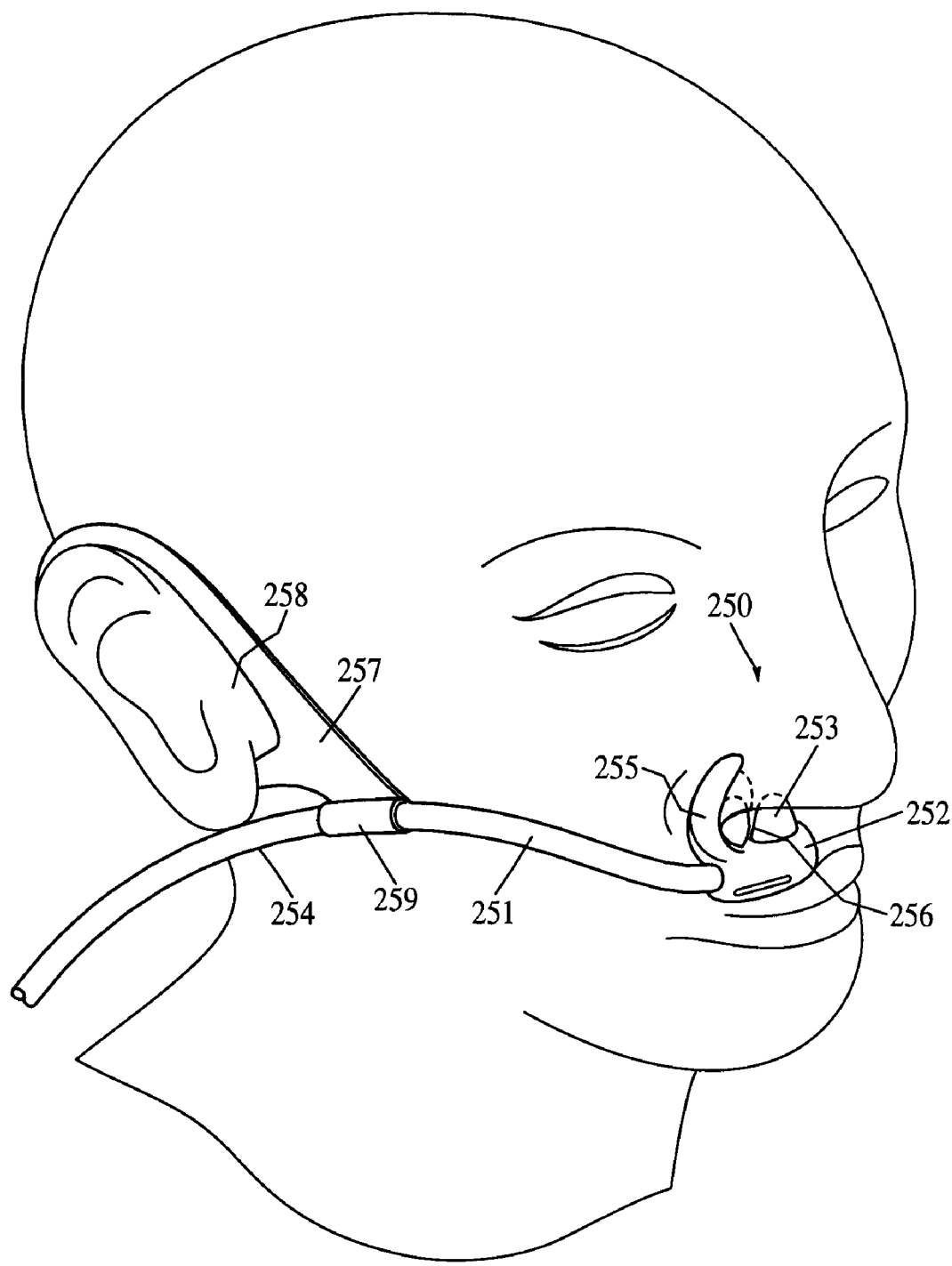
FIG. 27 is a perspective view of another embodiment of a patient interface for gas sampling, supplemental gas delivery, or combined gas sampling and supplemental gas delivery from or to a single nostril.

FIG. 27 illustrates another embodiment of a patient interface 250 of the present invention configured to be a gas sampling and/or gas delivery cannula that samples and/or delivers fluid from/to a single nostril. It is contemplated that patient interface 250 may be particularly advantageous if a naso-gastric feeding tube is in use, thereby effectively making one nostril unavailable for sampling or oxygen delivery.

As illustrated, patient interface 250 includes a body portion 252 that is configured to communicate with a fluid path 251. A single nostril interface 253 extends from body portion 252 and is configured to be received by the patient's nostril, and to provide fluid communication between the nasal cavity via the nostril and fluid path 251.

In the illustrated embodiment, fluid path 251 is defined by tubing 254. In one embodiment, tubing 254 is configured to carry fluid exhaled by the patient through the nasal cavity via one nostril to a receiver, such as a gas analyzer, for determining the concentration of carbon dioxide in the fluid over time. In another embodiment, tubing 254 is configured to supply a fluid containing oxygen, to the nasal cavity as the patient inhales though the nostril.

It is also contemplated that tubing 254 may be configured to also define a second fluid path, either in the manner discussed above and illustrated in FIG. 24, or in the manner illustrated in FIG. 30, or in the manner illustrated in FIG. 55, which is discussed in greater detail later. Similarly, in an embodiment, body portion 252 and nostril interface 253 may include separators that separate the fluids communicated between the nostril and the first and second fluid paths. An example of a single nostril interface that communicates two fluids in separate paths is discussed in further detail below and illustrated in FIG. 31.

Interface 250 also includes a securement portion 255 that is disposed proximate to nostril interface 253 and is constructed and arranged to engage an exterior surface of the patient's nose such that the securement portion and the nostril interface are cooperable to securely engage or lightly clamp an alar sidewall portion of the patient's nose therebetween. The resiliency of the material forming securement portion 255 and/or of nostril interface 253 create an inwardly directed spring force once these portions are separated to receive the alar sidewall therebetween so as to engage or lightly clamp the alar sidewall portion of the patient's nose between the nostril interface and the securement portion.

As illustrated in FIG. 27, patient interface 250 also may optionally include a second securement portion 256 that is disposed more proximate to nostril interface 253 than first securement portion 255. Second securement portion 256 may be constructed and arranged to cooperate with first securement portion 255 so as to clamp a portion of the patient's nose therebetween. Such an arrangement would not interfere with nostril interface 253, and would not require the nostril interface to participate in the clamping function.

As shown in FIG. 27, the patient interface 250 may include a head gear that includes a strap 257 that is configured to be received by an ear of the patient and is also connected to the tubing 254 so as to support tubing 254. As illustrated, strap 257 includes an opening 258 for receiving the ear, and a holder 259 that is configured to engage a portion of the tubing 254 and allow the tubing 254 to pass therethrough without creating a kink in the tubing. It is also contemplated that in some embodiments, rather than having the strap 257, patient interface 250 may include a clip, like clip 234 illustrated in FIG. 23 that is configured to be clamped to the ear of the patient so that the ear may support tubing 254 more directly. The illustrated embodiment is not intended to be limiting in any way.

Figure 28:
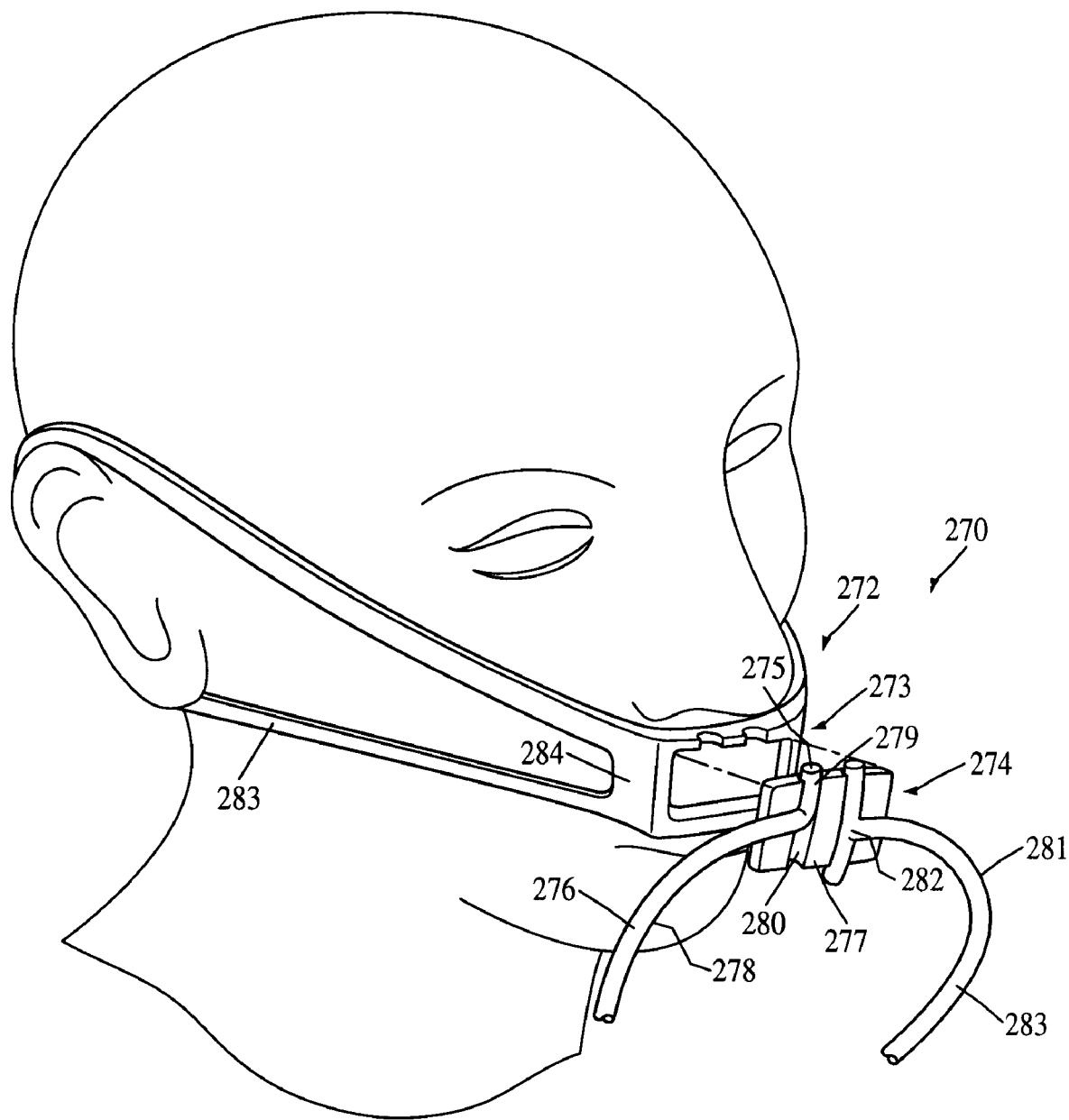
FIG. 28 is a perspective view of another embodiment of a patient interface for gas sampling, supplemental gas delivery, or combined gas sampling and supplemental gas delivery.

FIG. 28 illustrates a patient interface 270 according to a still further embodiment of the invention. Patient interface 270 includes a head mount 272 that is configured to be secured on the head of a patient. Head mount 272 includes a docking portion 273 that is constructed and arranged to be disposed proximate to the nose of the patient, and an appliance 274 that is configured to be removably attached to the docking portion. Appliance 274 includes at least one nostril interface, such as nostril interface 275, for communicating a fluid path 276 with the nostril of the patient.

Appliance 274 also includes a body portion 277 and tubing 278 that is secured to the body portion. In one embodiment, a distal end 279 of the tubing defines nostril interface 275. Tubing 278 also defines fluid path 276. Body portion 277 includes a network of grooves 280 that is configured to receive tubing 278 and secure the tubing to the body portion. Grooves 280 may be constructed and arranged like grooves 121a, 121b described above and illustrated in FIGS. 15 and 16, the discussion of which is hereby incorporated by reference.

As illustrated in FIG. 28, a second tubing 281 having a T-shaped junction 282 and defining a second fluid path 283 may alternatively, or additionally, be provided and secured to body portion 277 in a similar manner that is discussed above in regard to the tubing 125 shown in FIGS. 15 and 16.

Head mount 272 includes a pair of straps 283 that extend from the docking portion 273 on opposite sides thereof and are configured to be received by the ears of the patient. Although only one of the straps is fully illustrated, the other strap may have the same configuration. As shown, strap 283 is connected at one end from a side surface 284 of docking portion 273, extends around the patient's ear, and is attached to side surface 284 at the other end. The length of strap 283 is sized so that docking portion 273 is properly positioned between to the patient's nose and mouth, yet is still comfortable to the patient, so that when the appliance is attached to docking portion 273, the nostril interface is properly located relative to the nostril of the patient so as to communicate the fluid paths 276, 283 to the nostrils of the patient. Of course, the present invention contemplates that an adjustment mechanism can be provided to change the length of strap 283.

A plurality of head mounts having different lengths of straps, but also having docking portions of the same size, may be provided so that head mounts of different sizes may be used with the same appliance. This may allow the clinician to select a head mount of an appropriate size for the patient, and attach the appliance to the docking portion of that particular head mount. After the appliance has been used, the appliance may be removed from the docking portion and discarded, and the head mount may be cleaned and/or sterilized and reused on another patient, if desired, or the head mount may also be discarded or recycled.

Figure 29:
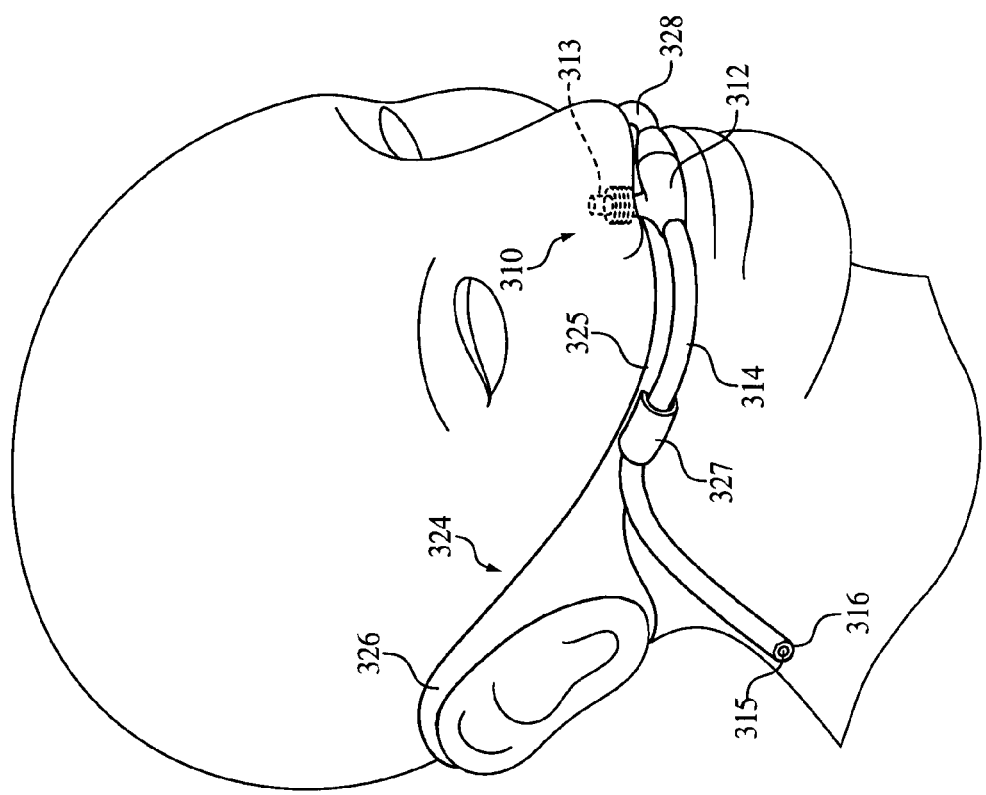
FIG. 29 is a perspective view of another embodiment of a patient interface for gas sampling, supplemental gas delivery, or combined gas sampling and supplemental gas delivery from or to a single nostril.

FIG. 29 illustrates a patient interface 310 according to an embodiment of the invention suitable for use as a gas sampling and delivery cannula. Patient interface 310 includes a body portion 312 and a nostril interface 313 that extends from the body portion. Nostril interface 313 is configured to be received by a nostril of the patient's nose. Patient interface 310 also includes tubing 314 that is connected to body portion 313. Tubing 314 defines a first fluid path 315 and a second fluid path 316.

Figure 30:
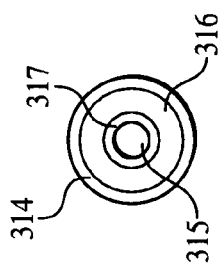
FIG. 30 is a cross-sectional view of a tubing portion of the interface of FIG. 29.

As shown in FIG. 30, in an exemplary embodiment, tubing 314 includes a separator 317 that separates first fluid path 315 from second fluid path 316 such that the second fluid path substantially surrounds or completely surrounds the first fluid path. Alternatively, two separate tubes may be connected to opposite sides of body portion 312, one tube for delivering oxygen, the other drawing samples of expired gas.

Figure 31:
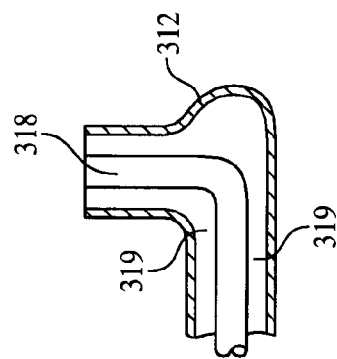
FIG. 31 is a schematic cross-sectional view of an appliance portion of the interface of FIG. 29.

As shown in the embodiment of FIG. 31, body portion 312 has a first passage 318 therein that is configured to communicate with first fluid path 315 configured to withdraw a fluid from the nasal cavity of the patient. Body portion 312 also has a second passage 319 configured to communicate with second fluid path 316 to supply a fluid, such as oxygen, to the patient so that the patient may inhale the second fluid.

Figure 32:
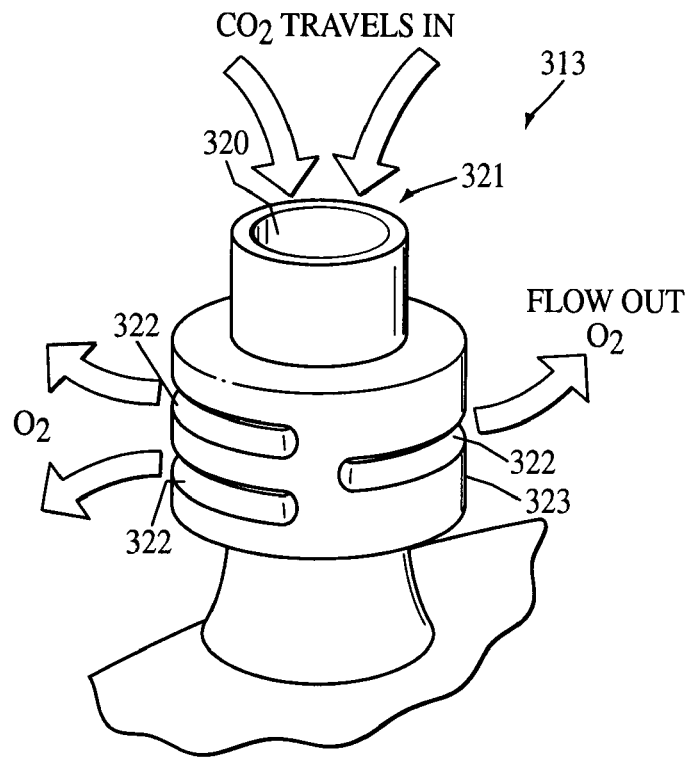
FIG. 32 is a more detailed view of a nostril interface of the patient interface of FIG. 29.

A shown in greater detail in FIG. 32, nostril interface 313 has a first orifice 320 at a distal end 321 thereof that is configured to communicate with first passage 318 of the portion 312 and is also configured to receive the fluid from the patient. Nostril interface 313 also includes a second orifice 322 at an outside circumferential surface 323 thereof that is configured to communicate with the second passage 319 of body portion 312 and is also configured to output fluid (oxygen) to the patient. In the illustrated embodiment, second orifice 322 includes a plurality of orifices that may allow for an improved distribution of the fluid being supplied to the patient. The size, shape, and number of orifices 322 can be varied.

As illustrated in FIG. 29, patient interface 310 may also include a head mount 324 that is configured to support tubing 314. Head mount 324 may include a strap 325 that is connected to body portion 312 and extends from the body portion to the patient's ear. Although only one strap is illustrated, head mount 324 may include a second strap that is essentially the same as strap 325. As such, only strap 325 will be discussed herein.

Strap 325 includes a ring portion 326 on one end thereof that is configured to circumferentially surround the patient's ear, as shown in FIG. 29. Strap 325 also includes a holder portion 327 between the ring portion 326 and the body portion 312. Holder portion 327 is configured to hold a portion of tubing 314 in a manner that does not create a kink in the tubing and also allow the tubing to extend therethrough. The head mount is configured to hold body portion 312 in a fixed position between the patient's nose and mouth. The other strap (not illustrated) may be configured to be connected to body portion 312 at one end and may also have a ring portion at the other end to circumferentially surround the patient's other ear.

In addition, as shown in FIG. 29, other tubing 328 may be connected to body portion 312 to function as a further support for the body portion so that the body portion 312 and nostril interface 313 stay in a fixed position. In such an embodiment, the other strap may also support tubing 328 with a holder portion in a similar manner as holder portion 327 that is illustrated.

It is also contemplated that body portion 312 may be configured so that only one of fluid paths 315 is defined by tubing 314 and second fluid path 316 is defined by tubing 328. Body portion 312 may include internal conduits or passageways that communicate the fluid being received from the patient from first orifice 320 in nostril interface 313 to first fluid path 315, and also communicate the fluid being supplied to the patient from second fluid path 316 to second orifice 322. The illustrated embodiment is not intended to be limiting in any way.

It is also contemplated that in some embodiments, rather than the having straps, head mount 324 may include a clip that is configured to be attached to the patient's ear in a manner that supports tubing 314, like clip 234 illustrated in FIGS. 23 and described above. The term "head mount" is intended to generally define a structure that allows tubing 314 to be supports by the patient's head. The illustrated embodiment is not intended to be limiting in any way.

In yet another embodiment, the nose clamping arrangement illustrated and discussed with respect to the embodiment of FIG. 27 may be employed.

Figure 33:
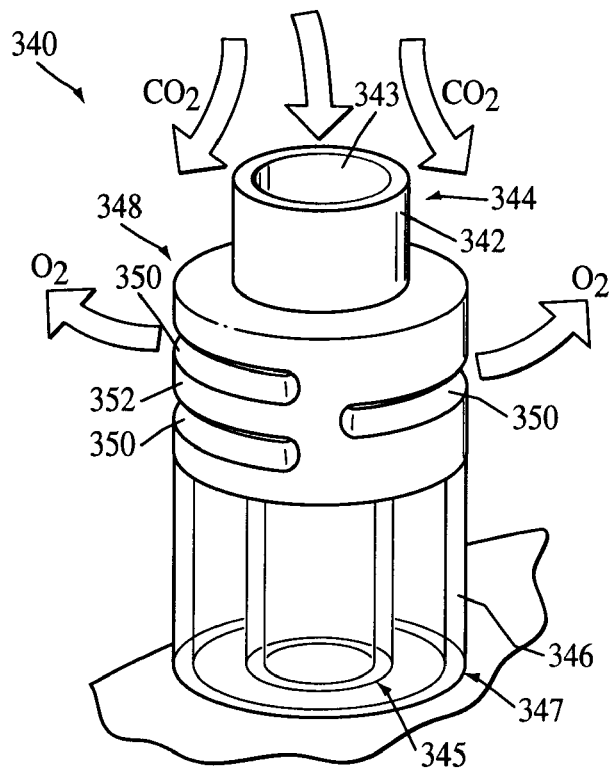
FIG. 33 is a perspective view of an embodiment of a nostril interface for combined gas sampling and supplemental gas delivery.

FIG. 33 illustrates an embodiment of a nostril interface 340 that is a slightly modified version of nostril interface 313 described above and illustrated in FIG. 32. Nostril interface 340 is configured to be inserted into a nostril of the patient and includes an inner conduit 342 that extends through the nostril interface. Inner conduit 342 is configured to receive a fluid that is being exhaled by the patient from the nasal cavity via the nostril. Inner conduit 342 includes an orifice 343 and a distal end 344 thereof. A proximal end 345 of inner conduit 342 is configured to communicate with a fluid path of a patient interface, cannula, or appliance that communicates the fluid with a supplier or receiver as discussed above.

Nostril interface 340 also includes an outer conduit 346 that surrounds at least a portion of inner conduit 342, as shown in FIG. 33. Outer conduit 346 is configured to communicate a second fluid to the nostril of the patient so that the patient may inhale the second fluid. A proximal end 347 of outer conduit 346 is configured to communicate with second fluid path of the patient interface, cannula, or appliance that communicates the second fluid with the supplier or receiver.

One of the traditional problems with oxygen delivery to patients is that the oxygen is often delivered as a dry gas, which has a tendency to dry the nasal passages. As shown in FIG. 33, nostril interface 340 also includes a moisture exchanger 348 that forms outlet port openings or orifices 350 of outer conduit 346 and surrounds inner conduit 342.

Moisture exchanger 348 is configured to receive moisture from the fluid being exhaled by the patient through the nostril (and not entering orifice 343 of the inner conduit) and to supply at least a portion of the moisture contained thereby to the fluid that is being supplied to the patient through orifice 350. As shown in FIG. 33, moisture exchanger 348 is made from a hydrophyllic filter material 352. Such an exchanger may also be a heat-moisture exchanger (HME) that also exchanges heat. As the exhaled air passes over moisture exchanger 348, a portion of the water vapor in the saturated expiratory fluid is absorbed. During the following inspiration, the fluid, such as oxygen, that is delivered to nostril interface 340 passes through moisture exchanger 348 and the water content of the delivered fluid may be increased from "dry." This may be particularly suited for pulsed oxygen delivery systems. Other arrangements of the moisture exchanger may be used with the nostril interface. The illustrated embodiment is not intended to be limiting in any way.

Figure 34:
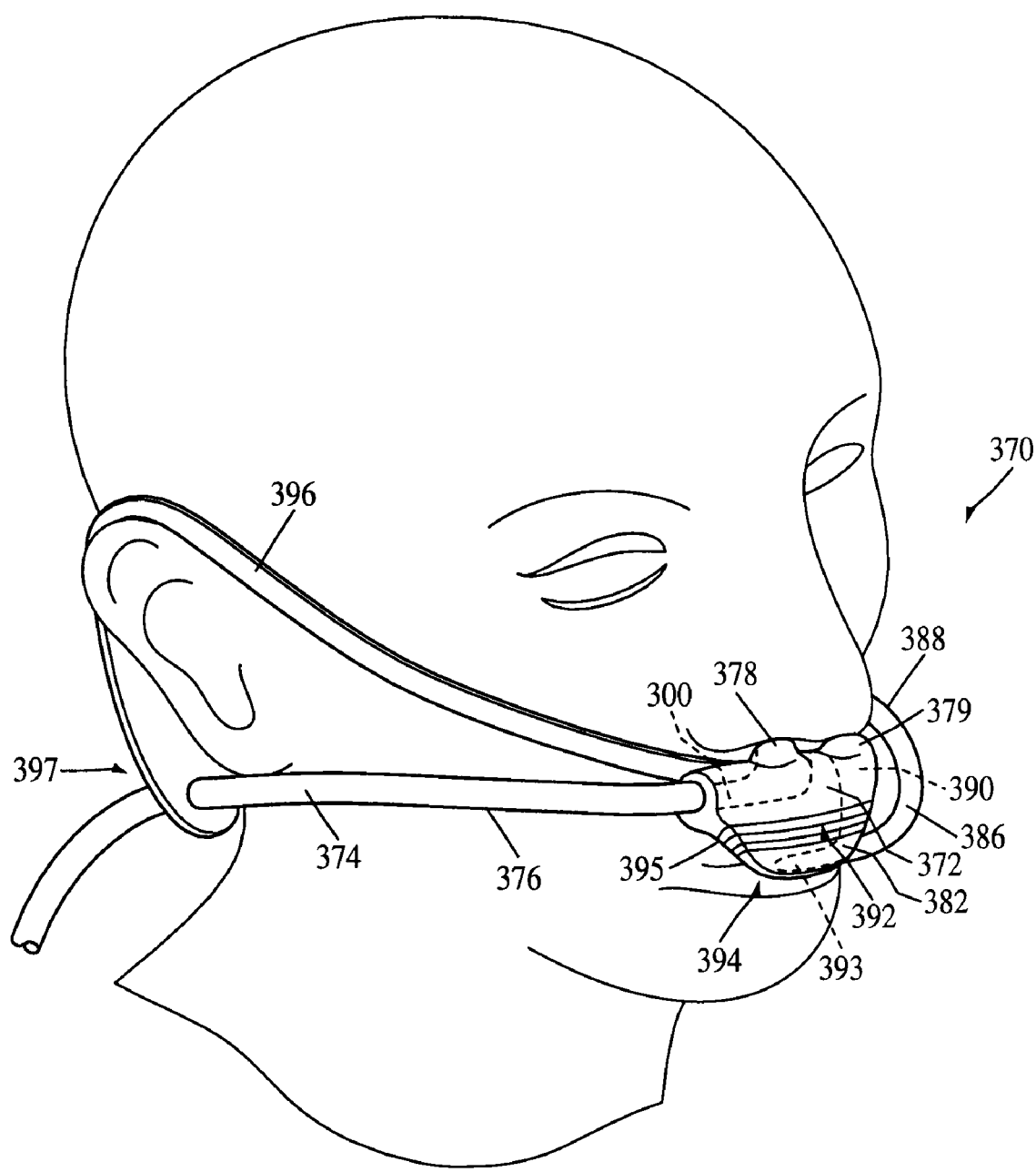
FIG. 34 is a perspective view of another embodiment of a patient interface for gas sampling, supplemental gas delivery, or combined gas sampling and supplemental gas delivery.

FIG. 34 illustrates a patient interface 370 according to another embodiment of the invention. Patient interface 370 includes a body portion 372 that is configured to communicate with a fluid path 374. The fluid path 374 may be defined by tubing 376, and may be configured to supply a fluid to the body portion 372. Patient interface 370 also includes a first nostril interface 378 and a second nostril interface 379 that extend from body portion 372. First nostril interface 378 is configured to be received by one nostril of the patient and second nostril interface 379 is configured to be received by the other nostril. Body portion 372 includes at least one internal conduit or passageway that is configured to communicate fluid path 374 to one or both of the nostril interfaces 378, 379 so that a gas may be supplied to or sampled from one or both of nostril interfaces 378, 379, accordingly. In the illustrated embodiment, body portion 372 includes a conduit 380 that is configured to communicate fluid path 374 with first nostril interface 378. The illustrated embodiment is not intended to be limiting in any way.

As shown in FIG. 34, patient interface 370 also includes an oral sampler portion 382 that extends from body portion 372. Oral sampler portion 382 is configured to receive a fluid being exhaled from the patient's mouth, and communicate the fluid to a second fluid path 386. Second fluid path 386 may be defined by tubing 388 that is connected to and extends from the sampler portion 382 to a receiver. As discussed above, the receiver may include a gas analyzer so that the concentration of carbon dioxide in the fluid may be determined over time. Body portion 372 may be configured to communicate one or both of nostril interfaces 378, 379 to second fluid path 386 via internal conduits so that fluid being exhaled by the patient through the nose may also be communicated to the receiver. In the illustrated embodiment, body portion 372 includes a second conduit 390 that communicates second nostril interface 379 to fluid path 386. The illustrated embodiment is not intended to be limiting in any way.

Oral sampler portion 382 may include a malleable structure 392 that allows an orifice 393 at a distal end 394 of oral sampler portion 383 to be adjusted relative to the patient's mouth. The malleable structure 392 may include bellows 395 or an accordion-like structure, as shown, that allows the oral sampler portion 382 to lengthen, shorten, or be repositioned so that orifice 393 may be optimally positioned. In other embodiments, the malleable structure include a malleable wire or wires, as described in embodiments above. The illustrated embodiment is not intended to be limiting in any way.

A pair of straps 396 (only one of which is shown in FIG. 34) may extend from body portion 372 on opposite sides thereof. Each strap 396 may be configured to at least partially surround an ear of the patient to hold the body portion in a fixed position relative to the nostrils of the patient. In the illustrated embodiment, tubing 376 is configured to pass through a distal end 397 of strap 396. The distal end of strap 396 is configured to slide along tubing 376 so as to adjust tension in strap 396 as well as the tubing when patient interface 370 is mounted to the patient. Similarly, tubing 388 that extends from oral sampler portion 382 may be configured to pass through a distal end of the other strap. The distal end of the other strap may also be configured to slide along tubing 388 so as to adjust tension in that strap and tubing 388 when the patient interface is mounted to the patient. Of course, any type of head mount, including the head mounts discussed herein, may be used to support the patient interface. The illustrated embodiment is not intended to be limiting in any way.

In embodiments described above, it should be appreciated that the portions of the tubing proximate to the patient may not only act as part of the patient interface (e.g., where the tubing wraps around the patient's ear), but may also be considered to be part of the appliance. In addition, in some embodiments, the tubing itself acts as the nostril interfaces, such as illustrated in FIGS. 15, 16, and 28, for example.

It is contemplated that any of the embodiments of the patient interfaces described herein may include scented portions, or may provide a scented fluid to the patient to help relieve any anxiety that the patient may be experiencing. Such an addition of a scent via a nasal cannula has been tried, as evidenced by the article: Redd, W. H., Manne, S. L., Peters, B., Jacobsen, P. B., and Schmidt, H., "Fragrance administration to reduce anxiety during MR imaging," 1994 J Magn Reson Imaging 4; 4:623-6, which is incorporated herein by reference in its entirety. Scents may include, but are not limited to vanilla or strawberry.

It is also contemplated that features shown and described herein may be used in combinations not specifically described. As such, none of the illustrated and/or described embodiments are intended to be limiting in any way.

A recent study found that patients having significant obstruction in their nasal passageway could reliably determine which side of the nose is more obstructed. Clarke J D, Hopkins M L, Eccles R., "How good are patients at determining which side of the nose is more obstructed?" Am J Rhinol. 2006 January-February;20(1):20-4, hereby incorporated by reference in its entirety. Accordingly, it may be desirable in some instances to provide a patient interface that permits gas sampling from both nostrils and oxygen delivery preferentially to either the right or left nostril and that also allows for simple and repeated (as needed) adjustment by either the clinician or patient without removal from the face.

Figure 35:
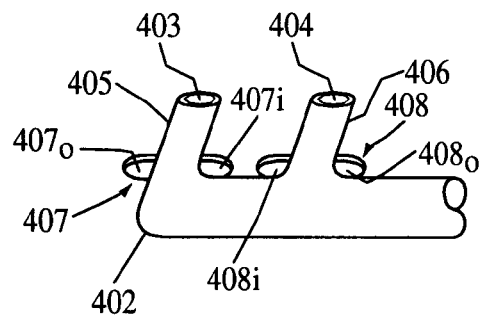
FIG. 35 is a cross-sectional view of an embodiment of nasal interface portion of a patient interface for combined gas sampling and supplemental gas delivery.

FIGS. 35-40 illustrate a patient interface 400 according to embodiments of the present invention. Patient interface 400 includes a nasal interface 402, as shown in FIG. 35, that is configured to be inserted into the nostrils of the patient for receiving a fluid exhaled by the patient from the nasal cavity through the nostrils. Specifically, nasal interface 402 includes a first nostril interface 405 having a first orifice 403 for communicating with the first nostril, and a second nostril interface 406 having a second orifice 404 for communicating with the second nostril. Nostril interfaces 405, 406 that are to be received by the nostrils may be curved so as to substantially conform to the curvature in the nostrils. Each nostril interface 405, 406 includes a sealing portion 407, 408, respectively, that is positioned to remain outside of the nostrils, as will be discussed in further detail below.

Figure 36:
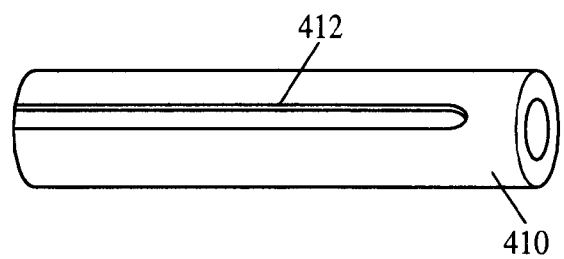
FIG. 36 is a perspective view of an embodiment of a fluid delivery conduit of a patient interface for combined gas sampling and supplemental gas deliver.
Figure 37:
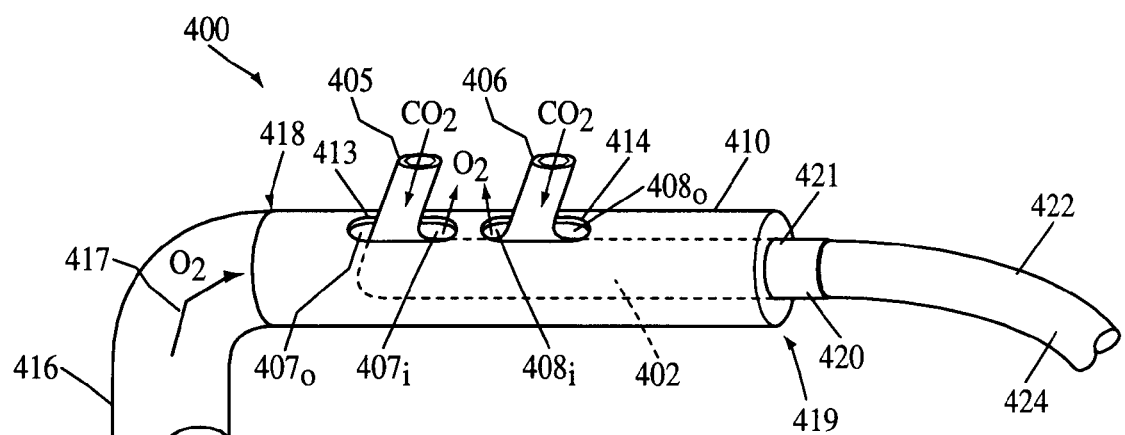
FIG. 37 is a perspective view of a patient interface for combined gas sampling and supplemental gas delivery that includes the nasal interface portion of FIG. 35 and an embodiment of the fluid delivery conduit of FIG. 36 with the fluid delivery conduit in a first position relative to the nasal interface.

Patient interface 400 also includes a fluid delivery conduit 410, as shown in FIG. 36, that is configured to deliver a fluid to at least one of the nostrils of the patient. As discussed in further detail below, fluid delivery conduit 410 is movable relative to nasal interface 402. Fluid delivery conduit 410 includes at least one output orifice 412. In the embodiment illustrated in FIGS. 37, 39, and 40, fluid delivery conduit 410 includes two output orifices 413, 414, each of which substantially surrounds a corresponding nostril interface 405, 406 of nasal interface 402. As shown in FIG. 37, once the nostril interface is inserted into fluid delivery conduit 410, nostril interfaces 405, 406 extend through output orifices 413, 414, and sealing portions 407, 408 remain inside of fluid delivery conduit 410 in a sealing relationship with respect to output orifices 413, 414.

Fluid delivery conduit 410 may be a pillow-like structure that is made of soft, conformable material such as polyurethane so as to function as an inflatable nasal pillow, much like the structure discussed above and illustrated in FIG. 17, when the fluid is communicated to fluid delivery conduit 410 from tubing 416 that defines a fluid path 417.

As shown in FIG. 37, a connecting portion 420 of nasal interface 402 extends through an end 419 of fluid delivery conduit 410 that is opposite end 418 that receives fluid path 417. Connecting portion 420 is configured to connect with a fluid path that communicates the fluid being exhaled by the patient through the nostrils for delivery to a gas analyzer. End 419 may initially be closed off by a flexible membrane 421. Flexible membrane 421 may be punctured by the harder material of connecting portion 420. Subsequently, resilient engagement between flexible membrane 421 and connecting portion 420 provides a sliding sealed engagement to inhibit leakage of oxygen during sliding movement of delivery conduit 410 relative to nasal interface 402. Alternatively, after puncturing, flexible membrane 421 may be bonded to connecting portion 420 such that the flexible member moves (flexes) with nasal interface 402 when the fluid delivery conduit and the nostril interface move relative to each other. Connecting portion 420 is configured to be connected to tubing 422 that defines a fluid path 424 for receiving expired gas.

Figure 38:
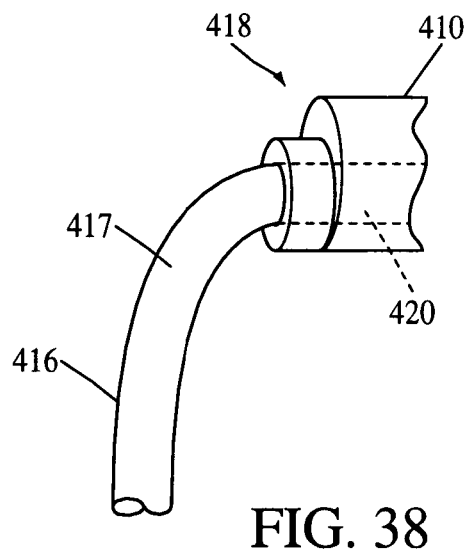
FIG. 38 is a more detailed view of one end of the patient interface of FIG. 37.

In an embodiment, patient interface 400 may be configured to be used solely as a gas delivery cannula. As shown in FIG. 38, end 420 of nasal interface 402 may be connected to tubing 416 at end 418 of fluid delivery conduit 410 in a similar manner described above with regard to the connection of end 420 and tubing 422. In such an embodiment, end 419 may be sealed off completely by flexible membrane 421.

The delivery of oxygen to at least one nostril of the patient may be controlled by the position of fluid delivery conduit 410 relative to nasal interface 402. For example, when fluid delivery conduit 410 is in a first position relative to the nasal interface 402, as shown in FIG. 37, fluid delivery conduit 410 is configured to deliver oxygen to both nostrils of the patient. In the first position, nostril interfaces 405, 406 of the nasal interface 402 are located substantially in the middle of outlet orifices 413, 414, thereby allowing oxygen to flow around sealing portions 407, 408 and into the nostrils of the patient.

Figure 39:
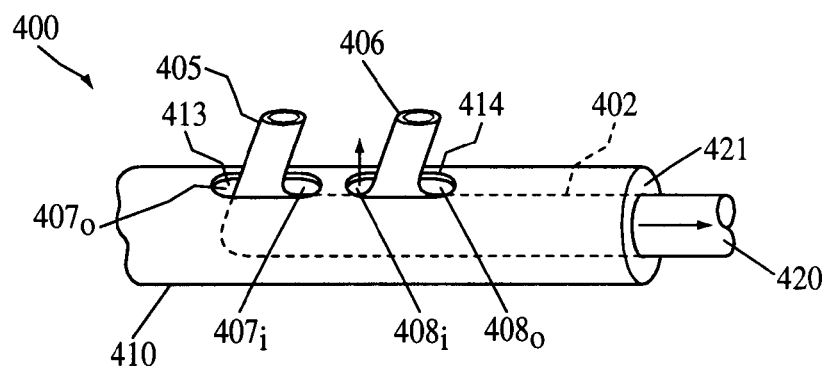
FIG. 39 is a perspective view of the patient interface of FIG. 37 with the fluid delivery conduit in a second position relative to the nasal interface.

As shown in FIG. 39, when fluid delivery conduit 410 is in a second position relative to the nasal interface 402, fluid delivery conduit 410 is configured to deliver the oxygen mostly, or even completely, to only one of the nostrils of the patient. This is due to the positions of sealing portions 407, 408 relative to outlet orifices 413, 414. Specifically, sealing portions 407, 408 do not extend laterally from nostril interfaces 405, 406 to the same distance on both sides of nostril interfaces 405, 406. As shown in FIG. 35, inner sections 407i, 408i of sealing portions 407, 408, respectively, are shorter than outer sections 407o, 408o of sealing portions 407, 408. Inner sections 407i, 408i being defined as the sections that are adjacent each other.

Returning to FIG. 39, because inner section 408i is shorter than outer section 407o, when fluid delivery conduit 410 is moved slightly to the left relative to nasal interface 402, the fluid may flow around sealing portion 408, and the fluid generally does not flow around sealing portion 407. In an embodiment, sealing portion 407 may not provide a complete seal with fluid delivery conduit 410, but may instead provide a slightly leaking seal. Even with a leaking seal, the majority of the flow is only provided to one of the nostrils. As such, the fluid is provided generally to only one nostril.

Figure 40:
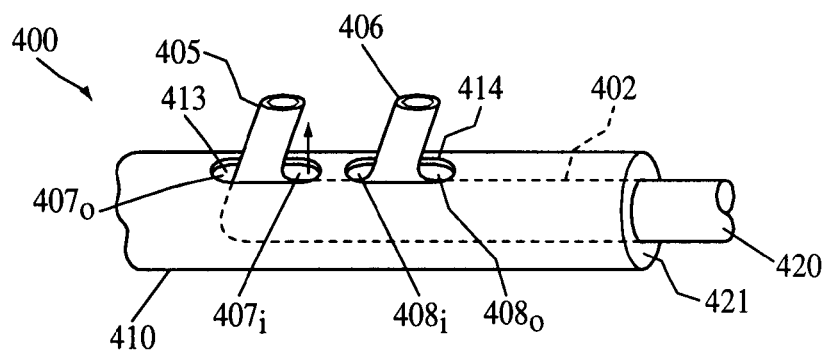
FIG. 40 is a perspective view of the patient interface of FIG. 37 with the fluid delivery conduit in a third position relative to the nasal interface.

Similarly, as shown in FIG. 40, when fluid delivery conduit 410 is moved slightly to the right relative to nasal interface 402, the fluid can flow around sealing portion 407, and the fluid does not flow around sealing portion 408. In an embodiment, sealing portion 408 may not provide a complete seal with fluid delivery conduit 410, but may instead provide a leaking seal. Even with a leaking seal, the majority of the flow is only provided to one of the nostrils. As such, the fluid is provided generally to only one nostril.

By providing an adjustable patient interface so that delivery of a fluid, such as oxygen, may be adjusted to one or both nostrils, the fluid may be delivered to the patient more effectively. For example, if one of the nostrils of the patient is obstructed so that the fluid may not flow to the nasal cavity, the patient interface 400 may be adjusted so that the fluid is generally provided to the unobstructed nostril.

In addition, where fluid (oxygen) is provided to both nostrils, it is possible to regulate (adjust) the relative amount of fluid being provided to one nostril relative to the other by having one of the openings left intentionally larger that the other based on the slightly off centered position of delivery conduit 410 relative to nasal interface 402.

Patient interface 400 may be mounted to the patient by any suitable method, such as by routing tubing 416, 421 at least partially around the ears of the patient, or by connecting the tubing to straps that are received by the ear. In an embodiment, either tubing may be replaced by "dummy" tubing that serves as only as a way to mount the interface to the patient. The embodiments described above are not intended to be limiting in any way.

The patient interfaces described in each of the embodiments above may be configured to provide physiological function measurements from central vascular sites located in and near the nose, e.g. in the outer nose tissues, septum, upper lip, cheeks, etc. Such physiological function measurements may include central photoplethysmography, which may be defined as the measurement and recording of the photoplethysmogram (PPG) from central vascular sites. Measurements from central sites on a patient's head provide access to well perfused regions, which are branches of the internal or external carotid arteries.

Central photoplethysmographic measurements offer generally significantly stronger, robust and reliable signals than peripheral sites (sites at the finger tips or toes). For example, nasal sites may require less power, in the order of 10× or more, than peripheral sites, such as the patient's finger tips, etc. As such, having the ability to combine physiological function measurements with fluid measurements in the same general location may be clinically valuable. A photoplethysmographic sensor may be used to take such physiological measurements.

Specifically, photoplethysmographic sensors may also be used to measure blood oxygen levels ($SPO_2$) and effort. Photoplethysmographic sensors may be transmittance-type sensors, or may be reflectance-type sensors. A transmittance-type sensor measures light extinction as light passes through a portion of blood-perfused tissue. For example, light may be transmitted from one side of a portion of blood-perfused tissue with an emitter, and may be recorded by a detector that is situated across that portion of the tissue. A reflectance-type sensor measures light that is reflected back from the tissue and includes a transmitter (e.g. a light source) and a detector that are locate on the same side of the tissue. For both types of sensors, multiple signals from the detector may be used to estimate the oxygen saturation of the blood and the pulse rate of the patient from changes in absorption of the light detected throughout blood pulse cycles. The technology is based on the differential absorbance of different wavelengths of light by different species of hemoglobin as explained in further detail in U.S. Pat. No. 7,024,235, which is hereby incorporated by reference herein in its entirety.

Embodiments of the present invention, described in more detail below, relate to the improved patient interfaces, described above, that provide improved nasal and/or oral carbon dioxide sampling and carbon dioxide sampling and oxygen delivery, and also provide an integrated physiological function sensor, such as a central photoplethysmographic sensor.

Figure 41:
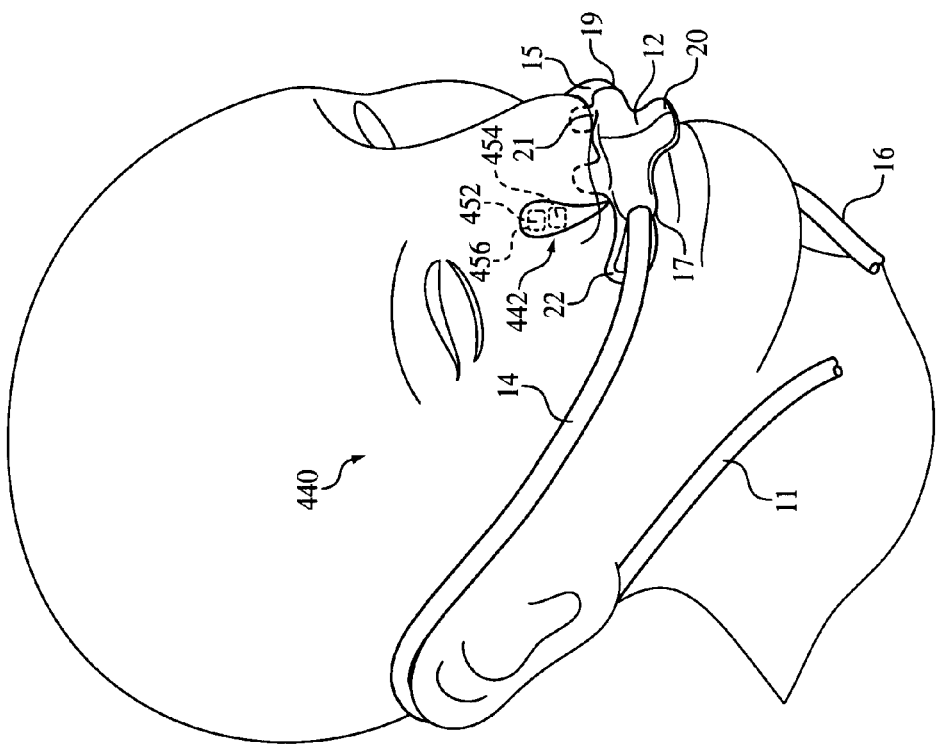
FIG. 41 is a perspective view of another embodiment of the patient interface of FIG. 1.

FIG. 41 illustrates a patient interface 440 according to an embodiment of the invention. As illustrated, the patient interface 440 includes the features and attributes of the patient interface 10 illustrated in FIGS. 1-3. Accordingly, common features are labeled in FIG. 41 with the same reference characters that are shown in FIGS. 1-3, and will not be described in detail here. The interface 440 of the present embodiment may be an oral and nasal carbon dioxide sampling cannula or appliance, with optional oxygen delivery, that also includes a physiological function sensor 442 that is connected with the body portion 12, as shown in FIG. 41. In an embodiment, sensor 442 is a photoplethysmographic sensor.

Figure 42:
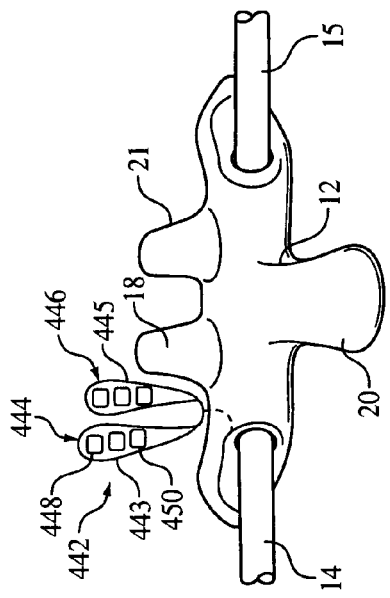
FIG. 42 is a front view of another embodiment of the patient interface of FIG. 41.

In the embodiment illustrated in FIG. 42, sensor 442 includes an emitter 444 and a detector 446. Emitter 444 of the sensor 442 is configured to engage an outside surface of an alar sidewall of the nose, and detector 446 of sensor 442 is configured to engage an inside surface of the alar sidewall of the nose so that the alar sidewall is located in between emitter 444 and detector 446. It is also contemplated that the emitter may engage an inside surface of the alar sidewall and the detector may engage an outside surface of the alar sidewall. In an embodiment, emitter 444 and detector 446 are respectively formed on opposite legs 443 and 445, respectively, of a U-shaped resilient structure forming a part of the body of sensor 442, so that when legs 443, 445 of the U-shaped configuration are separated to receive the alar sidewall, the resiliency of sensor 442 allows it to clip or clamp the alar sidewall between legs 443, 445. Such clamping may improve the signal that is generated by the sensor because outside effects may be reduced.

In an embodiment, emitter 444 includes a light source 448, which may be a red or infrared LED or light emitting diode. In another embodiment, emitter 444 also includes second light source 450, which may be an infrared or red LED. The output of the red LED may be centered at 660 nm and the infrared LED may be centered at 880 nm. However, other wavelengths of visible and infrared light are also contemplated. Detector 446 is configured to detect the wavelength(s) of light being emitted by emitter 444 after the light has been transmitted through the tissue in between emitter 444 and detector 446. This type of sensor and the processing of the signals generated by this type of sensor are known in the art, and is described in, for example, U.S. Pat. No. 7,024,235, which is hereby incorporated by reference in its entirety.

In an exemplary embodiment, sensor 442 includes an emitter 452 and a detector 454 that may both engage the outside surface of the patient's nose, as shown in FIG. 41. Emitter 452 may include at least one light source 456, such as an LED. In such an embodiment, detector 454 is configured to detect the light that is reflected from the tissue to which the emitter emits the light. This type of reflectance type sensor is known in the art, and is described in, for example, U.S. Pat. No. 7,024,235, which is hereby incorporated by reference in its entirety, and U.S. Pat. No. 6,263,223, which is hereby incorporated by reference in its entirety.

Figure 43:
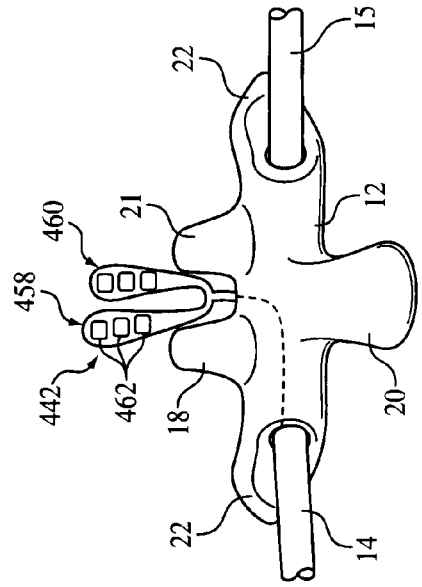
FIG. 43 is a front view of another embodiment of the patient interface of FIG. 42.

In another exemplary embodiment, shown in FIG. 43, sensor 442 includes an emitter 458 that engages one side of the septum of the patient's nose, and a detector 460 that engages the other side of the septum so that the septum is essentially clamped in between the emitter and the detector. It should be noted that the pressure applied to the septum is sufficient so that the sensor stay in place but does not apply undue pressure on the septal region. Similar to the emitters discussed above, emitter 458 may include at least one light source 462, and detector 460 may be configured to detect the amount of light that transmits through the septum.

A signal may be provided from each detector 446, 454, 460 and communicated to a central processor that is configured to process the signal into meaningful data for the clinician to monitor. For example, from the signal may be used to create a PPG signal and/or determine oxygen saturation (i.e., oxygenation of the blood) in the blood-perfused tissue from which the signal was created and/or determine the respiratory rate of the patient. As discussed in further detail below, patient interface 440 may also be used as part of an apnea monitor.

Sensor 442 may include a wireless transmitter that sends the signal wirelessly to the central processor. In another embodiment, the sensor may be hardwired, with wiring being harnessed with or integrally formed with the tubing forming the fluid paths.

Sensor 442 may be used in conjunction with any of the interfaces discussed above and illustrated in FIGS. 1-34. The illustrated embodiment is not intended to be limiting in any way.

Figure 44:
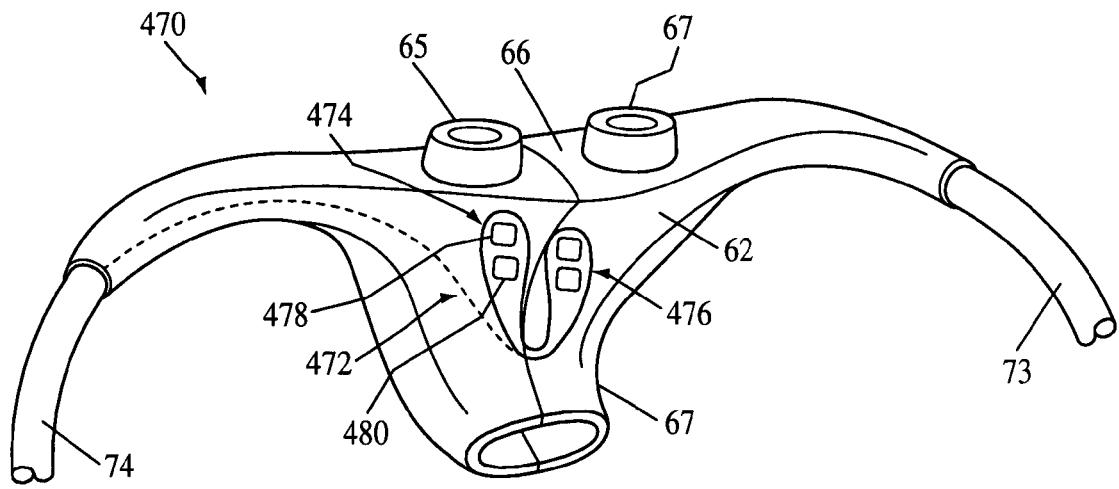
FIG. 44 is a back view of another embodiment of the patient interface of FIG. 10.

FIG. 44 illustrates a patient interface 470 according to an embodiment of the invention. Patient interface 470 incorporates the features and attributes of the patient interface 60 illustrated in FIGS. 9-11 and described above. Accordingly, common features are labeled in FIG. 44 with the same reference characters that are shown in FIGS. 9-11, and will not be described in detail here. Interface 470 may be an oral and nasal carbon dioxide sampling cannula or appliance with optional oxygen delivery that also includes a physiological function sensor 472 that is connected with body portion 62, as shown in FIG. 44. In an embodiment, sensor 472 is a photoplethysmographic sensor.

In the embodiment illustrated in FIG. 44, sensor 472 includes an emitter 474 and a detector 476. Emitter 474 of sensor 472 is configured to engage an outside surface of the patient's upper lip (or portion of skin immediately above the lip), and detector 476 of sensor 472 is configured to engage an inside surface of the upper lip (or portion of flesh immediately above the lip) so that a portion of the upper lip (or flesh) is located in between the emitter and the detector. It is also contemplated that the emitter may engage an inside surface of the patient's upper lip and the detector may engage an outside surface of the upper lip. In an embodiment, emitter 474 and detector 476 are provided on a U-shaped clip or clamping arrangement as discussed previously, so as to clamp the portion of the upper lip therebetween. Such clamping or secure engagement may improve the signal that is generated by the sensor because outside effects may be reduced.

In an embodiment, emitter 474 includes a light source 478, which may be a red or infrared LED or light emitting diode. In another embodiment, emitter 474 also includes second light source 480, which may be an infrared LED or red LED. Detector 476 is configured to detect the wavelength(s) of light being emitted by emitter 474 after the light has been transmitted through the tissue in between the emitter and the detector. As discussed above, this type of sensor and the processing of the signals generated by this type of sensor are known in the art.

Figure 45:
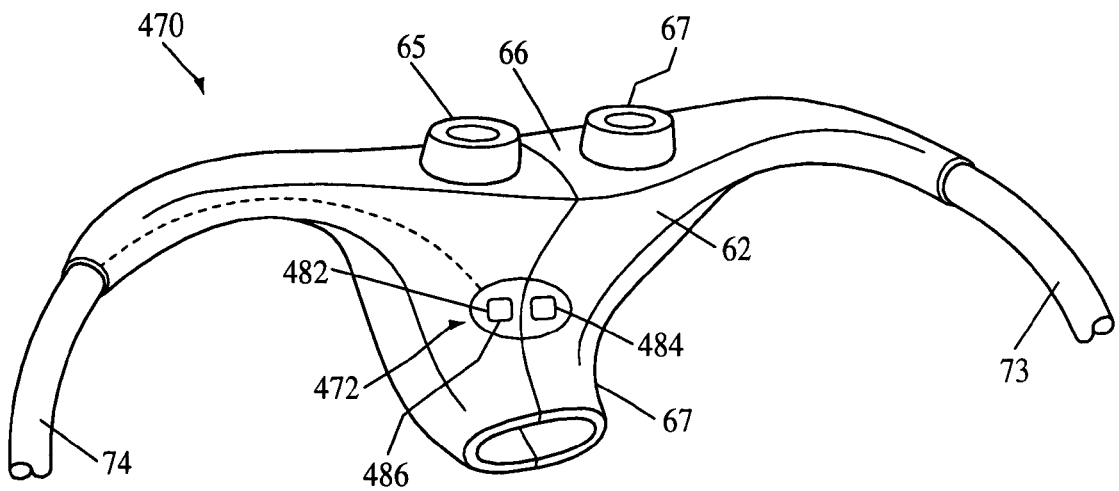
FIG. 45 is a back view of another embodiment of the patient interface of FIG. 44.

In an exemplary embodiment, sensor 472 includes an emitter 482 and a detector 484 that may both engage the outside surface of the patient's upper lip, as shown in FIG. 45. Emitter 482 may include at least one light source 486, such as an LED. In such an embodiment, detector 484 is configured to detect the light that is reflected from the tissue to which the emitter emits the light. As discussed above, this type of reflectance type sensor is known in the art.

Similar to the embodiments described above, a signal may be provided from each detector 476, 484 and communicated to a central processor that is configured to process the signal into meaningful data for the clinician to monitor. As discussed above, the signal may be provided via a wireless interface or a hardwired interface with the processor. The signal may be used to create a PPG signal and/or determine oxygen saturation (i.e., oxygenation of the blood) in the upper lip and/or determine the respiratory rate of the patient, as well as other measurements from the PPG signal which may be determined via known time and frequency based methods. Such measurements may include DC level, and different frequency components may be used to determine thoracic pressure and blood pressure, as described in PCT publication no. WO 04/080300 A1, which is hereby incorporated by reference in its entirety. The patient interface 470 may also be used as part of an apnea monitor, discussed below.

Sensor 472 may be configured to be used in conjunction with any of the interfaces discussed above that include an oral sampler. The illustrated embodiment is not intended to be limiting in any way.

Figure 46:
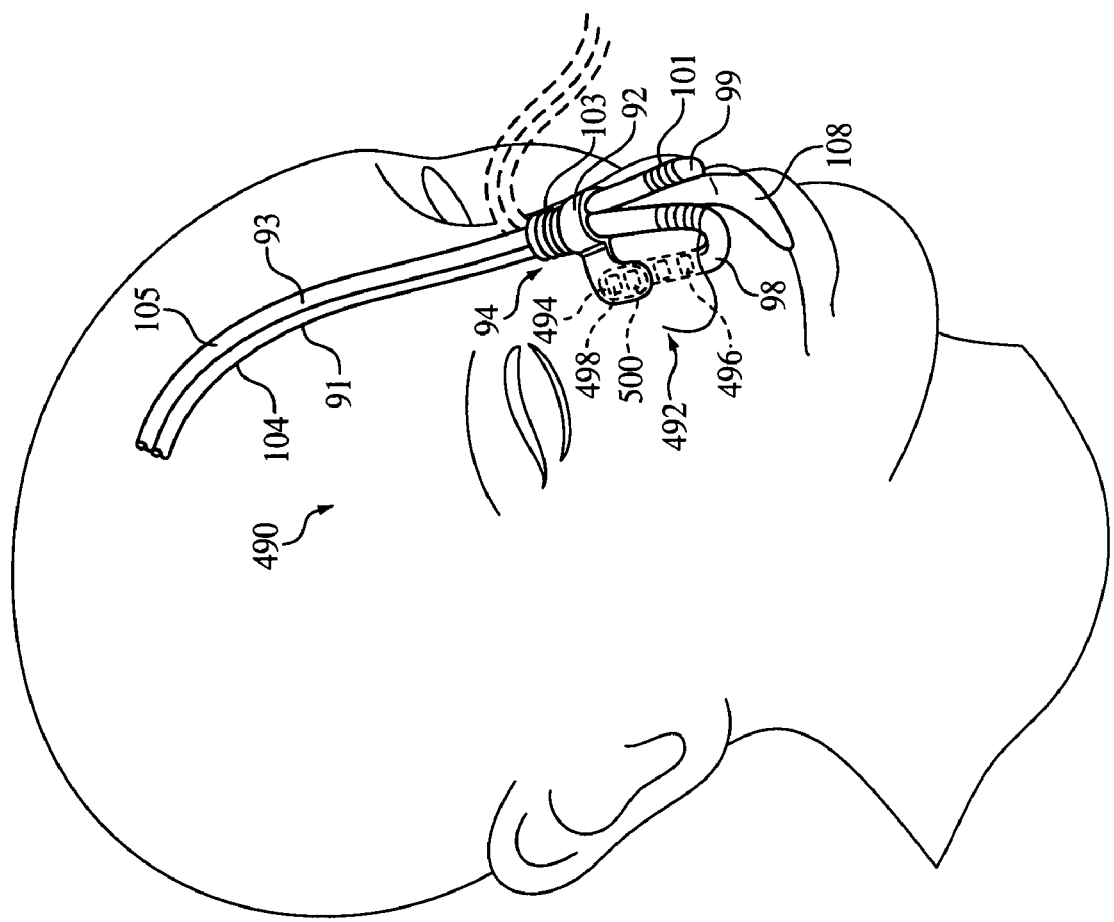
FIG. 46 is a perspective view of another embodiment of the patient interface of FIG. 13.

FIG. 46 illustrates a patient interface 490 according to an embodiment of the invention. Patient interface 490 includes the features and attributes of patient interface 90 illustrated in FIGS. 13 and 14 and described above. Accordingly, common features are labeled in FIG. 46 with the same reference characters that are shown in FIGS. 13 and 14, and will not be described in detail here. Interface 490 may be an oral and nasal carbon dioxide sampling cannula or appliance with optional oxygen delivery, and a physiological function sensor 492. In an embodiment, the physiological function sensor 492 may be a photoplethysmographic sensor. Like sensors 442, 472 described above, sensor 492 may be of the transmittance type or a reflectance type.

As shown in FIG. 46, sensor 492 includes an emitter 494 that is connected to attachment device 94, and a detector 496 that is connected to one of nostril interfaces 98, 99 that extends into the nostril of the patient. Emitter 494 engages an outside surface of the nose, and detector 496 engages in internal surface of the nostril such that a portion of the nose (alar sidewall or above the super-alar crease) is located in between the emitter and the detector, as shown in FIG. 46. It is also contemplated that the emitter may engage an internal surface of the nostril and the detector may engage an outside surface of the nose. In other words, emitter 494 and detector 496 are located on opposite sides of the same blood-perfused tissue of the nose.

In the illustrated embodiment, emitter 494 includes a light source 498, which may be a red or infrared LED or light emitting diode. In another embodiment, emitter 494 also includes second light source 500, which may be an infrared or red LED. Detector 496 is configured to detect the wavelength(s) of light being emitted by the emitter after the light has been transmitted through the tissue in between the emitter and the detector. As discussed above, this type of sensor and the processing of the signals generated by this type of sensor are known in the art.

Figure 47:
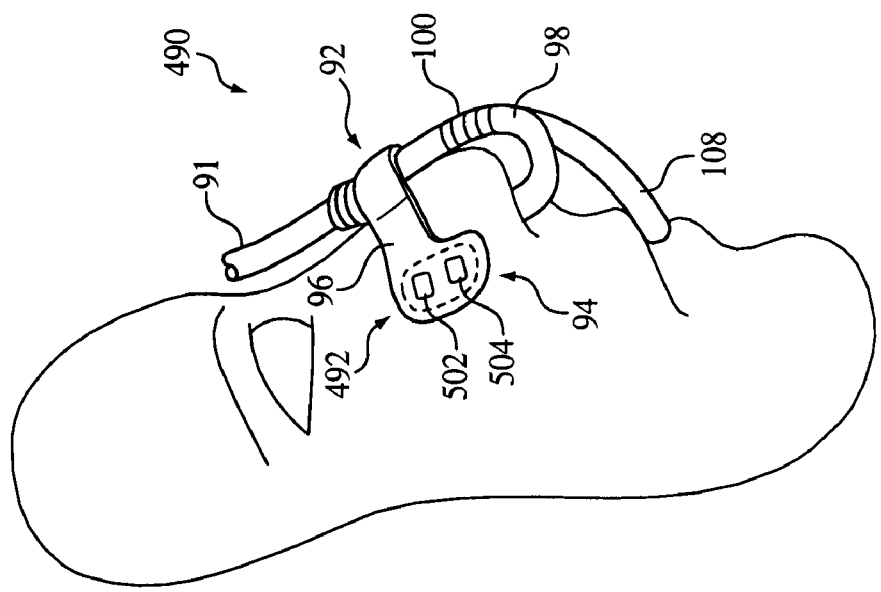
FIG. 47 is a side view of another embodiment of the patient interface of FIG. 46.

In an embodiment, sensor 492 includes an emitter 502 and a detector 504 that may both be connected to attachment portion 94 and engage the outside surface of the patient's nose proximate to each other, as shown in FIG. 47. Emitter 502 may include at least one light source 506, such as an LED. In such an embodiment, detector 504 is configured to detect the light that is reflected from the tissue to which the emitter emits the light.

Similar to the embodiments described above, a signal may be provided from each detector 496, 504 and communicated to a central processor that is configured to process the signal into meaningful data for the clinician to monitor. As discussed above, the signal may be provided via a wireless interface or a hardwired interface with the processor. The signal may be used to create a PPG and/or determine oxygen saturation (i.e., oxygenation of the blood) in the alar sidewall and/or determine the respiratory rate of the patient. The patient interface 490 may also be used as part of an apnea monitor, discussed below.

Figure 48:
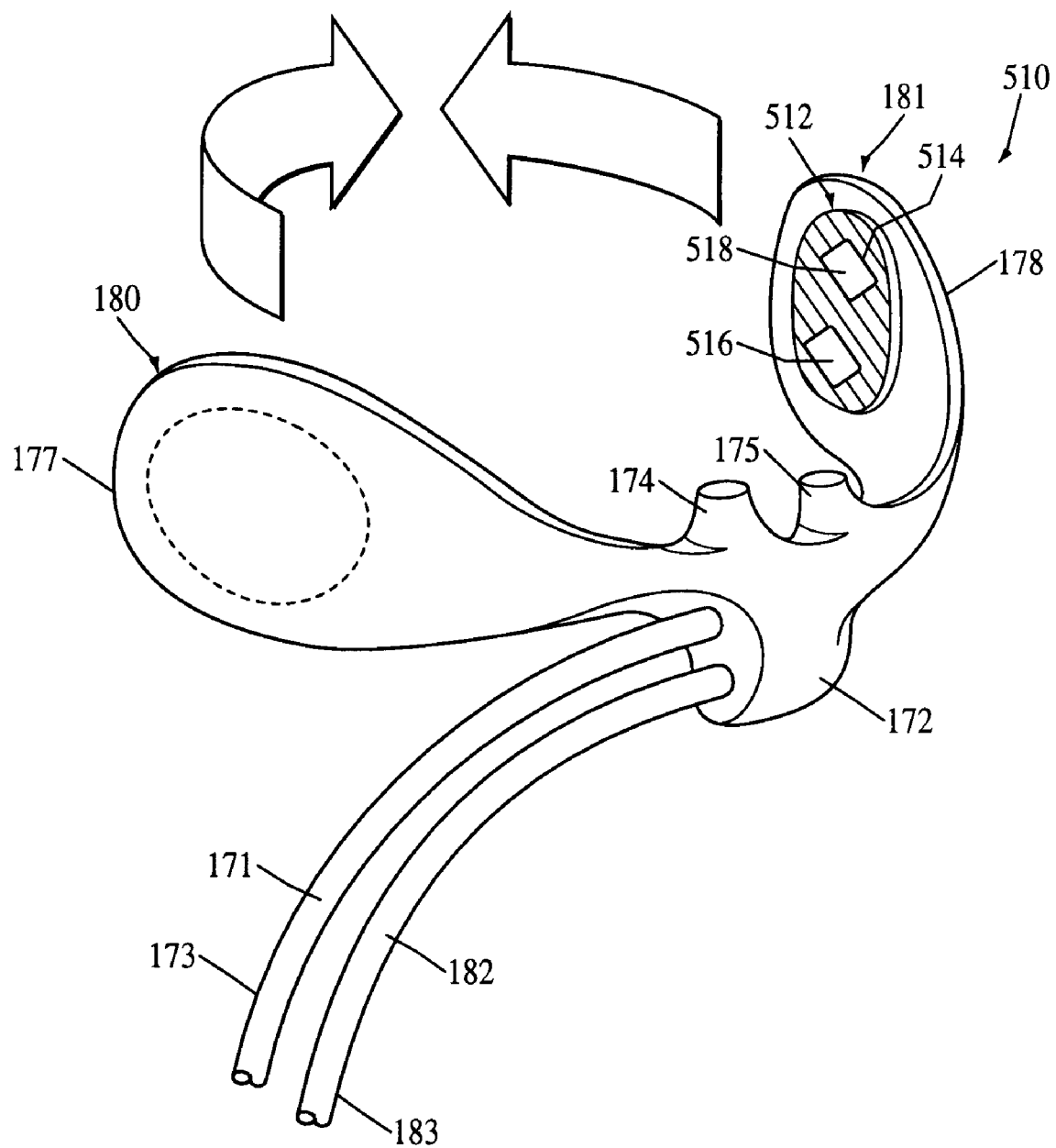
FIG. 48 is a perspective view of another embodiment of the patient interface of FIG. 21.

FIG. 48 illustrates a patient interface 510 according to an embodiment of the invention. Patient interface 510 includes the features and attributes of the patient interface 170 illustrated in FIG. 21 and described above. Accordingly, common features are labeled in FIG. 48 with the same reference characters that are shown in FIG. 21, and will not be described in detail here. Patient interface 510 may be an oral and nasal carbon dioxide sampling cannula or appliance with optional oxygen delivery, and a physiological function sensor 512. In an embodiment, physiological function sensor 512 may be a photoplethysmographic sensor. Like some embodiments of sensors 442, 472, 492 described above, sensor 492 may be of the reflectance type.

As shown in FIG. 48, sensor 512 includes an emitter 514 that is connected to the attachment device 176, specifically to one of extensions 177, 178, and a detector 516 that is also connected to the attachment device at the same extension as the emitter. Emitter 514 and detector 516 both engage adjacent portions of the patient's cheek. Emitter 514 may include at least one light source 518, such as an LED. In such an embodiment, detector 516 is configured to detect the light that is reflected from the tissue to which the emitter emits the light. As discussed above, this type of reflectance type sensor is known in the art.

Similar to the embodiments described above, a signal may be provided from detector 516 and communicated (either wirelessly or hardwired) to a central processor that is configured to process the signal into meaningful data for the clinician to monitor. The signal may be used to create a PPG and/or determine oxygen saturation (i.e., oxygenation of the blood) in the cheek and/or determine the respiratory rate of the patient. Patient interface 510 may also be used as part of an apnea monitor, discussed below.

Figure 49:
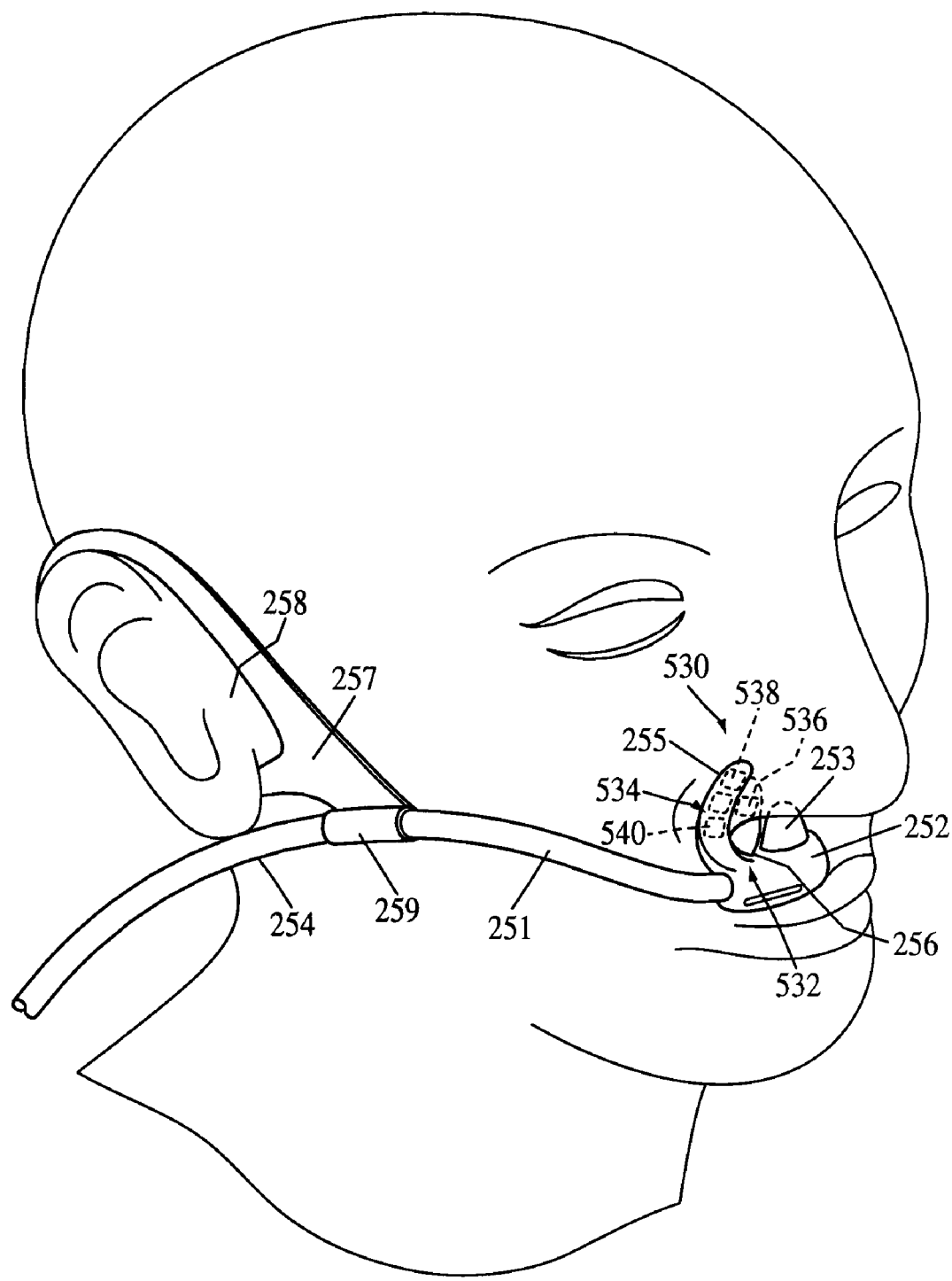
FIG. 49 is a perspective view of another embodiment of the patient interface of FIG. 27.

FIG. 49 illustrates a patient interface 530 according to an embodiment of the invention. Patient interface 530 includes the features and attributes of patient interface 250 illustrated in FIG. 27 and described above. Accordingly, common features are labeled in FIG. 49 with the same reference characters that are shown in FIG. 27, and will not be described in detail here. Patient interface 530 include a carbon dioxide sampling and/or oxygen delivery cannula or appliance that samples and/or delivers fluid from/to a single nostril and a physiological function sensor 532. In an embodiment, physiological function sensor 532 may be a photoplethysmographic sensor.

Similar to the embodiment illustrated in FIG. 41 and discussed above, in the embodiment shown in FIG. 49, sensor 532 includes an emitter 534 and a detector 536. The emitter is configured to engage an outside surface of the nose (the alar sidewall outside surface), and the detector is configured to engage an inside surface of the nose (the alar sidewall inner surface) so that a portion of the nose (the alar sidewall) is located in between the emitter and the detector. It is also contemplated that the emitter may be configured to engage an inside surface of the nose and the detector may be configured to engage an outside surface of the nose.

In an embodiment, emitter 534 and detector 536 may be biased toward each other in the manners previously described so as to clamp or securely engage the portion of the nose (the alar sidewall) therebetween via an attachment structure. For example, emitter 534 may be disposed on a first securement portion 255, and detector 536 may be disposed on second securement portion 256. Such secure engagement may improve the signal that is generated by the sensor because outside effects may be reduced.

In an embodiment, emitter 534 includes a light source 538, which may be a red or infrared LED or light emitting diode. In another embodiment, the emitter also includes second light source 540, which may be an infrared or red LED. The detector is configured to detect the wavelength(s) of light being emitted by the emitter after the light has been transmitted through the tissue in between emitter 534 and detector 536. This type of sensor and the processing of the signals generated by this type of sensor are known in the art, as discussed above.

Figure 50:
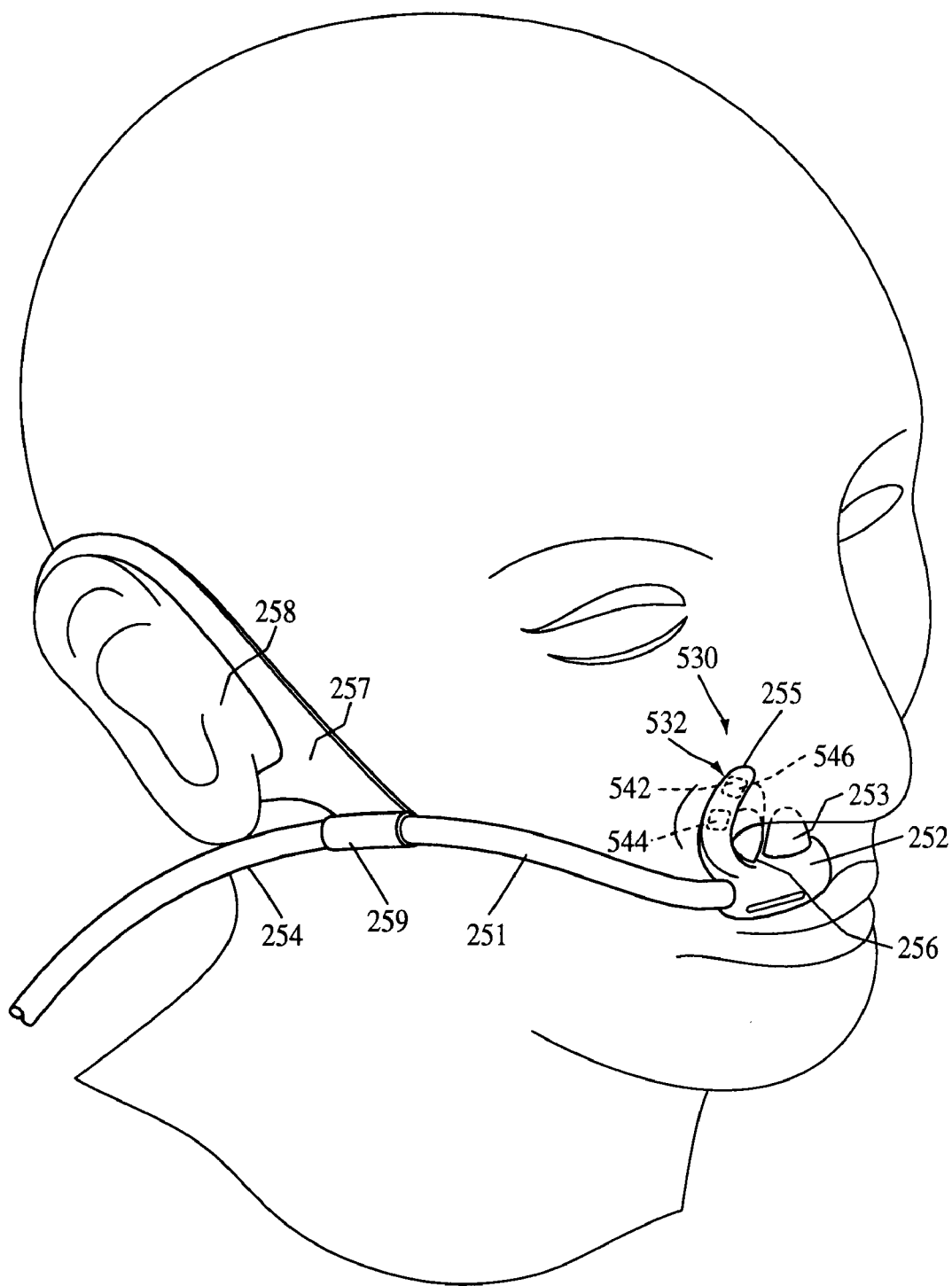
FIG. 50 is a perspective view of another embodiment of the patient interface of FIG. 49.

In an embodiment, shown in FIG. 50, sensor 532 includes an emitter 542 and a detector 544 that may both engage the outside surface of the patient's nose. The emitter may include at least one light source 546, such as an LED. Like the embodiments discussed above, in such an embodiment, the detector is configured to detect the light that is reflected from the tissue to which the emitter emits the light. This type of reflectance type sensor is known in the art, as discussed above, and will not be discussed in further detail herein.

Sensor 532 may also be used with embodiments of the patient interface that include nostril interface 340 illustrated in FIG. 33. In such embodiments, detector 536 may be mounted to nostril interface 340 either on moisture exchanger 348 or on an outside surface of outer conduit 346, and emitter 534 may be provided on an outside surface of the alar sidewall such that the alar sidewall is located in between the emitter and the detector in a manner described above. Alternatively, a separate U-shaped clip or clamping structure may be used, as described above, so the sensor does not interfere with the nostril interface.

Similar to the embodiments described above, a signal may be provided from detectors 536, 544 and communicated (wirelessly or hardwired) to a central processor that is configured to process the signal into meaningful data for the clinician to monitor. The signal may be used to create a PPG and/or determine oxygen saturation (i.e., oxygenation of the blood) in the upper lip and/or determine the respiratory rate of the patient. Patient interface 530 may also be used as part of an apnea monitor, discussed below.

It should be appreciated that the physiological function sensors described above may be adapted to be provided with embodiments of the patient interface described herein. The illustrated embodiments are not intended to be limiting in any way.

In addition, embodiments of the patient interfaces and physiological function sensors described above may be used as part of an apnea monitor for monitoring apnea in a patient.

In the United States, an apnea monitor is defined by regulation in 21 C.F.R.§868.2377(a) as "a complete system intended to alarm primarily upon the cessation of breathing timed from the last detected breath." As also defined by 21C.F.R. §868.2377(a), "The apnea monitor also includes indirect methods of apnea detection, such as monitoring of heart rate and other physiological parameters linked to the presence or absence of adequate respiration."

A guidance document provided by the U.S. Department of Health and Human Services entitled "Class II Special Controls Guidance Document: Apnea Monitors; Guidance for Industry and FDA," issued on Jul. 17, 2002 and hereby incorporated by reference in its entirety, suggests that an apnea monitor should have at least one primary/direct means for detecting apnea; at least one secondary/indirect means for detecting apnea, e.g., heart rate; a timer to measure the duration of apneic episodes; visual and audible alarms to signal an apneic episode; visual and audible alarms to signal a secondary/indirect condition due to an apneic episode; and a sensor fault alarm for both primary/direct and secondary/indirect means detecting apnea which activates within 5 seconds of a sensor failure. Secondary/indirect methods measure physiologic parameters that change as a result of apnea. For example, apnea may lead to hypoxia, which in turn may lead to bradycardia. Methods for measuring such parameters include pulse oximetry (POX) and electrocardiography (ECG). A robust, redundant method for apnea monitoring is still sought.

Figure 51:
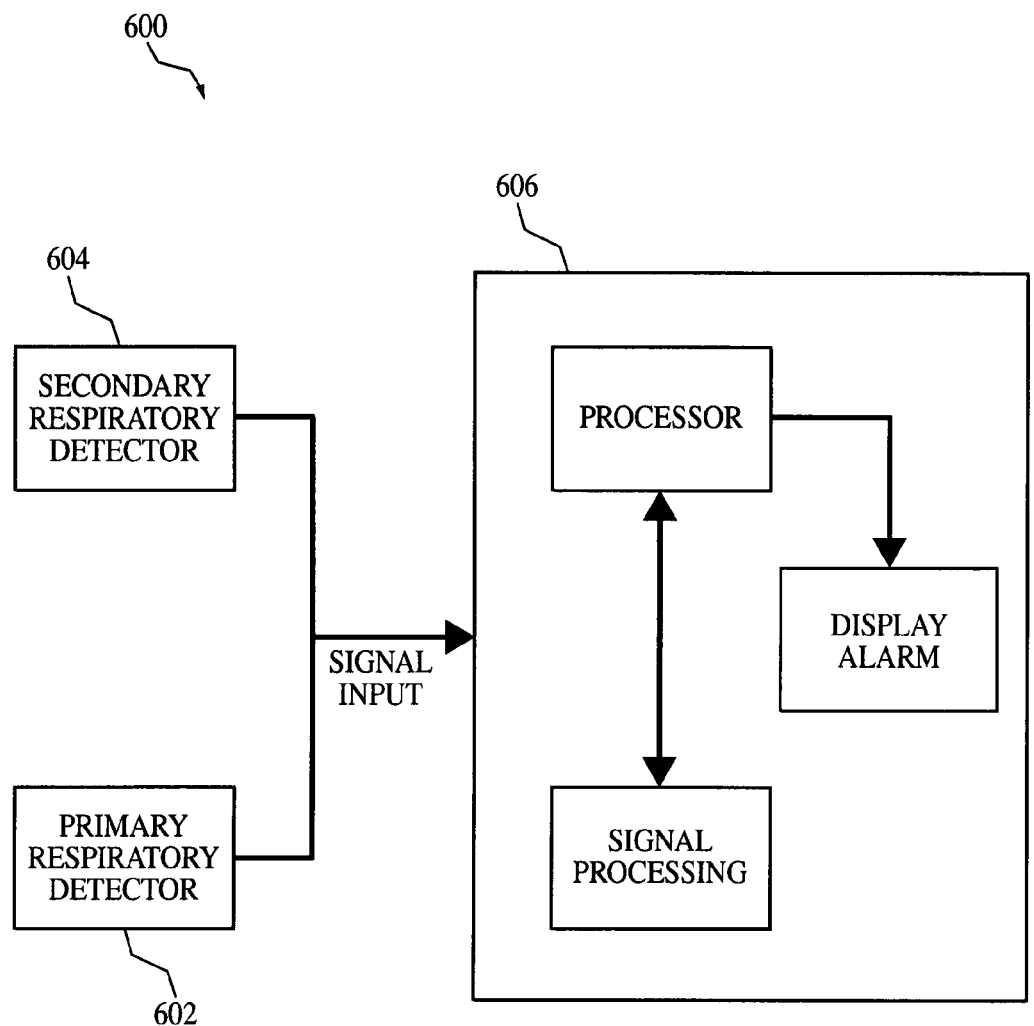
FIG. 51 is a block diagram of an embodiment of an apnea monitor.

In accordance with an exemplary embodiment of the present invention, an apnea monitor 600 is provided. As shown in FIG. 51, apnea monitor 600 includes a primary respiratory detector 602 that is configured to directly measure patient breathing by monitoring exhalation of a fluid from the patient's nasal cavity and/or oral cavity. Primary respiratory detector 602 may incorporate any of the embodiments of patient interfaces, cannulas, or appliances described above.

Apnea monitor 600 also includes a secondary respiratory detector 604 that is configured to indirectly measure patient breathing by monitoring a physiological function of the patient proximate to the patient's nasal cavity and/or oral cavity. Secondary respiratory detector 604 may include any of the embodiments of physiological function sensors described above.

As shown in FIG. 51, apnea monitor 600 also includes a processor 606 configured to process data from signals output from primary respiratory detector 602 and secondary respiratory detector 604. Processor 606 is configured to use both signals to determine whether an apnea is present, and to signal an alarm or perform some other action if apnea is present.

Figure 52:
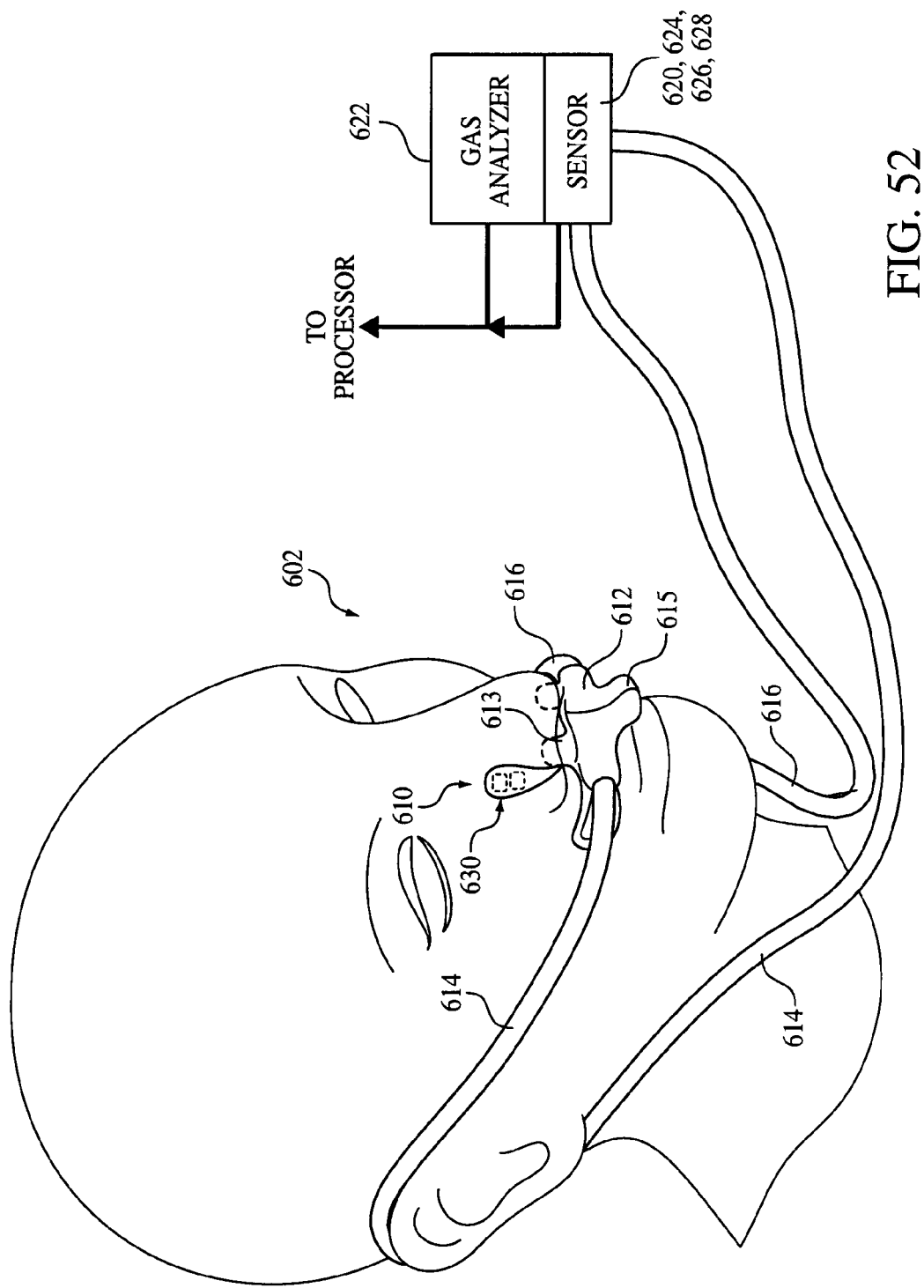
FIG. 52 is perspective view of an embodiment of the apnea monitor of FIG. 51.

As shown in FIG. 52, primary respiratory detector 602 may include a patient interface 610 that is configured to be mounted to the patient's head. Patient interface 610 includes an appliance 612 that includes a nostril interface 613 that is configured to receive (and/or supply) fluid from (and/or to) the nasal cavity when the patient breathes. Patient interface 610 also includes a fluid path 614 that is communicated with nostril interface 613. Fluid path 614 is configured to communicate the fluid to a sensor 620 configured to sense a property of the fluid. In an embodiment, patient interface 610 may include an oral sampler 615 that is configured to receive fluid being exhaled from the patient's mouth. A fluid path 616 is communicated with oral sampler 615 and is configured to communicate the fluid to sensor 620.

In an embodiment, sensor 620 may be part of a gas analyzer 622 that is configured to analyze a concentration of a gas, such as carbon dioxide, in the fluid over time. Gas analyzer 622 is configured to provide an output signal to processor 606.

In an embodiment, sensor 620 is a pressure sensor 624 that is configured to sense the pressure in the fluid being exhaled by the patient over time. Specifically, pressure sensor 624 may be in communication with fluid path 616 in a manner that measures the pressure pulses that are generated in the fluid path when the patient exhales. If the pressure in fluid path 616 is not detected to change over a predetermined period of time, it may be an indication that the patient may have stopped breathing. Such pressure sensors are generally known, and will not be described in further detail herein. See, for example, Montserrat J M et al., "Evaluation of Nasal Prongs for Estimating Nasal Flow," Am J Respir Crit Care Med. 1997 January;155(1):211-5, which is hereby incorporated by reference in its entirety. Pressure sensor 624 is configured to provide an output signal to processor 606.

In another exemplary embodiment, sensor 620 is an acoustic sensor 626 that is configured to sense whether fluid is being exhaled by the patient over time. Specifically, acoustic sensor 626 may be located on or near patient interface 610 and positioned such that the signals generated by the sensor when the patient exhales may be measured. If such signals have not been detected with a predetermined period of time, it may be an indication that the patient may have stopped breathing. Such acoustic sensors are known (and may also be ultrasonic sensors) and will not be described in further detail herein. Acoustic sensor 626 is configured to provide an output signal to processor 606.

In a still further embodiment, sensor 620 is a thermistor 628 that is configured to sense the temperature of the fluid being exhaled by the patient over time. Specifically, thermistor 628 may detect sudden increases and decreases in the temperature in fluid path 616 that correspond to the normal pattern of breathing by the patient. Such thermistor sensors are known, and will not be described in further detail herein. See, for example, U.S. Pat. No. 5,190,048, which is hereby incorporated by reference in its entirety. By monitoring such changes over time, thermistor 628 may detect when the temperature in fluid path 616 has not changed for an abnormal period of time, which may be an indication that the patient has stopped breathing. Thermistor 628 is configured to provide an output signal to processor 606.

As indicated above, secondary detector 604 may include a physiological function sensor 630, of the type discussed above. In such embodiments, the secondary detector may be mounted to appliance 612 and may be a central photoplethysmographic sensor. At least a portion of secondary detector 604 may be configured to engage an external surface of a portion of the nose, or the septum of the nose, or the upper lip of the patient, or the face (e.g., cheek) of the patient in a manner that is described above and illustrated in the figures.

In an embodiment, secondary respiratory detector 604 is configured to send another output signal to processor 606 from which the respiratory rate of the patient may be derived independent from primary respiratory detector 602. The technique of receiving a signal from physiological function sensor and deriving the respiratory rate of the patient from such sensing is known in the art from, for example, PCT publication no. WO 00/21438, which is hereby incorporated by reference in its entirety, and US patent application publication no. 2005/0027205, which is hereby incorporated by reference in its entirety.

Figure 53:
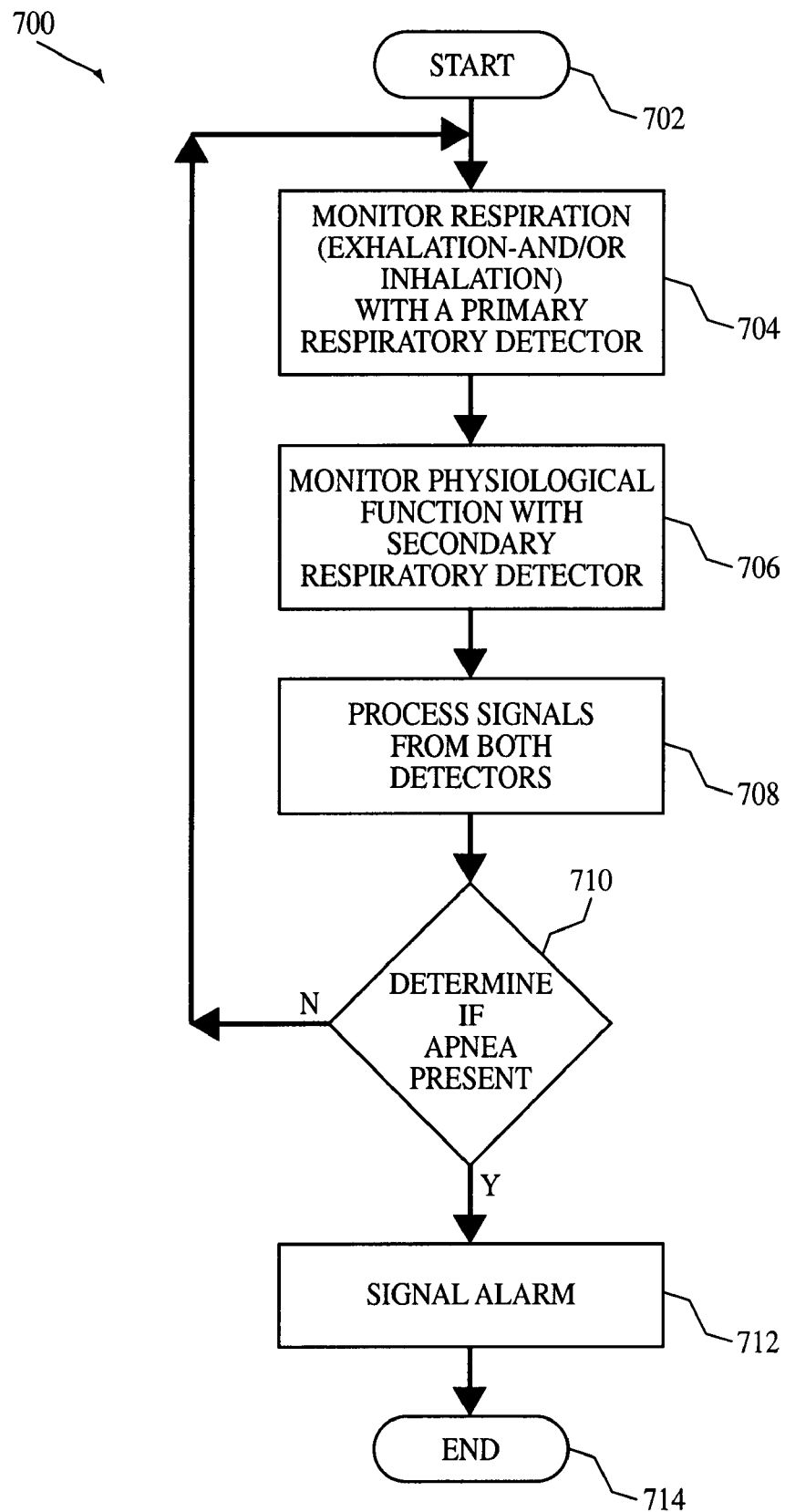
FIG. 53 is a flow diagram of a method for monitoring apnea.

In an embodiment, as shown in FIG. 53, a method for monitoring apnea 700 is provided. The method starts at step 702. At step 704, the patient's respiration is monitored with a primary respiratory detector. For example, the patient's inhalation of oxygen or the patient's exhalation of a fluid from the nasal cavity or oral cavity is monitored at step 704. At step 706, a physiological function of the patient proximate to the patient's nasal cavity or oral cavity with a secondary respiratory detector 604 is monitored. At step 708, data from output signals of primary respiratory detector 602 and secondary respiratory detector 604 are processed. At step 710, a determination is made as to whether apnea is present, based on the processing of the signals at step 706. If it is determined that an apnea is present, the method continues to step 712 where an alarm is signaled. The method ends at step 714. If it is determined that apnea is not present, the method returns to step 704. Of course, the monitoring of the exhalation at step 704 and the monitoring of the physiological function at step 706 may be done simultaneously, or one may be completed just before (e.g., within milliseconds) or just after (e.g., within milliseconds) the other.

By monitoring the a primary respiratory signal and a secondary respiratory signal at the same central site at or near the nose of the patient, a robust and rapidly responding respiratory rate and measurement of a physiological function, such as blood oxygenation, at a single site may be provided. In addition, by using embodiments of the patient interface that includes the physiological function sensor, a single interface may be provided.

This "single site" sensor has numerous potential applications including, for example, conscious sedation, patient-controlled analgesia (PCA), emergency medicine, and ambulatory monitoring. It allows for more robust and reliable monitoring capability by providing data fusion of respiratory signals, less sensitivity to low perfusion and motion artifact related problems that may plague peripheral oxygen saturation measurements, and a more robust and reliable alarm system. For example, monitoring oxygen saturation using a finger sensor (e.g. peripheral measurement) and ventilation via carbon dioxide sampling with a conventional nasal cannula, arguably results in a monitoring system that is less reliable than that of the present invention because of the known motion and low perfusion problems of the peripheral site and the potential for two separate sites for disconnection.

With a single site sensor, it is expected that the sensitivity and specificity for detecting clinical events will be greater than with the conventional multi-site approach. This is in part due to greater robustness of the central photoplethysmographic signal, as well as the faster detection of clinical changes by this signal than the peripheral signal. The morphology of the central photoplethysmogram is less filtered by the vasculature than the peripherally measured photoplethysmogram and as such provides a much richer signal from which physiologic measures may be determined. Patient-controlled analgesia (PCA) allows patients to receive pain medication, such as opioids (e.g. morphine, fentanyl) on-demand. This is typically accomplished by providing the patient with a button to activate the pump delivery system.

To address the growing concerns regarding the safety of PCA, particularly ventilatory depression, capnography measured using conventional nasal cannula and pulse oximetry usually measured at the finger has been provided as an option with some conventional PCA pumps. The inclusion of capnography permits the detection of ventilatory depression occurring as a result of narcotics before decreases in oxygenation in the patients occur. The use of a single site sensor can be used in conjunction with PCA for safety monitoring and also as input into a PCA system for feedback control. This could provide a more robust system than can be provided by a conventional sensor configuration.

Conscious sedation, i.e., moderate sedation/analgesia, produced by the intravenously administration of certain medications such as midazolam, propofol and fentanyl, permits a patient to respond to physical stimulation and verbal commands, and to maintain an unassisted airway. Conscious sedation facilitates diagnostic or therapeutic procedures such as a biopsy, radiologic imaging study, endoscopic procedures, radiation therapy, or bone marrow aspiration. Given the associated risks, e.g., respiratory depression, with conscious sedation, medical organizations have published guidelines mandating or strongly recommending appropriate monitoring. This monitoring has included pulse oximetry and capnography. The use of a single site sensor of the present invention can be used during conscious sedation for safety monitoring. This provides a more robust system than can be provided by a conventional sensor configuration.

As described for conscious sedation, the features of the single site sensor can also find application during emergency medicine and ambulatory monitoring.

It is also contemplated that the single site sensor of the present invention may include reusable and/or disposable components which may separable for one another. Embodiments of exemplary gas sampling with reusable components is found in U.S. provisional patent application No. 60/833,678, the contents of which are hereby incorporated by reference herein in their entirety. With single site sensor embodiments including components such as a photoplethysmographic sensor, it is contemplated that this portion may be separable from the rest of the single site sensor so that it may be cleaned between patients and reused.

It is also contemplated the single site physiological function sensor cable may communicate the measured signals using electrical or pneumatic pathways to measurement components and that these pathways may be separate physically or integrated as in a multilumen cable comprising pneumatic and electrical conduits. This pathway may be connected to a wearable hub or module that may transmit the data remotely which may be positioned behind the ear, clipped to belt, or as part of sensor shirt.

Also, a patient interface is contemplated comprising a physiological function sensor connected with an appliance portion wherein the appliance portion comprises an airway adapter of a sensor for detecting a carbon dioxide gas in an expiratory gas of a subject, comprising an airway case, adapted to be disposed below nostrils of the subject; and an optional mouth guide, adapted to be disposed in front of a mouth of the subject so as to define a space in communication with the airway passage. Embodiments of airway adapters adapted to be disposed below the nostrils of a subject is found in U.S. patent application Ser. Nos. 10/779,852 (US patent publication no. 2004/0206907) and 11/019,792 (US patent publication no. 2005/0245836), the contents of both which are hereby incorporated by reference herein in their entirety. It is contemplated that the sensor and airway adapter of the '852 application and the '792 application may serve as a primary respiratory detector and that the physiological function sensor serves as a secondary respiratory detector.

The embodiments of a single-site sensor shown for monitoring apnea may be extended to an ambulatory sleep diagnostic sensor. More specifically, the exemplary embodiments of a combined gas sampling and photoplethysmographic measurement patient interfaces shown in FIGS. 41 to 50 may be adapted to be used as a single-site sensor for ambulatory sleep diagnostics. Conventional ambulatory sleep diagnostic systems (such as the Stardust II from Respironics, Inc. Murrysville, Pa.) require that the subject be instrumented with a chest band as a surrogate for effort, a finger sensor for $SPO_2$ measurements, and a nasal cannula for flow estimation using pressure measurements.

The present invention utilizes a central photoplethysmographic sensor in combination with a flow measurement system. The flow measurement system may based upon known methods, such as pressure and/or flow monitoring via a catheter or via a thermister type of flow monitor. The present invention contemplates that the signal from central photoplethysmographic sensor, the PPG signal, may be used as a non-invasive surrogate of effort. Examples of such signal are disclosed in U.S. patent applicant Nos. 10/652,992 (US patent publication no. 2004/0040560), and 11/758,159, the contents of each of which are incorporated herein by reference.

It is further contemplated that a combined nasal/oral cannula configuration would increase the sensitivity and specificity of the system for individuals prone to mouth breathing. EEG electrodes may be added to the cannula tubing with leads running to an interface. Acoustic microphones and vibrations sensors may be added anywhere (already discussed above) along the tubing or cannula to assess snoring and upper airway instability. An accelerometer can be added to determine patient position relative to gravity and/or provide actigraphy.

Figure 54:
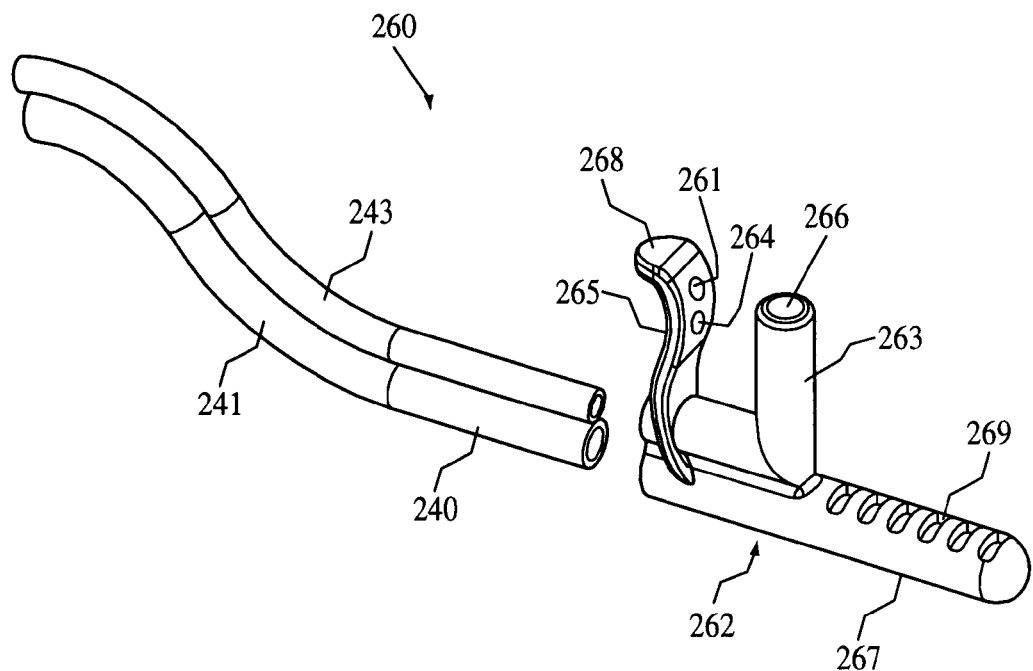
FIG. 54 is a perspective view of an embodiment of a patient interface for gas sampling from a single nostril and supplemental gas delivery.

FIG. 54 illustrates a further embodiment of a patient interface 260 of the present invention configured to be a gas sampling and/or gas delivery cannula that samples from a single nostril and/or delivers fluid from/to a single nostril or both nostrils. As noted for patient interface 250, it is also contemplated that patient interface 260 may be particularly advantageous if a naso-gastric feeding tube is in use, thereby effectively making one nostril unavailable for sampling or oxygen delivery.

As illustrated, patient interface 260 includes a body portion 262 that is configured to communicate with fluid paths 241 and 243. A single nostril interface 263 with opening 266 extends from body portion 262 and is configured to be received by the patient's nostril, and to provide fluid communication between the nasal cavity via the nostril and fluid path 243. A fluid delivery portion 267 extends from body portion 262 and includes a plurality of openings 269 which are in fluid communication with fluid path 241. Fluid path 241 and openings 269 are sized to permit delivery to either/or both of the nares oxygen with a volumetric flow at least 6 LPM. The present invention contemplates that the length of fluid delivery portion 267, as well as the number and size of openings 269, could be altered for different sizes of patient interface 260.

In the illustrated embodiment, fluid path 241 is defined by tubing 240. Tubing 24 is configured to carry fluid exhaled by the patient through the nasal cavity via one nostril to a receiver, such as a gas analyzer, for determining the concentration of carbon dioxide in the fluid over time. In another embodiment, tubing 254 is configured to supply a fluid containing oxygen, to the nasal cavity as the patient inhales though the nostril.

It is also contemplated that tubing 254 may be configured to also define a second fluid path, either in the manner discussed above and illustrated in FIG. 24, or in the manner illustrated in FIG. 30, or in the manner illustrated in FIG. 55, which is discussed in greater detail later. Similarly, in an embodiment, body portion 252 and nostril interface 253 may include separators that separate the fluids communicated between the nostril and the first and second fluid paths.

Interface 260 also includes a securement portion 265 that is disposed proximate to nostril interface 263 and is constructed and arranged to engage an exterior surface of the patient's nose such that the securement portion and the nostril interface are cooperable to securely engage or lightly clamp an alar sidewall portion of the patient's nose therebetween. In the embodiment shown, securement portion 265 is curved and includes a tabbed portion 268 which permits easier gripping and placement onto the nostril. These features allow easy and comfortable application to most subject's nostrils. The resiliency of the material forming securement portion 265 and/or of nostril interface 263 create an inwardly directed spring force once these portions are separated to receive the alar sidewall therebetween so as to engage or lightly clamp the alar sidewall portion of the patient's nose between the nostril interface and the securement portion.

Patient interface 260 also may optionally include a second securement portion (not shown) that is disposed more proximate to nostril interface 263 than first securement portion 265. Second securement portion may be constructed and arranged to cooperate with first securement portion 265 so as to clamp a portion of the patient's nose therebetween. Such an arrangement would not interfere with nostril interface 263, and would not require the nostril interface to participate in the clamping function.

Similar to the embodiment illustrated in FIG. 49, securement portion 265 may include an emitter portion 261 and a detector portion 264. The emitter and detector portions are configured to engage an outside surface of the nose (the alar sidewall outside surface). The detector is configured to detect the wavelength(s) of light being emitted by the emitter after the light has been reflected by the tissue in communication with emitter portion 261 534 and detector portion 264. This type of sensor and the processing of the signals generated by this type of sensor are known in the art.

The present invention also contemplates that the emitter portion 261 and detector portion 264 may be biased toward each other in the manners previously described, so as to clamp or securely engage the portion of the nose (the alar sidewall) therebetween. For example, emitter portion 261 may be disposed on securement portion 265, and detector 264 may be disposed on second securement portion (not shown) which engages an inside surface of the nose. Emitter portion 261 includes at least one light source, which may be a red and infrared LED or light emitting diode. Also, a plurality of light sources is contemplated. This embodiment would allow tissue measurements to be made at different wavelengths ranging from the ultraviolet to mid-infrared. Applications for such an arrangement include determining the concentration of oxy- and deoxyhemoglobin, as well as dyshemoglobins such as met- and carboxyhemoglobin. Also determining hemoglobin/hematocrit and other substances in the blood/tissue are contemplated. These may be LEDs, semiconductor lasers (e.g. edge emitting, VSCELs) or other light sources known in the art.

Figure 55:
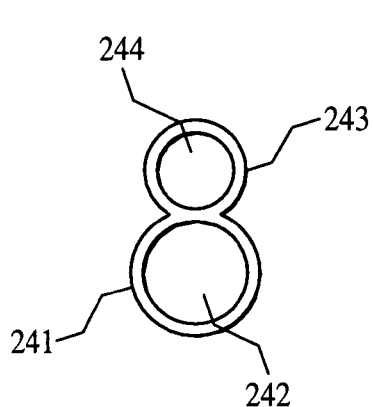
FIG. 55 is a cross-sectional view of a tubing portion of the interface of FIG. 54.

As shown in FIG. 55, tubing 240 includes for tubing portions 241 and 243 separating first fluid path 242 from second fluid path 243. This allows tubing portion 243 to be configured to receive a fluid being exhaled from the patient and tubing portion 241 to supply a fluid, such as oxygen, to be inhaled by the patient. Fluid paths 242, 243 may be of an equal cross-section, or one of the cross-sectional areas may be larger than the other. For example, in an exemplary embodiment, the cross-sectional area of fluid path 242 that supplies oxygen to the patient is larger than the cross-sectional area of fluid path 243 that receives fluid from the patient. It is also contemplated that tubing 240 may be configured to also define a second fluid path, either in the manner discussed above and illustrated in FIG. 24, or in the manner illustrated in FIG. 30. The illustrated embodiment is not intended to be limiting in any way.

Figure 56:
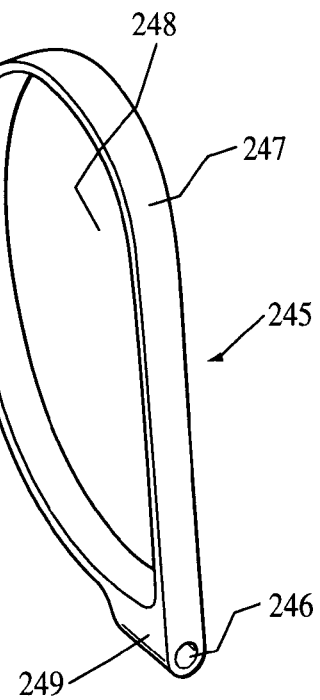
FIG. 56 is a perspective view of a strap that is configured to be received by an ear of the patient.

As illustrated in FIG. 56, patient interface 260 may include a head gear that includes a strap 245 that is configured to be received by an ear of the patient and is also connected to the tubing 240 so as to support tubing 240 and provide outward tension. As illustrated, strap 245 includes an opening 248 for receiving the ear, and a holding portion 249 that is configured to engage a portion of the tubing 240 and allow the tubing 240 to pass therethrough without creating a kink in the tubing. In the embodiment shown, holding portion 249 includes opening 246 through which tubing 240 passes. The present invention contemplates manufacturing strap 245 from a material or combination of materials that are suitable for processes such as injection molding. As such, identifying information, such as the product or company name, could be easily added to the outer surface of loop portion 247. The illustrated embodiment is not intended to be limiting in any way.

While each of the embodiments are described above in terms of their structural arrangements, it should be appreciated that the present invention also covers the associated methods of using the embodiments described above.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface comprising:
   a U-shaped body portion configured to communicate with a first fluid path, the body portion being configured to engage a bridge of a nose of a patient responsive to being donned by a patient;
   a U-shaped first nostril interface extending from the body portion, wherein the nostril interface communicates with the first fluid path, and wherein the first nostril interface is configured to extend generally over a tip of the nose of the patient and into a first nostril of the patient responsive to being donned by a patient and is sized and configured such that the first nostril interface does not completely block a nostril responsive to being donned by the patient;
   a first tubing that defines the first fluid path, where the first tubing is coupled to the first nostril interface; and
   a first securement portion extending from the body portion proximate the first nostril interface, wherein, in use, the securement portion is constructed and arranged to engage only an exterior alar sidewall surface of the patient's nose to clamp the body portion to the patient's nose and to secure the patient interface to the patient's nose, and wherein a resiliency of the first securement portion and the first nostril interface is configured to enable clamping of the alar sidewall portion of the patient's nose therebetween,
   wherein the body portion is configured to communicate with a second fluid path and further comprising a second U-shaped nostril interface extending from the body portion and operatively coupled to the second fluid path, wherein the second nostril interface is configured to extend over the tip of the nose of the patient and into a second nostril of the patient responsive to being donned by a patient, and
   wherein the body portion further includes an oral sampler configured to communicate with at least one of the first fluid path and the second fluid path through at least one conduit internal to the body portion, the oral sampler having an orifice configured to one or both of sample a fluid exhaled from the patient's mouth and supply oxygen to the patient's mouth.

2. A patient interface according to claim 1, wherein the securement portion is biased toward the first nostril interface responsive to the securement portion being disposed on the patient's nose.

3. A patient interface according to claim 1, further comprising a strap coupled to the tubing and adapted to support the tubing, the strap being configured to be received by an ear of a patient.

4. A patient interface according to claim 1, further comprising a second tubing that defines the second fluid path.

5. A patient interface according to claim 4, further comprising a strap for supporting the second tubing, the strap being configured to be received by an ear of the patient.

6. A patient interface according to claim 1, wherein the nostril interface and the first securement portion are integral with the body portion.

7. A patient interface comprising:
   a U-shaped body portion configured to communicate with a first fluid path, the body portion being configured to engage a bridge of a nose of a patient responsive to being donned by a patient;
   U-shaped first nostril interface extending from the body portion, wherein the nostril interface communicates with the first fluid path, and wherein the first nostril interface is configured to extend generally over a tip of the nose of the patient and into a first nostril of the patient responsive to being donned by a patient and is sized and configured such that the first nostril interface does not completely block a nostril responsive to being donned by the patient;
   a first tubing that defines the first fluid path, where the first tubing is coupled to the first nostril interface;
   a first securement portion extending from the body portion proximate the first nostril interface, wherein, in use, the securement portion is constructed and arranged to engage only an exterior alar sidewall surface of the patient's nose to clamp the body portion to the patient's nose and to secure the patient interface to the patient's nose, and wherein a resiliency of the first securement portion and the first nostril interface is configured to enable clamping of the alar sidewall portion of the patient's nose therebetween; and
   a physiological function sensor connected with the first securement portion for engagement with the skin of the nose of the patient, and wherein the physiological function sensor generates a signal based on a physiological function measurement,
   wherein the body portion further includes an oral sampler configured to communicate with at least one of the first fluid path and the second fluid path through at least one conduit internal to the body portion, the oral sampler having an orifice configured to one or both of sample a fluid exhaled from the patient's mouth and supply oxygen to the patient's mouth.

8. A patient interface according to claim 7, wherein the sensor comprises an emitter for emitting a signal and a detector for detecting the signal.

9. A patient interface according to claim 8, wherein the emitter comprises at least one light source and the detector comprises a photodetector.

10. A patient interface comprising:
a U-shaped body portion configured to communicate with a first fluid path, the body portion being configured to engage a bridge of a nose of a patient responsive to being donned by a patient;
a U-shaped first nostril interface extending from the body portion, wherein the nostril interface communicates with the first fluid path, and wherein the first nostril interface is configured to extend generally over a tip of the nose of the patient and into a first nostril of the patient responsive to being donned by a patient and is sized and configured such that the first nostril interface does not completely block a nostril responsive to being donned by the patient;
a first tubing that defines the first fluid path, where the first tubing is coupled to the first nostril interface;
a first securement portion extending from the body portion proximate the first nostril interface, wherein, in use, the securement portion is constructed and arranged to engage only an exterior alar sidewall surface of the patient's nose to clamp the body portion to the patient's nose and to secure the patient interface to the patient's nose, and wherein a resiliency of the first securement portion and the first nostril interface is configured to enable clamping of the alar sidewall portion of the patient's nose therebetween; and
a second securement portion constructed and arranged to engage an interior surface of a patient's nose such that a portion of a nose is disposed between the first securement portion and the second securement portion,
wherein the body portion further includes an oral sampler configured to communicate with at least one of the first fluid path and the second fluid path through at least one conduit internal to the body portion, the oral sampler having an orifice configured to one or both of sample a fluid exhaled from the patient's mouth and supply oxygen to the patient's mouth.

11. A patient interface according to claim 10, further comprising a physiological function sensor connected with the first securement portion, the second securement portion or both for engagement with the skin of a nose of such a patient, and wherein the physiological function sensor generates a signal based on a physiological function measurement.

12. A patient interface according to claim 11, wherein the Physiological function sensor is disposed on the first securement portion and comprises an emitter for emitting a signal and a detector for detecting the signal, the second securement portion or both such that (a) the emitter engages an external surface of a portion the nose and the detector engages an internal surface of a portion of the nose, (b) the detector engages the external surface of a portion of the nose and the emitter engages the internal surface of a portion of such nose, (c) the emitter and the detector both engage the external surface of the nose, or (d) the emitter and the detector both engage the internal surface of the nose.

13. A patient interface comprising:
an appliance portion including:
a U-shaped body portion configured to communicate with a fluid path, the body portion being configured to engage a bridge of a nose of a patient responsive to being donned by a patient; and
a U-shaped nostril interface extending from the body portion, the nostril interface being configured to extend generally over a tip of the nose of the patient and into a nostril of the patient responsive to being donned by a patient and to provide fluid communication between the nostril and the fluid path, and wherein the nostril interface is sized and configured such that the first nostril interface does not completely block the nostril responsive to being received by the nostril;
a first tubing that defines the first fluid path, where the first tubing is coupled to the nostril interface;
a securement portion extending from the body portion and disposed proximate the nostril interface, and wherein, in use, the securement portion is constructed and arranged to engage only an exterior alar sidewall surface of a patient's nose to clamp the body portion to the patient's nose and to secure the patient interface to the patient's nose; and
a physiological function sensor connected with the appliance portion for engagement with the skin of the nose of the patient and generating a signal based upon a physiological function measurement,
wherein the body portion further includes an oral sampler configured to communicate with at least one of the first fluid path and the second fluid path through at least one conduit internal to the body portion, the oral sampler having an orifice configured to one or both of sample a fluid exhaled from the patient's mouth and supply oxygen to the patient's mouth.

14. A patient interface according to claim 13, wherein the sensor comprises an emitter for emitting a signal and a detector for detecting the signal.

15. A patient interface according to claim 14, wherein the emitter and the detector are biased toward each other.

16. A patient interface according to claim 13, wherein at least a portion of the sensor is disposed on the securement portion such that the portion of the sensor engages the exterior surface of the portion of the patient's nose.

17. A patient interface according to claim 16, wherein the sensor comprises an emitter for emitting a signal and a detector for detecting the signal, and wherein (a) the emitter and the detector are disposed on the securement portion and engage the exterior surface of the patient's nose, (b) the emitter is disposed on the securement portion and engages the exterior surface of the patient's nose and the detector is disposed within the nostril and engages an interior surface of the portion of the patient's nose, (c) the detector is disposed on the securement portion and engages the exterior surface of the patient's nose and the emitter is disposed within the nostril and engages an interior surface of the portion of the patient's nose, or (d) the emitter and the detector are disposed within the nostril and engage the interior surface of the patient's nose.

18. A patient interface according to claim 13, wherein a resiliency of the securement portion and the nostril interface is configured to enable clamping of an alar sidewall portion of the patient's nose therebetween.

19. A patient interface according to claim 13, wherein the nostril interface and the securement portion are integral with the body portion.

20. A patient interface comprising:
a U-shaped body portion configured to communicate with a first fluid path and a second fluid path, the body portion being configured to engage a bridge of a nose of a patient responsive to being donned by a patient;
a U-shaped first nostril interface extending from the body portion, wherein the first nostril interface communicates with the first fluid path, and wherein the first nostril interface is configured to extend generally over a tip of the nose of the patient and into a first nostril of the patient responsive to being donned by a patient and is sized and configured such that the first nostril interface does not completely block the first nostril responsive to being donned by the patient;

a U-shaped second nostril interface extending from the body portion and operatively coupled to the second fluid path, wherein the second nostril interface is configured to extend over the tip of the nose of the patient and into a second nostril of the patient responsive to being donned by a patient and is sized and configured such that second first nostril interface does not completely block the second nostril responsive to being donned by the patient;

a first tubing that defines the first fluid path, where the first tubing is coupled to the first nostril interface;

a second tubing that defines the second fluid path, where the second tubing is coupled to the second nostril interface; and a first securement portion extending from the body portion proximate the first nostril interface and a second securement portion extending from the body portion proximate the second nostril interface, the first and the second nostril interfaces located on the body portion between the first and the second securement portions, wherein, in use, each of the first and second securement portions is constructed and arranged to engage an exterior alar sidewall surface of a patient's nose to clamp the body portion to the patient's nose and to secure the patient interface to such a patient's nose, wherein the body portion further includes an oral sampler configured to communicate with at least one of the first fluid path and the second fluid path through at least one conduit internal to the body portion, the oral sampler having an orifice configured to one or both of sample a fluid exhaled from the patient's mouth and supply oxygen to the patient's mouth.

* * * * *